United States Patent
Rodriguez-Borlado et al.

(10) Patent No.: US 11,801,268 B2
(45) Date of Patent: Oct. 31, 2023

(54) METHODS OF TREATING OCULAR INFLAMMATION AND CHEMICAL INJURIES OF THE EYE WITH EXTRACELLULAR VESICLES

(71) Applicant: Capricor, Inc., Beverly Hills, CA (US)

(72) Inventors: Luis Rodriguez-Borlado, Manhattan Beach, CA (US); Houman Hemmati, Los Angeles, CA (US); Jennifer L Johnson, Van Nuys, CA (US); Kiel A. Peck, West Hollywood, CA (US); Rachel R. Smith, Cary, NC (US); Linda Marban, Santa Monica, CA (US)

(73) Assignee: Capricor, Inc., San Diego, CA (US)

( * ) Notice: Subject to any disclaimer, the term of this patent is extended or adjusted under 35 U.S.C. 154(b) by 188 days.

(21) Appl. No.: 16/084,186

(22) PCT Filed: Mar. 14, 2017

(86) PCT No.: PCT/US2017/022370
§ 371 (c)(1),
(2) Date: Jun. 19, 2020

(87) PCT Pub. No.: WO2017/160884
PCT Pub. Date: Sep. 21, 2017

(65) Prior Publication Data
US 2020/0289580 A1 Sep. 17, 2020

Related U.S. Application Data

(60) Provisional application No. 62/368,972, filed on Jul. 29, 2016, provisional application No. 62/308,166, filed on Mar. 14, 2016.

(51) Int. Cl.
*A61K 35/34* (2015.01)
*A61P 27/02* (2006.01)
*A61K 9/00* (2006.01)
*A61K 35/65* (2015.01)
*A61K 35/12* (2015.01)

(52) U.S. Cl.
CPC ............ *A61K 35/34* (2013.01); *A61K 9/0014* (2013.01); *A61K 9/0048* (2013.01); *A61K 35/12* (2013.01); *A61K 35/65* (2013.01); *A61P 27/02* (2018.01)

(58) Field of Classification Search
None
See application file for complete search history.

(56) References Cited

U.S. PATENT DOCUMENTS

2014/0099355 A1† 4/2014 Al-Qahtani

FOREIGN PATENT DOCUMENTS

EP 2882445 † 6/2015

† cited by third party

*Primary Examiner* — Michael V Meller
(74) *Attorney, Agent, or Firm* — Capricor, Inc.; Joseph Zahner

(57) ABSTRACT

The present invention relates to a method of treating a chemical injury of the eye, in particular alkali burn of the cornea, as well as ocular GVHD and similar inflammatory ocular conditions, with extracellular vesicles, in particular exosomes obtained from human cardiospheres or cardiosphere-derived cells. The present invention also provides a formulation comprising extracellular vesicles, in particular exosomes obtained from human cardiospheres or cardiosphere-derived cells, for subconjunctival or topical administration to the eye in the treatment of a chemical injury of the eye, in particular alkali burn of the cornea, as well as ocular GVHD and similar inflammatory ocular conditions.

9 Claims, 37 Drawing Sheets

Specification includes a Sequence Listing.

Fig. 1A
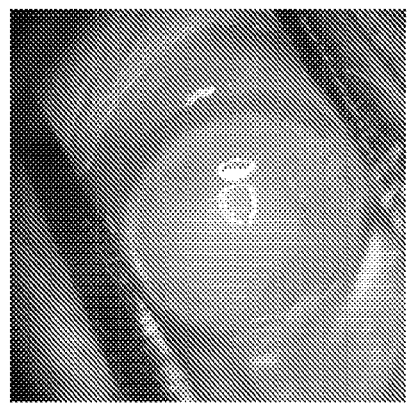
Fig. 1B
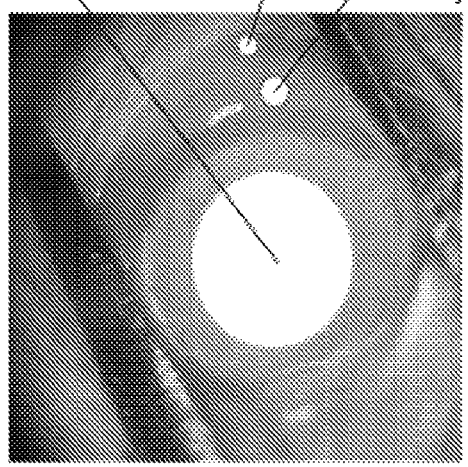
Fig. 1C
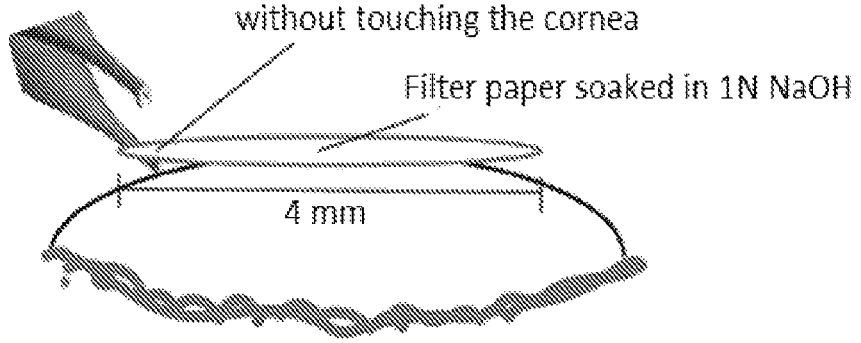

CORNEAL SURFACE AREA

VASCULAR PANNUS

Rx = CDC-EVs

Rx = vehicle control

Rx = CDC-EVs

Fig. 13B
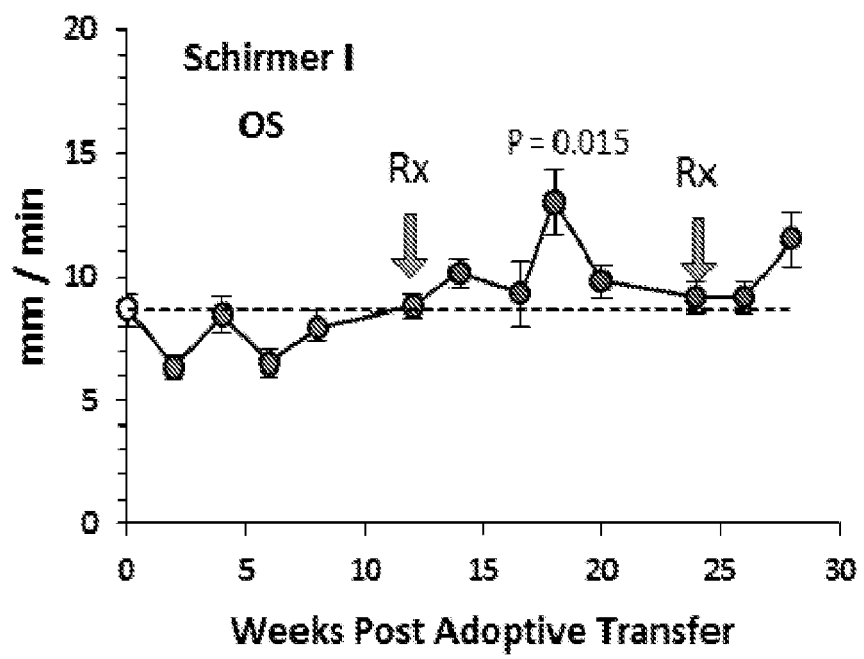
Rx = vehicle control
Figs. 14A-B
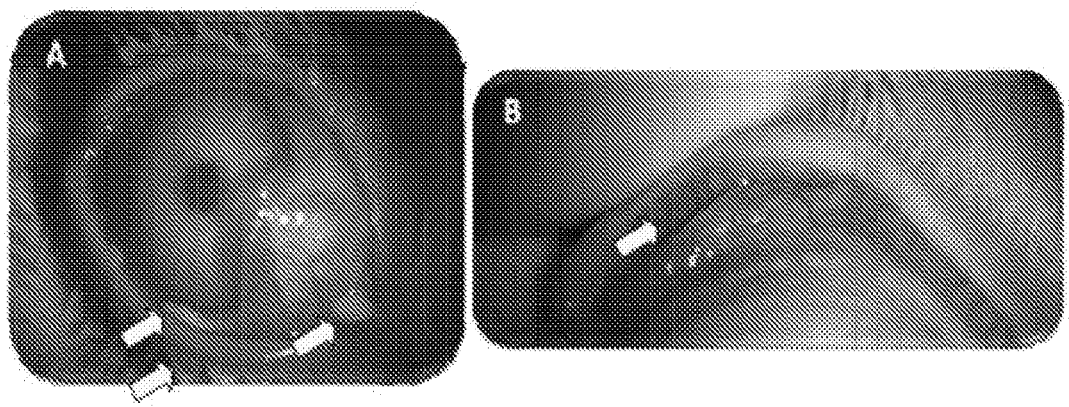

Figs. 15A-C
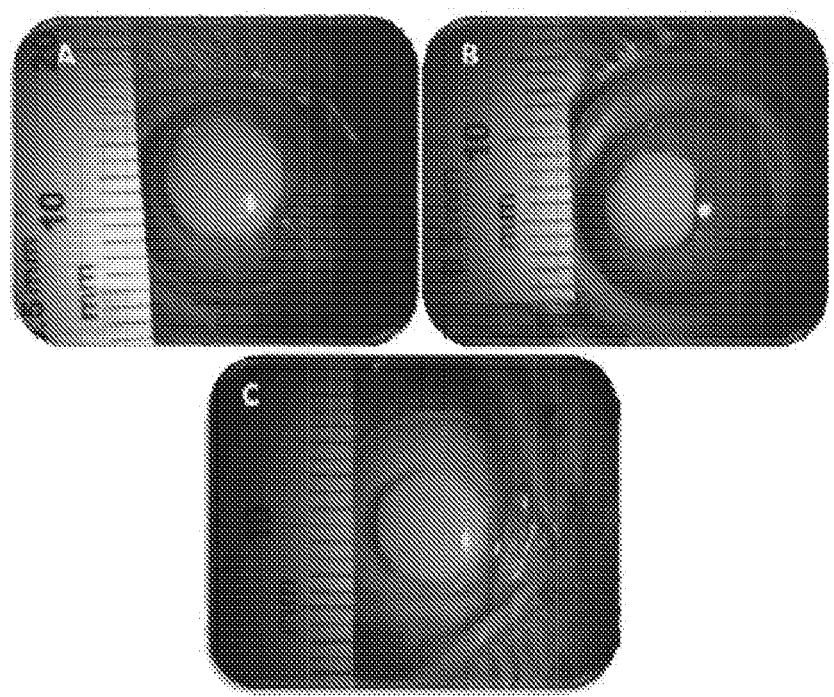
Fig. 16A
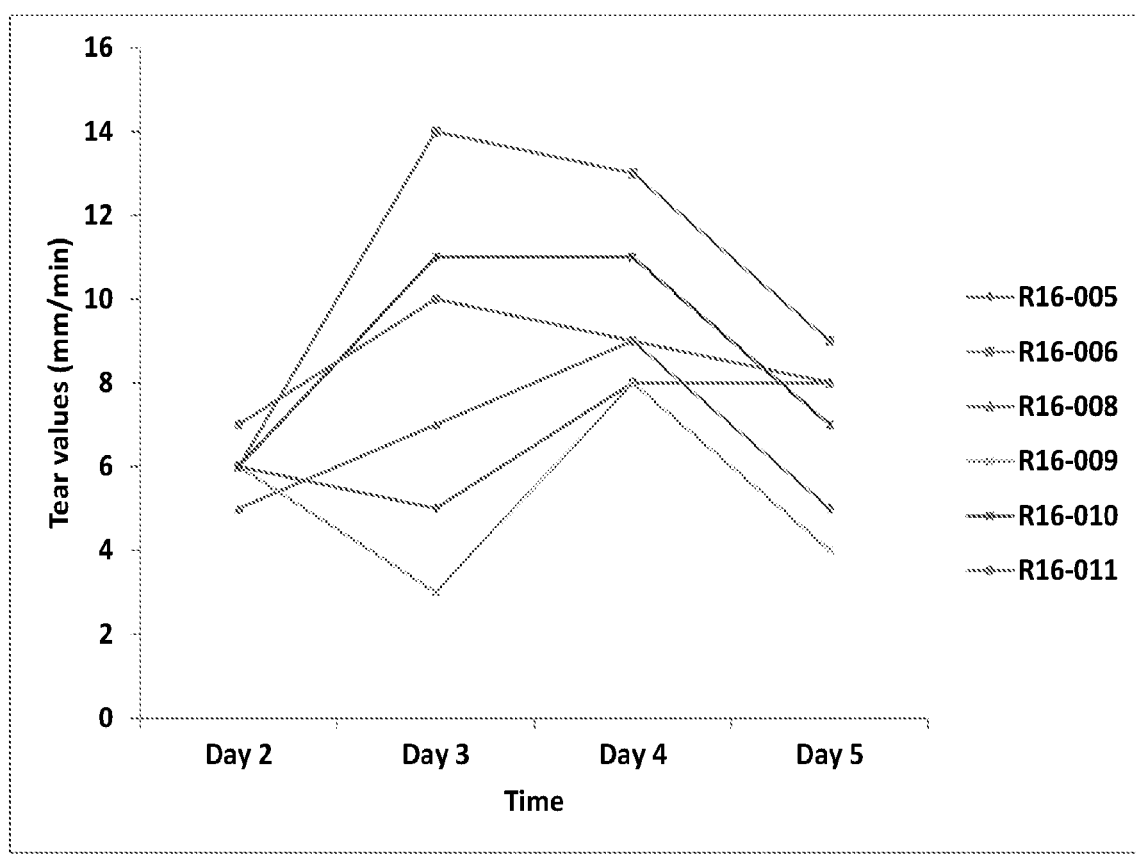

Figs. 21A-D
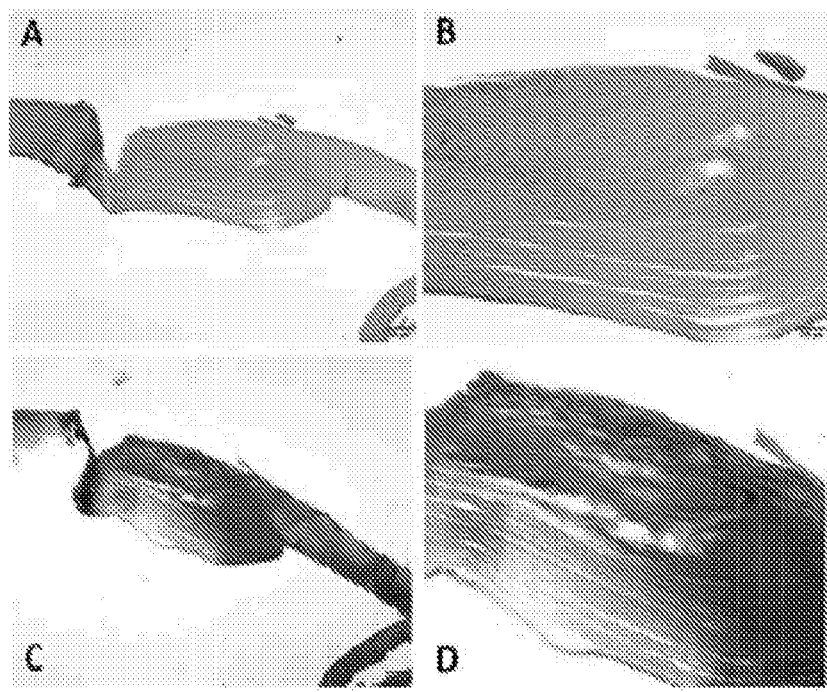
Figs. 22A-D
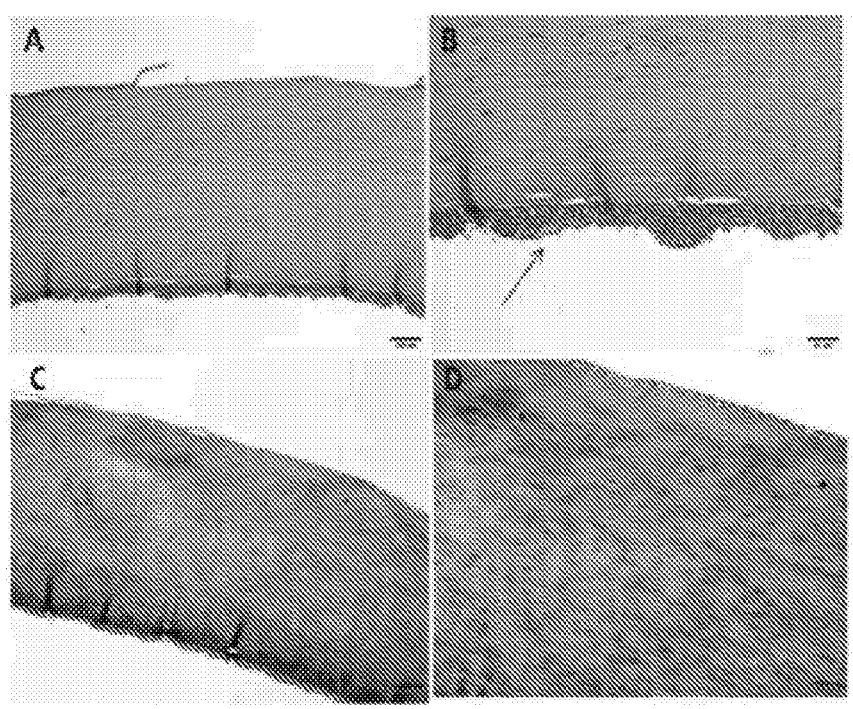

Figs. 23A-D
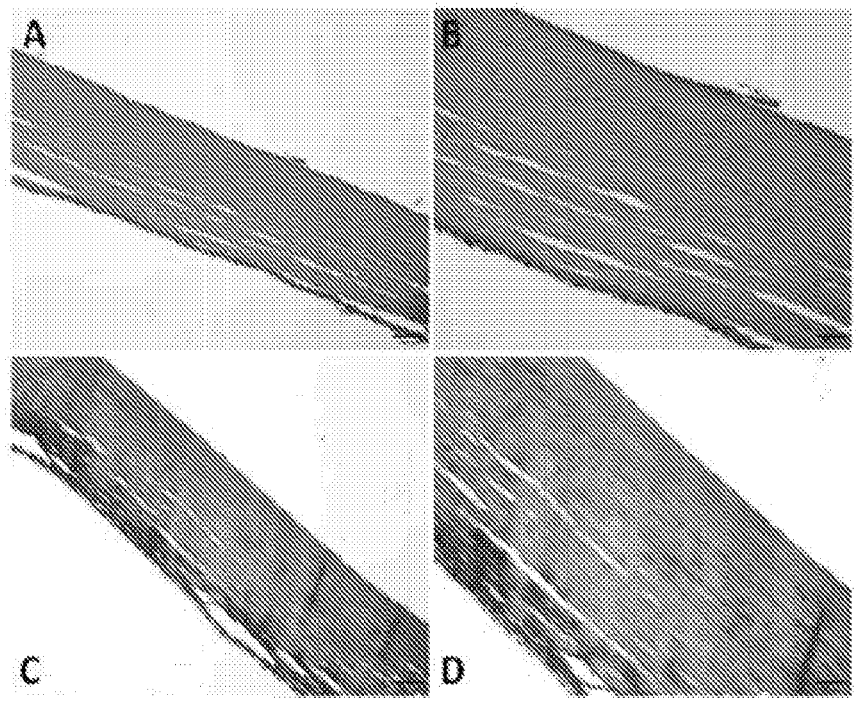
Figs. 24A-D
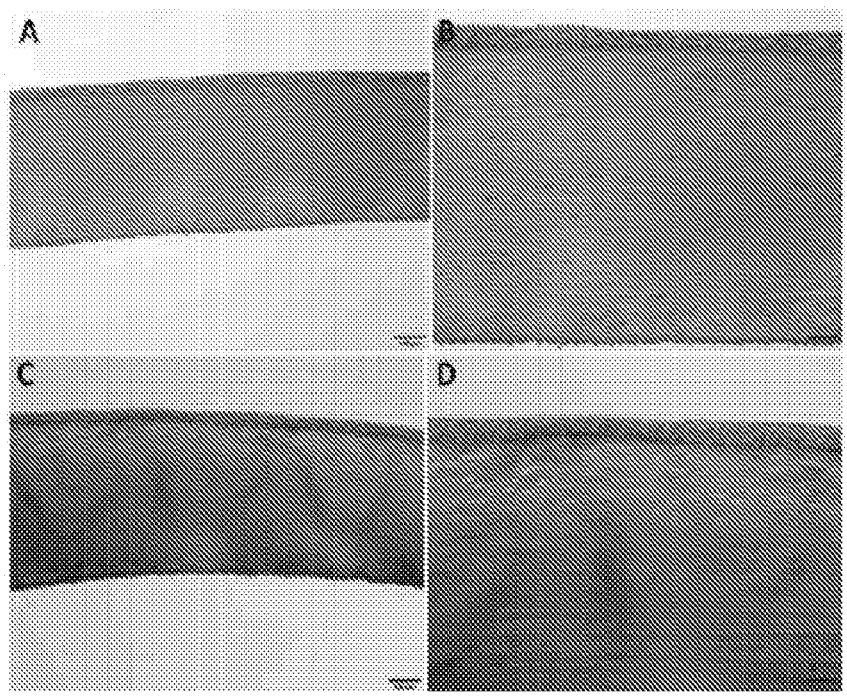

Figs. 25A-F
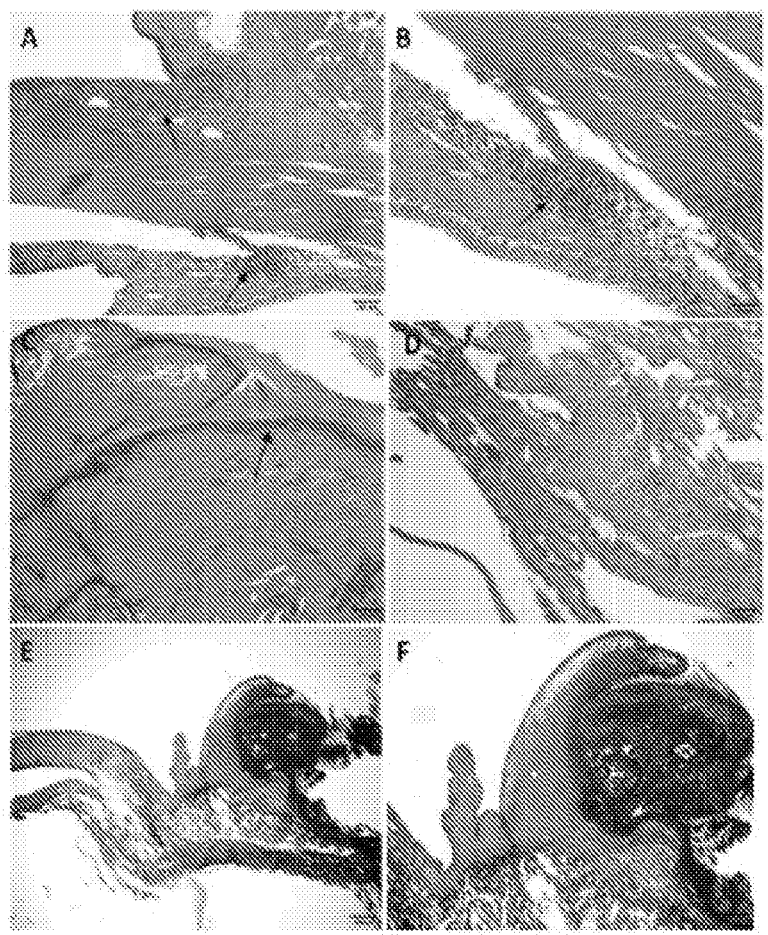

Figs. 26A-F
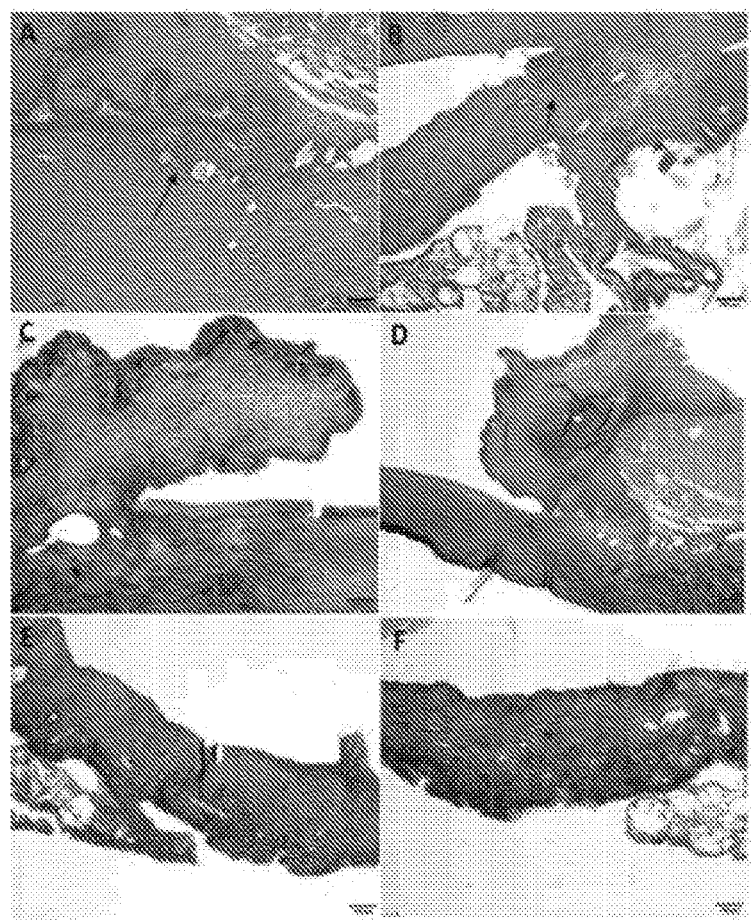
Figs. 27A-D
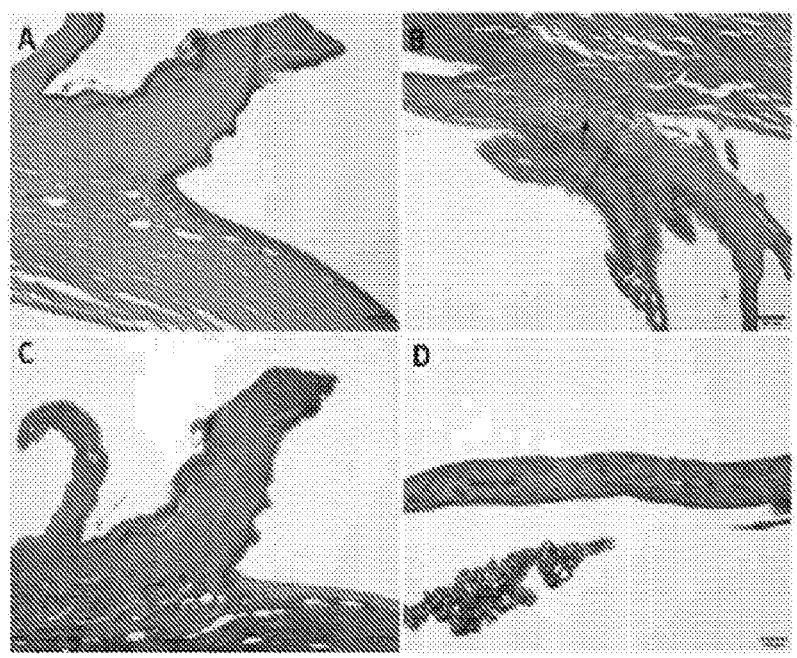

Figs. 28A-D
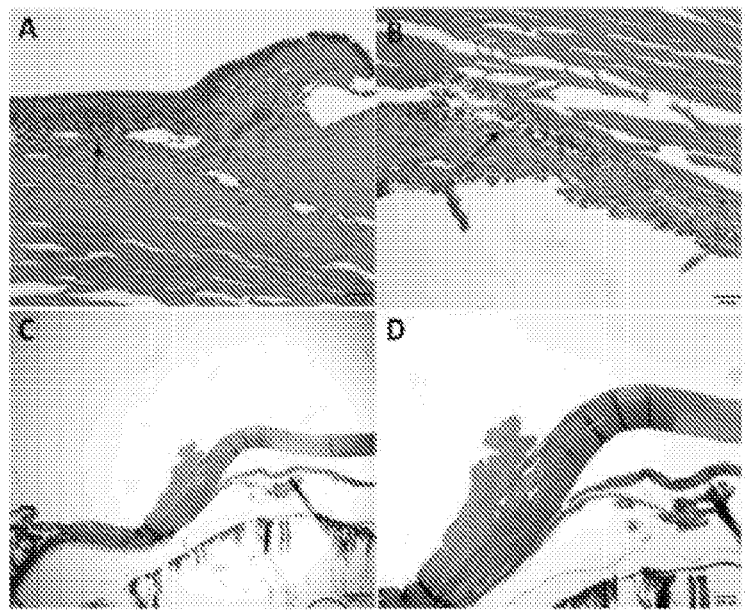
Figs. 29A-D
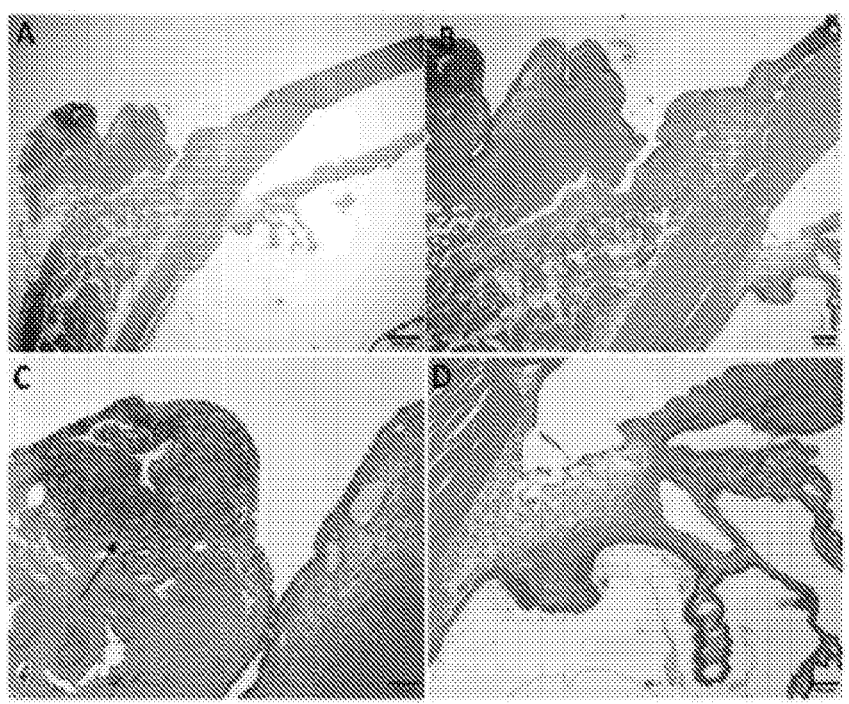

Figs. 30A-D
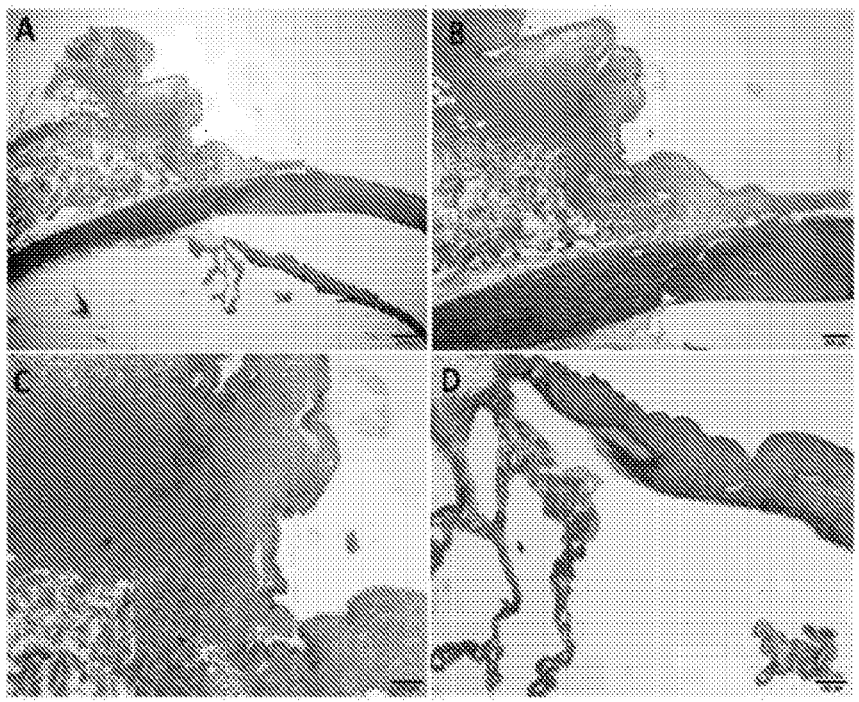
Figs. 31A-D
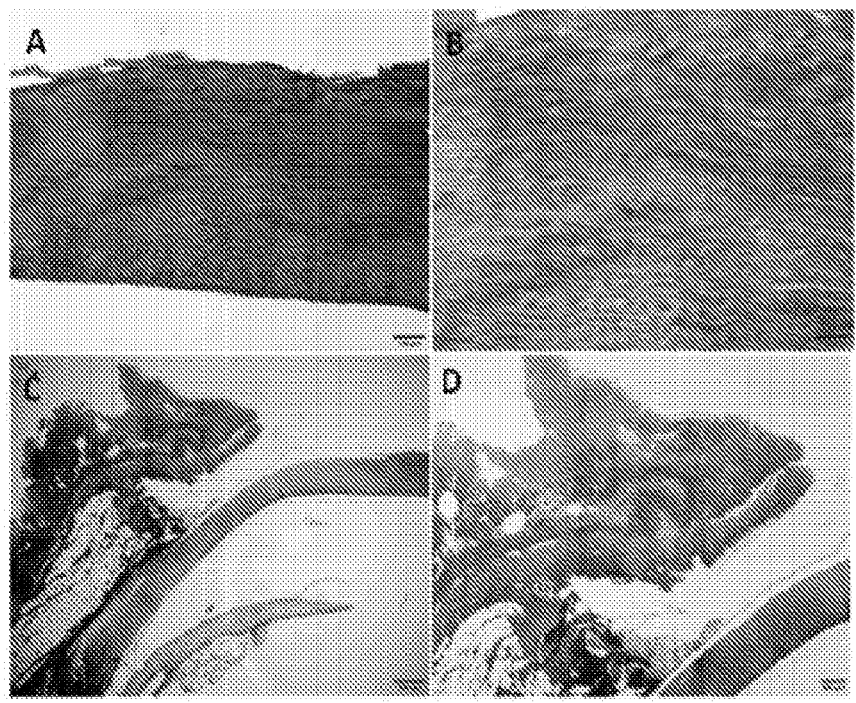

Figs. 32A-B
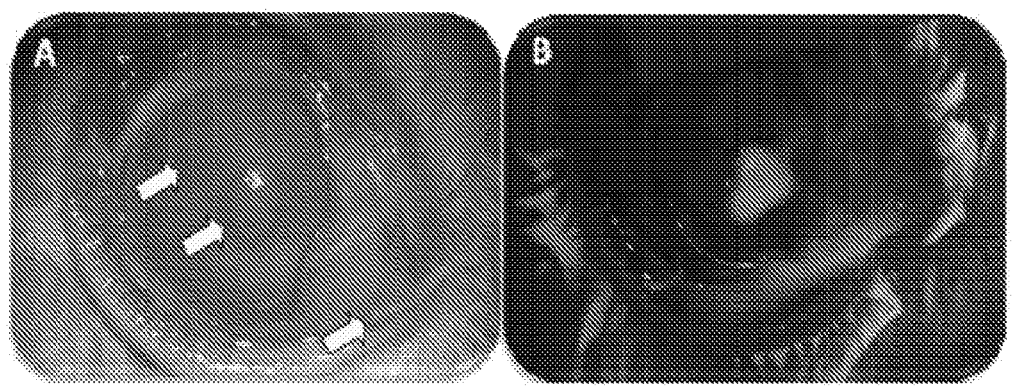
Figs. 33A-B
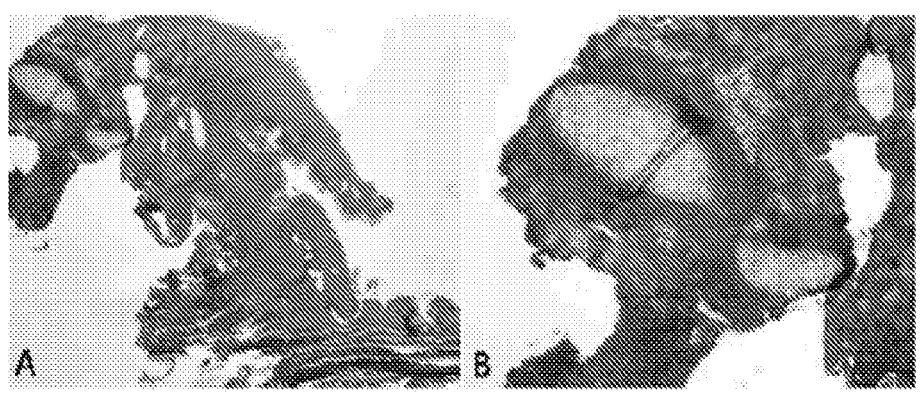

Figs. 34A-F
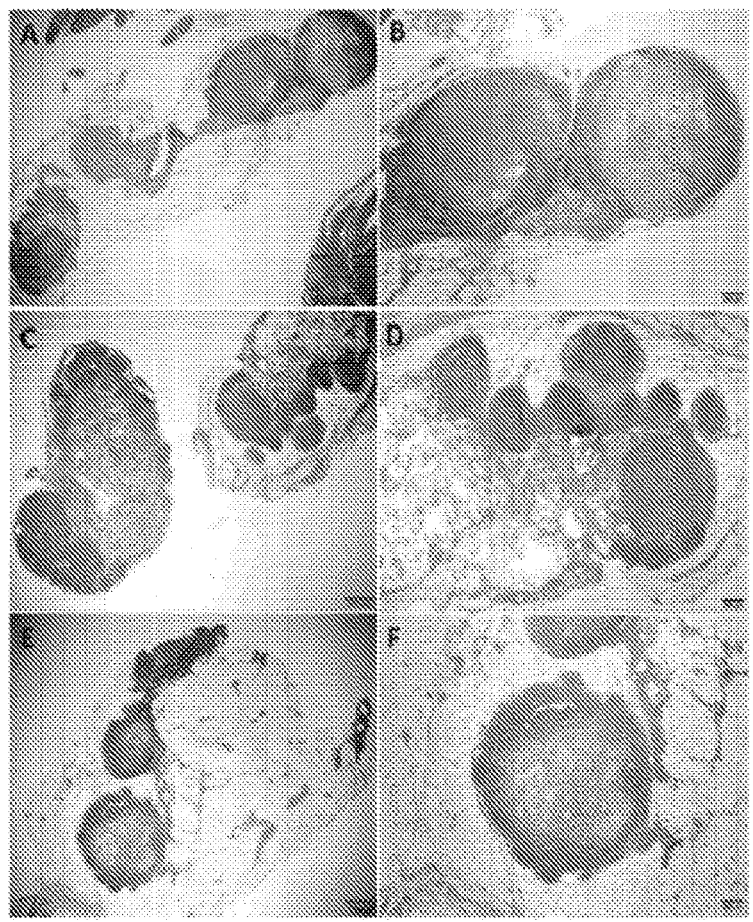
Fig. 35
CONTROL
Mean area: 5.8±3.4 mm²
HIGH DOSE
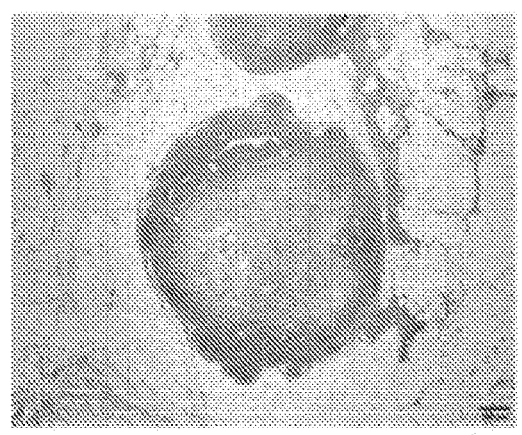
Mean area: 3.5±1.3 mm²

0.5x10⁷ particles 0.5x10⁸ particles 0.5x10⁹ particles

Alkali burn mice, Topical Administration

Healthy mice, Subconjunctival injection

METHODS OF TREATING OCULAR INFLAMMATION AND CHEMICAL INJURIES OF THE EYE WITH EXTRACELLULAR VESICLES

RELATED APPLICATIONS

This application is a U.S. National Stage application filed according to 35 USC § 371 of International Application PCT/US2017/022370, filed Mar. 14, 2017, which claims the benefit of U.S. Provisional Application No. 62/368,972, filed Jul. 29, 2016, and U.S. Provisional Application No. 62/308,166, filed Mar. 14, 2016, the entireties of which are hereby incorporated by reference.

SEQUENCE LISTING

The instant application contains a Sequence Listing which has been submitted electronically in ASCII format and is hereby incorporated by reference in its entirety. Said ASCII copy, created on Sep. 7, 2022, is named 503P2PCTUS_ST25.txt and is 798 bytes in size.

BACKGROUND OF THE INVENTION

Chemical injuries of the eye are ophthalmic emergencies that require immediate evaluation and management. These injuries often result in significant ocular morbidity. Although the most devastating sequelae of chemical injuries—corneal melt, limbal stem cell deficiency, and glaucoma—tend to occur over the long term, effective diagnosis and treatment in the minutes and days following the initial injury often dictate the clinical course and can prevent tragic consequences. Most chemical injuries of the eye occur in young men. At least 90 percent of these injuries are accidental, and they typically take place in industrial settings and often occur despite the use of safety glasses. See, e.g., Hemmati et al., "Treating Acute Chemical Injuries of the Cornea," *Ophthalmic Pearls*: Cornea, EyeNet Magazine, 1-3 (October 2012); Colby, *Focal Points: Clinical Modules for Ophthalmologists*, American Academy of Ophthalmology, the Eye M.D. Association, Vol. XXVIII, Module 1 of 3, 1-14 (March 2010).

Injuries caused by alkali agents are more common and generally more serious than those caused by acids. Alkalis penetrate tissue more readily than acids due to their ability to saponify cell membranes. Strong alkali agents can reach the anterior chamber within 15 seconds of exposure, causing cell death and corneal hydrolysis along the way (including the trabecular meshwork, lens, and ciliary body). Hydroxyl ions, which are common to many alkali chemicals, denature the collagen matrix of the cornea and facilitate further chemical penetration. Affected tissues can undergo liquefactive necrosis, in which the inflammatory response triggers release of proteolytic enzymes, leading to a cascade of damage. Chemicals commonly responsible for alkali injuries of the eye include, e.g., sodium hydroxide (lye; found in drain cleaners and industrial cleaning solutions), ammonia (found in household cleaning solutions and fertilizers), and calcium hydroxide (lime; found in cement and plaster). Direct chemical damage to the conjunctiva can lead to scarring, forniceal shortening, symblepharon formation, and cicatricial ectropion or entropion. Destruction of conjunctival goblet cells can contribute to a lifetime of dry eye. Severe burns to the limbal stem cells may cause limbal stem cell deficiency, resulting in opacification and eventual neovascularization of the cornea due to loss of corneal epithelial progenitor cells. Moreover, glaucoma can arise from injury to the trabecular meshwork, contraction of the anterior structures of the globe, and possibly chemical and inflammatory damage to the ganglion cells in the posterior segment of the eye. Id.

Acid burns are generally less destructive than their alkali counterparts and usually occur with exposure to strong acids that have a pH of less than 4. Hydrochloric acid (used to clean swimming pools) and sulfuric acid (found in car batteries) are some of the more common acids encountered in emergency settings. Acids tend to denature, coagulate, and precipitate corneal proteins on contact, creating a barrier that prevents deeper penetration of the acid. This protein coagulation produces the ground-glass appearance of the cornea often seen in severe acid burns. Hydrofluoric acid (used in antirust solutions and glass etching) is an exception to this: The fluoride ion rapidly penetrates the entire thickness of the cornea through cell membranes, causing significant corneal and anterior segment destruction. Id.

Classification schemes enable the ophthalmologist to determine the severity of the injury and the prognosis for the injured eye. Immediate management consists of copious irrigation following the exposure. Effective management in the intermediate and late phases requires an understanding of the cellular events occurring during each phase. Appropriate medical and surgical care helps ensure the best outcomes for these potentially blinding injuries. Id.

There are three main goals in managing a chemical injury: enhance recovery of the corneal epithelium; augment collagen synthesis while minimizing collagen breakdown and sterile ulceration; and control inflammation. In severe cases, surgical treatment may be indicated. Currently, there remains a need for an effective pharmacologic treatment that would achieve all these 3 main goals of treating chemical burns of the ocular surface. Id.

Allogeneic hematopoietic stem cell transplantation (HSCT) from human leukocyte antigen (HLA)-matched donors is a potentially curative form of treatment for hematologic diseases. Efficacy of allogeneic HSCT depends on the graft-versus-tumor effect which improves engraftment and reduces the risk of relapse. However, allogeneic HSCT has been restricted from widespread use due to graft-versus-host disease (GVHD) which is a major cause of morbidity and mortality in patients receiving allogeneic HSCT. The incidence of GVHD varies 10-90% of patients receiving allogeneic HSCT. Maintaining the graft-versus-tumor effect while dampening GVHD poses a crucial challenge for physicians. The pathogenesis of GVHD is multifactorial. GVHD is an immune-mediated disease that results from complex interactions between donor and recipient adaptive and innate immunity. Donor-derived CD4+ and cos+ T cells are thought to be the primary effector cells in the pathogenesis of GVHD. In GVHD, these donor-derived T cells recognize host antigens—i.e., minor histocompatibility antigens which are not included in routine HLA typing—as foreign.

The incidence of GVHD varies depending on, among other factors, the source of donor tissue, age, female donor to male recipient, underlying disease, intensity of conditioning, and degree of histocompatibility. The targets of the immunologic attack in GVHD are primarily the skin, gastrointestinal system, liver, lung, oral mucosa, and eyes. Ocular GVHD affects 40-60% of patients receiving allo-HSCT, it can occur in patients who have acute or chronic GVHD, and 40-90% of patients with chronic GVHD will develop ocular symptoms. Ocular GVHD may affect the ocular surface and lacrimal glands through inflammation and cicatricial scarring or dysfunction of the meibomian glands. The symptoms of ocular GVHD can include moderate to severe keratoconjuncitvitis sicca, bilateral marginal keratitis, anterior uveitis, corneal ulceration, and/or neovascularization. See, e.g., Hasanain Shikari et al., "Ocular Graft-versus-Host Disease: A Review," *Survey of Ophthalmology*, Vol. 58, No. 3 (May-June 2013), the disclosures of which are herein incorporated by reference in their entirety.

There are no approved pharmaceutical products on the market for treatment of ocular GVHD, and there remains a need for an effective pharmacologic treatment for ocular inflammation, in particular ocular GVHD. The present invention fulfills this need in the art.

Dry eye disease (DED) is a manifestation of chronic inflammatory processes in the cornea, conjunctiva, and lacrimal glands (LG). Current standards of care involve topical drug administration that target specific inflammatory pathways, but they fail in many DED patients, and new therapeutic paradigms are urgently needed.

Cells release into the extracellular environment diverse types of membrane vesicles of endosomal and plasma membrane origin called exosomes and microvesicles, respectively. These extracellular vesicles represent an important mode of intercellular communication by serving as vehicles for transfer between cells of membrane and cytosolic proteins, lipids, and RNA See, e.g., Gra9a Raposo and Willem Stoorvogel, "Extracellular Vesicles: Exosomes, Microvesicles, and Friends," *The Journal of Cell Biology*, Vol. 200, No. 4, 373-383 (2013). WO 2014/028493 describes exosomes derived cardiosphere-derived cells (CDCs) and their therapeutic utility for the repair or regeneration of damaged or diseased cells or tissue, e.g., damaged cardiac tissue. US 2012/0315252 in turn describes CDCs, their derivation from cardiospheres, and their therapeutic utility for increasing the function of a damaged or diseased heart of a mammal. WO 2005/012510 in turn describes cardiospheres, their derivation from human or animal cardiac tissue biopsy samples, and their therapeutic utility in cell transplantation and functional repair of the myocardium or other organs.

SUMMARY OF THE INVENTION

The present invention is based on the surprising discovery by the present inventors that extracellular vesicles, in particular exosomes derived from cardiosphere-derived cells (CDCs), would be effective in treating a chemical injury of the eye, in particular alkali burn of the cornea, as well as ocular GVHD and similar inflammatory ocular conditions. Since there was no recognition whatsoever in the art as to the potential therapeutic utility of extracellular vesicles to treat a chemical injury of the eye, in particular alkali burn of the cornea, as well as ocular GVHD and similar inflammatory ocular conditions, the present invention is based on the demonstration in relevant animal model experiments that unexpectedly showed that exosomes derived from CDCs are safe and efficacious in treating a subject with an alkali burn of the cornea, as well as ocular GVHD and similar inflammatory ocular conditions, as described herein.

A first aspect of the present invention provides a method of treating a chemical injury of the eye, in particular a chemical injury of the cornea, the anterior chamber (including the trabecular meshwork, lens, and ciliary body), the conjunctiva, the limbus, or the sclera, in a subject in need thereof, the method comprising administrating to the eye of the subject a therapeutically effective amount of extracellular vesicles, in particular exosomes derived from CDCs. In several embodiments, the subject is a mammal, and preferably a human. In a preferred embodiment of the present invention, the chemical injury of the eye is an alkali burn injury of the cornea.

A second aspect of the present invention provides a formulation comprising extracellular vesicles for use in the treatment of a chemical injury of the eye, in particular a chemical injury of the cornea, the anterior chamber (including the trabecular meshwork, lens, and ciliary body), the conjunctiva, the limbus, or the sclera.

In some embodiments, the chemical injury of the eye is a chemical burn, in particular an acid burn caused by exposure to an acid agent having a pH of less than 6, 5, 4, 3, or 2, or an alkali burn caused by exposure to an alkali agent having a pH of greater than 8, 9, 10, 11, 12, or 13, wherein said acid agent is hydrochloric acid (HCl), hydrofluoric acid (HF), acetic acid (CH3CO2H), sulfuric acid (H2SO4), or sulfurous acid (H2SO3), and wherein said alkali agent is ammonia (NH3), sodium hydroxide (NaOH), potassium hydroxide (KOH), magnesium hydroxide (Mg(OH)2), lye, or lime.

In additional embodiments, chemical injuries of the eye are caused by exposure to chemical agents due to accident or hostile activity (e.g. terrorism or conventional warfare).

A third aspect of the present invention provides a method for treating an ocular inflammation in a subject in need thereof, the method comprising administrating to the eye of the subject a therapeutically effective amount of extracellular vesicles. The invention encompasses formulations of extracellular vesicles for use in treating a patient with an ocular inflammation. The invention encompasses uses of formulations of extracellular vesicles for treating a patient with an ocular inflammation. In some embodiments, the administration is via topical administration or subconjunctival injection. In some embodiments, the ocular inflammation is an inflammation of the cornea including corneal edema, keratitis including keratoconjunctivitis sicca (KCS) (also called dry eye syndrome (DES) or keratitis sicca), ocular GVHD (particularly where the patient has undergone allogenic HSCT), uveitis, scleritis, blepharitis, iritis, pars planitis, vitritis, iridocyclitis, chorioretinitis, Sjogren's syndrome, post-surgical ocular inflammation, ocular disorders associated with Stevens-Johnson syndrome, or ocular pemphigus or ocular cicatricial pemphigoid.

In some embodiments, the extracellular vesicle is an exosome, microvesicle, membrane particle, membrane vesicle, exosome-like vesicle, ectosome, ectosome-like vesicle, exovesicle, epididimosome, argosome, promininosome, prostasome, dexosome, texosome, archeosome, oncosome, or the like.

In several embodiments, said administration is via subcutaneous injection, transcutaneous injection, intradermal injection, topical administration (e.g., in the form of eye drops), intramuscular injection, injection into lymphoid tissue, injection into the lymphatic system, systemic administration (e.g., oral, intravenous, intraparenteral), or the like.

In several embodiments, extracellular vesicles, e.g., exosomes, are formulated in a crystalloid solution (e.g., Plasmalyte, normal saline), aqueous solution, gel, ointment, cream, topical or implantable hydrogel, powder, spray, sustained-release polymer (e.g., PLGA and PLA), polyethylene glycol (PEG)-containing solution, suspension, emulsion, as part of a drug delivery device, insert, patch, or the like. In several embodiments, prior to use, extracellular vesicles, e.g., exosomes, are resuspended in an appropriate buffer, e.g., sterile PBS with or without human serum albumin. In some embodiments, exosomes can be stored for future use, e.g., frozen at −80° C.

In several embodiments, extracellular vesicles, e.g., exosomes, are derived from human or animal cells. In several embodiments, extracellular vesicles, e.g., exosomes, are prepared from cardiospheres or CDCs. In some embodiments, extracellular vesicles, e.g., exosomes, are prepared from regenerative stem cells such as embryonic stem cells, pluripotent stem cells, multipotent stem cells, induced pluripotent stem cells, post-natal stem cells, adult stem cells, mesenchymal stem cells, hematopoietic stem cells, endothelial stem cells, epithelial stem cells, neural stem cells, cardiac stem cells including cardiac progenitor cells, bone marrow-derived stem cells, adipose-derived stem cells, hepatic stem cells, peripheral blood derived stem cells, cord blood-derived stem cells, placental stem cells, or the like.

In several embodiments, extracellular vesicles, e.g., exosomes, are modified (e.g., genetically or otherwise) to direct them to a specific target site. For example, a modification may, in some embodiments, comprise inducing expression of a specific cell-surface marker on the exosome, which results in specific interaction with a receptor on a desired target tissue. In one embodiment, the native contents of the exosome are removed and replaced with, or supplemented with, desired exogenous proteins and/or nucleic acids.

In several embodiments, extracellular vesicles, e.g., exosomes, include one or more microRNAs selected from: miR-146a, miR-148a, miR-22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a. In a preferred embodiment, extracellular vesicles, e.g., exosomes, comprise miR-146a and miR-210. In several embodiments, extracellular vesicles, e.g., exosomes, include one or more microRNAs selected from: hsa-miR-23a-3p, hsa-miR-130a-3p, hsa-miR-21-Sp, hsa-miR-4516, hsa-let-7a-Sp, hsa-miR-125b-5p, hsa-miR-199a-3p, hsa-miR-199b-3p, hsa-miR-22-3p, hsa-miR-24-3p, hsa-miR-1290, hsa-miR-320e, hsa-miR-423-Sp, hsa-miR-22-3p, hsa-miR-222-3p (also known as miR-221-3p), hsa-miR-100-Sp, hsa-miR-337-Sp, hsa-miR-27b-3p, hsa-miR-1915-3p, and hsa-miR-29b-3p, hsa-miR-25-3p (also known as miR-92a-3p).

In several embodiments, extracellular vesicles, e.g., exosomes, contain biological proteins, e.g., transcription factors, cytokines, growth factors, and similar proteins capable of modulating signaling pathways in a target cell. In some embodiments, the biological protein is capable of facilitating regeneration and/or improved function of a tissue. In some embodiments, the biological protein is capable of modulating pathways related to Irakl, Traf6, toll-like receptor (TLR) signaling pathway, NOX-4, SMAD-4, and/or TGF-p. In some embodiments, the biological protein is related to exosome formation and packaging of cytosolic proteins such as Hsp70, Hsp90, 14-3-3 epsilon, PKM2, GW182 and AGO2. In some embodiments, extracellular vesicles, e.g., exosomes, contain signaling lipids, e.g., ceramide and derivatives.

In several embodiments, extracellular vesicles, e.g., exosomes, express tetraspanins, e.g., CD63, CD81, CD82, CD53, and/or CD37. In some embodiments, extracellular vesicles, e.g., exosomes, express one or more lipid raft associated proteins (e.g., glycosylphosphatidylinositol-anchored proteins and flotillin), cholesterol, sphingomyelin, and/or hexosylceramides.

In several embodiments, extracellular vesicles, e.g., exosomes, have a diameter of, e.g., about 15-250 nm, about 15-205 nm, about 90-220 nm, about 30-200 nm, about 20-150 nm, about 70-150 nm, or about 40-100 nm In several embodiments, extracellular vesicles, e.g., microvesicles, have a diameter of, e.g., about 100-1000 nm In several embodiments, extracellular vesicles, e.g., exosomes, are purified such that contaminants or undesired compounds are removed from the exosomes. In some embodiments, the patient is administered substantially purified exosomes such that about 50% to 90%, or up to 100%, of the contaminants are removed from the exosomes. In some embodiments, an exosome preparation is essentially free of non-exosome components.

In several embodiments, extracellular vesicles, e.g., exosomes, are administered in combination with one or more additional agents. For example, in several embodiments, the exosomes are administered in combination with one or more proteins or nucleic acids derived from the exosome. In several embodiments, the cells from which the exosomes are isolated are administered in conjunction with the exosomes. In several embodiments, such an approach advantageously provides an acute and more prolonged duration of exosome delivery (e.g., acute based on the actual exosome delivery and prolonged based on the cellular delivery, the cells continuing to secrete exosomes post-delivery).

In several embodiments, the dose of extracellular vesicles, e.g., exosomes ranges about $1.0 \times 10^5$ to about $1.0 \times 10^9$ exosomes. In certain embodiments, the exosome dose is administered on a per kilogram basis, e.g., about $1.0 \times 10^5$ exosomes/kg to about $1.0 \times 10^9$ exosomes/kg. In additional embodiments, exosomes are delivered in an amount based on the mass of the target tissue, e.g., about $1.0 \times 10^5$ exosomes/gram of target tissue to about $1.0 \times 10^9$ exosomes/gram of target tissue. In several embodiments, exosomes are administered based on a ratio of the number of exosomes to the number of cells in a particular target tissue. If exosomes are to be administered in conjunction with the concurrent therapy (e.g., cells that can still shed exosomes, pharmaceutical therapy, nucleic acid therapy, and the like) the dose of exosomes administered can be adjusted accordingly (e.g., increased or decreased as needed to achieve the desired therapeutic effect).

BRIEF DESCRIPTION OF THE DRAWINGS

FIG. 1A is a photograph showing the eye of the Sprague-Dawley rat used to generate the alkali burn model.

FIG. 1B is a photograph showing the placement of a filter paper soaked with sodium hydroxide to induce alkali burn in the eye relative to FIG. 1A.

FIG. 1C is a diagram showing how the alkali burn is induced in the eye relative to FIG. 1B.

FIGS. 13A-B graphically show the mean Schirmer Tear Test-I (STT-I) scores after adoptive transfer by IV injection of autologous, MCR-activated peripheral blood lymphocytes and two subconjunctival treatments with CDC-EVs (OD eyes) and vehicle (OS eyes). The mean STT-I increase reached statistical significance in OD (P=0.046) but not in OS (P=0.100).

FIG. 14A shows blepharitis, chemosis and ocular dense exudate (arrows).

FIG. 14B shows details of the congested palpebral conjunctiva vessels (arrow).

FIG. 15A shows a representative corneal ulcer image prior to subconjunctival injection of exosomes to Group A (vehicle control) animals (Day 2, fluorescein staining).

FIG. 15B shows a representative corneal ulcer image prior to subconjunctival injection of extracellular exosomes to Group B (low-dose exosomes) animals (Day 2, fluorescein staining).

FIG. 15C shows a representative corneal ulcer image prior to subconjunctival injection of extracellular exosomes to Group C (high-dose exosomes) animals (Day 2, fluorescein staining).

FIG. 16A shows tear production evolution in Group A (vehicle control) animals.

FIGS. 21A-B show detachment of corneal epithelial cells, fibrosis and mild infiltrate of inflammatory cells in the stroma for Rabbit #005 in Group A (vehicle control).

FIGS. 21C-D show details of fibrosis in the stroma for Rabbit #005 in Group A (vehicle control) (MTC staining).

FIGS. 22A-B show moderate inflammatory infiltrate in the Descemet membrane (arrow) for Rabbit #004 in Group B (low-dose exosomes).

FIGS. 22C-D show detachment of corneal epithelial cells for Rabbit #004 in Group B (low-dose exosomes) (MTC staining).

FIGS. 23A-B show moderate detachment of corneal epithelial cells and slight inflammatory cell infiltrate for Rabbit #037 in Group C (high-dose exosomes).

FIGS. 23C-D show detachment of corneal epithelial cells for Rabbit #037 in Group C (high-dose exosomes) (MTC staining).

FIGS. 24A-B show no histological lesions in the cornea for Rabbit #040 in Group C (high-dose exosomes) (HE staining).

FIGS. 24C-D show no histological lesions in the cornea for Rabbit #040 in Group C (high-dose exosomes) (MTC staining).

FIGS. 25A-B, in the iridocorneal angle, show mild inflammatory cell infiltrate in the bulbar conjunctiva and ciliary bodies (arrows) for Rabbit #005 in Group A (vehicle control) (HE staining).

FIG. 25C shows, in the bulbar conjunctive, mild infiltrate of inflammatory cells (arrow) and severe fibrosis for Rabbit #011 in Group A (vehicle control) (HE staining).

FIG. 25D shows, in the ciliary bodies, mild edema and slight infiltrate of inflammatory cells for Rabbit #011 in Group A (vehicle control) (HE staining).

FIGS. 25E-F show severe fibrosis in the bulbar conjunctiva and ciliary bodies for Rabbit #011 in Group A (vehicle control) (MTC staining).

FIG. 26A shows, in the bulbar conjunctive, moderate fibrosis and mild infiltrate of inflammatory cells (arrow) for Rabbit #004 in Group B (low-dose exosomes) (HE staining).

FIG. 26B shows, in the ciliary bodies, mild infiltrate of inflammatory cells (arrow) and fibrosis for Rabbit #004 in Group B (low-dose exosomes) (HE staining).

FIGS. 26C-D show, in the bulbar conjunctive, moderate fibrosis especially in the angle injected for Rabbit #004 in Group B (low-dose exosomes) (MTC staining).

FIGS. 26E-F show, in the ciliary bodies, mild fibrosis for Rabbit #004 in Group B (low-dose exosomes) (MTC staining).

FIG. 27A shows, in the bulbar conjunctive, no histological lesions for Rabbit #036 in Group B (low-dose exosomes) (HE staining).

FIG. 27B shows, in the ciliary bodies, minimal infiltrate of inflammatory cells (arrow) for Rabbit #036 in Group B (low-dose exosomes) (HE staining).

FIG. 27C shows the bulbar conjunctive for Rabbit #036 in Group B (low-dose exosomes) (MTC staining).

FIG. 27D shows, in the ciliary bodies, fibrosis was not present for Rabbit #036 in Group B (low-dose exosomes) (MTC staining).

FIG. 28A shows, in the bulbar conjunctive, minimal infiltrate of inflammatory cells (arrow) for Rabbit #037 in Group C (high-dose exosomes) (HE staining).

FIG. 28B shows, in the ciliary bodies, minimal infiltrate of inflammatory cells (arrow) for Rabbit #037 in Group C (high-dose exosomes) (HE staining).

FIGS. 28C-D show the iridocorneal angle without fibrosis for Rabbit #037 in Group C (high-dose exosomes) (MTC staining).

FIGS. 29A-B show moderate fibrosis, edema and inflammatory cell infiltrate in the bulbar conjunctiva for Rabbit #040 in Group C (high-dose exosomes) (HE staining).

FIG. 29C shows, in the bulbar conjunctive, moderate infiltrate of inflammatory cells (arrow) for Rabbit #040 in Group C (high-dose exosomes) (HE staining).

FIG. 29D shows minimal edema in the ciliary bodies for Rabbit #040 in Group C (high-dose exosomes) (HE staining).

FIGS. 30A-B show moderate fibrosis in the bulbar conjunctiva for Rabbit #040 in Group C (high-dose exosomes) (MTC staining).

FIG. 30C shows moderate fibrosis in the bulbar conjunctiva for Rabbit #040 in Group C (high-dose exosomes) (MTC staining).

FIG. 30D shows the ciliary bodies without fibrosis for Rabbit #040 in Group C (high-dose exosomes) (MTC staining).

FIGS. 31A-B show focal fibrosis with disruption of structures in the cornea for Rabbit #041 in Group C (high-dose exosomes) (MTC staining).

FIGS. 31C-D show severe fibrosis in the iridocorneal angle for Rabbit #041 in Group C (high-dose exosomes) (MTC staining).

FIG. 32A shows iris vessel congestion, corneal edema and exudate in the right eye for Rabbit #041 in Group C (high-dose exosomes).

FIG. 32B shows defined corneal ulcer with fluorescein staining in the right eye for Rabbit #041 in Group C (high-dose exosomes).

FIG. 33A shows the bulbar conjunctiva for Rabbit #039 in Group C (high-dose exosomes).

FIG. 33B shows cartilaginous metaplasia for Rabbit #039 in Group C (high-dose exosomes).

FIGS. 34A-B show the parotid lymph node for Rabbit #010 in Group A (vehicle control) (HE staining).

FIGS. 34C-D show the parotid lymph node for Rabbit #003 in Group B (low-dose exosomes) (HE staining).

FIGS. 34E-F show the parotid lymph node for Rabbit #034 in Group C (high-dose exosomes) (HE staining).

FIG. 35 shows that the rabbits treated with the high-dose exosomes showed a smaller area (3.5±1.3 mm$^2$) of lymphoid tissue in parotid lymph node than animals treated with vehicle (5.8±3.4 mm$^2$), suggesting a reduced immune reaction in those nodes.

DETAILED DESCRIPTION OF THE INVENTION

A) Clinical Manifestations

Figure 2:
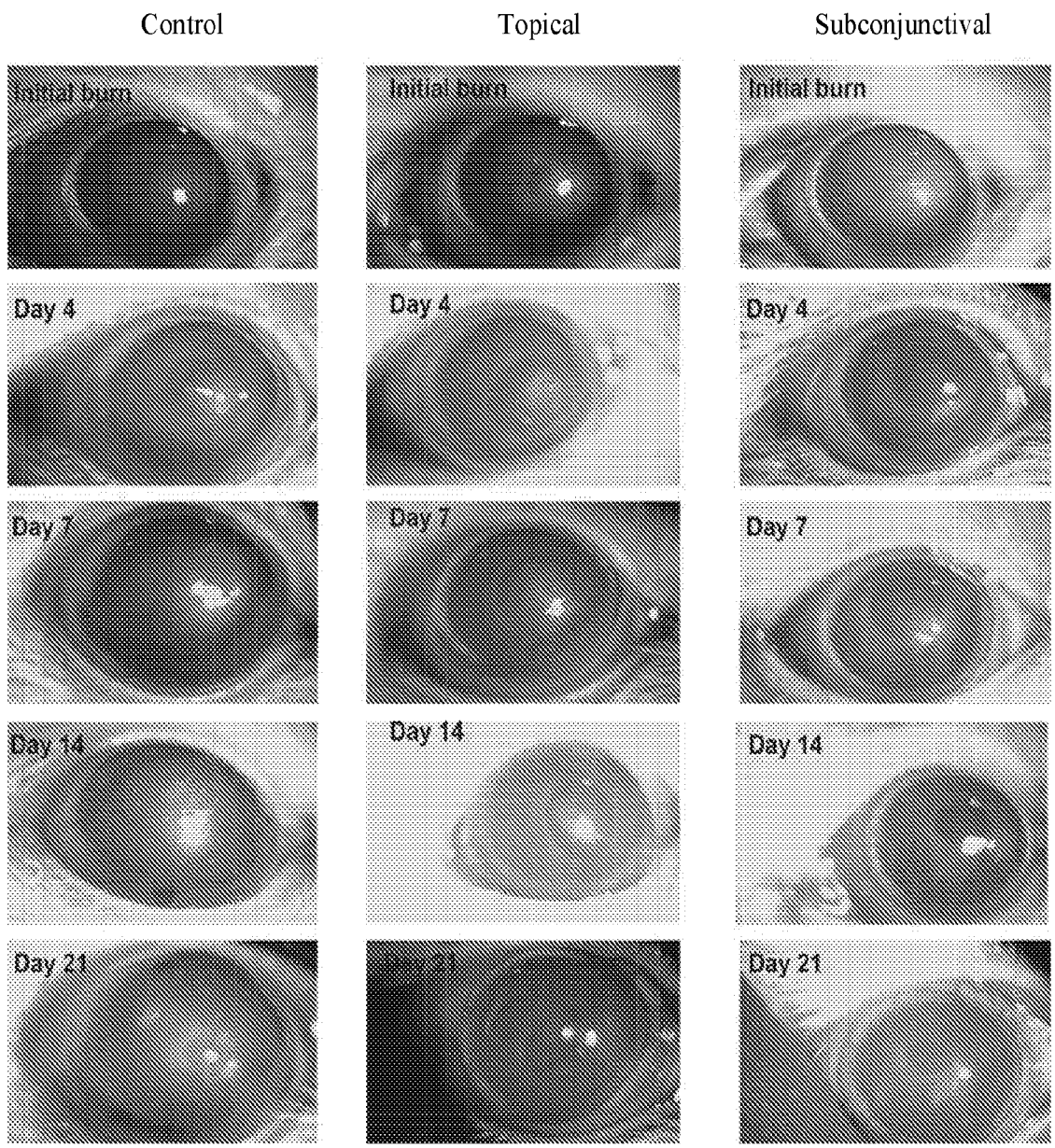
FIG. 2 are photographs showing the effects of topical and subconjunctival administration of exosomes relative to the control group over 21 days.

Numerous classification schemes exist to describe chemical injuries of the eye. The common factor among the various schemes is a clinical determination of the extent of conjunctival, limbal, and corneal (epithelial and stromal) damage at the time of initial assessment. Key factors, including presence and degree of limbal ischemia and corneal haze, are used to classify the injury. The Hughes classification scheme, as modified by Thof, divides chemical injuries into four categories in order of worsening severity, as summarized in Table 1.

TABLE 1

| Grade 1 | Grade 2 | Grade 3 | Grade 4 |
|---|---|---|---|
| Corneal epithelial defect; No corneal haze; No loss of limbal stem cells | Cornea mildly hazy; Focal limbal ischemia | Severe corneal haze limits view of anterior segment structures; Extensive limbal ischemia with loss of most limbal stem cells | Complete loss of corneal and proximal conjunctival Epithelium; Cornea opaque; Complete limbal ischemia and loss of all limbal stem cells |

Grade I injuries involve the corneal epithelium only, and the limbal stem cells, which serve as the source of differentiated corneal epithelium, are spared. The cornea, although denuded of epithelium, remains clear. There is no limbal ischemia. Grade II injuries are characterized by a partial loss of the limbal stem cells with focal limbal ischemia. The cornea is hazy, but anterior segment structures (iris, lens) can still be visualized. Grade III injuries are characterized by significant ischemia of most of the limbus, as well as profound corneal haze that limits the view of anterior chamber structures. Due to extensive limbal stem cell loss, patients with Grade III injuries have a guarded prognosis. Following Grade III injuries, resurfacing of the cornea can only be accomplished by growth of conjunctival epithelium over the corneal stroma. Improvement in vision is often not achieved without a surgical procedure. Grade IV injuries are characterized by complete loss of corneal epithelium and limbal stem cells plus loss of the proximal conjunctival epithelium. The injured cornea is opaque, allowing no view into the anterior chamber. More than 50% of the limbus is ischemic. With no endogenous source of epithelium to repopulate the corneal surface, sterile ulceration is a common sequela of Grade IV injuries despite aggressive medical and surgical management.

For the purpose of the present invention, terms such as "treating" as used herein refer to therapeutic measures that cure, slow down, lessen symptoms of, and/or halt progression of a diagnosed pathologic condition or disorder. For instance, a subject is successfully "treated" according to the methods of the present invention if the subject shows clinical improvement according to the Hughes classification scheme, as modified by Thof.

B) Cardiospheres

Cardiospheres are undifferentiated cardiac cells that grow as self-adherent clusters as described in WO 2005/012510, and Messina et al., "Isolation and Expansion of Adult Cardiac Stem Cells From Human and Murine Heart," Circulation Research, 95:911-921 (2004), the disclosures of which are herein incorporated by reference in their entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal or ventricle wall, atrial appendages, or combinations thereof. A biopsy can be obtained, e.g., by using a percutaneous bioptome as described in, e.g., U.S. Patent Application Publication Nos. 2009/012422 and 2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like. The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium comprising buffered media, amino acids, nutrients, serum or serum replacement, growth factors including but not limited to EGF and bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated.

C) Cardiosphere-Derived Cells (CDCs)

CDCs are a population of cells generated by manipulating cardiospheres in the manner as described in, e.g., U.S. Patent Application Publication No. 2012/0315252, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods.

D) Exosomes

Exosomes are vesicles formed via a specific intracellular pathway involving multivesicular bodies or endosomal-related regions of the plasma membrane of a cell.

Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, as described in WO 2014/028493, miR146a exhibits over a 250-fold increased expression in CDCs, and miR210 is upregulated approximately 30-fold, as compared to the exosomes isolated from normal human dermal fibroblasts.

Exosomes derived from cardiospheres and CDCs are described in, e.g., WO 2014/028493, the disclosures of which are herein incorporated by reference in their entirety. Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and U.S. Application Publication Nos. 2012/0093885 and 2014/0004601. Methods for isolating exosome from cardiosphere-derived cells are found in, e.g., Ibrahim et al., Stem Cell Reports, 2:606-619 (2014). Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatant of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm Differences in flotation velocity further allows for separation of differentially sized exosomes. In general, exosome sizes will possess a diameter ranging from 30-200 nm, including sizes of 40-100 nm Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. IPLC can also be used to purify exosomes to homogeneously sized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

(E) EXAMPLES

The present invention is further described with reference to the following non-limiting examples.

Example 1: CDC Culture

CDCs were prepared as described in U.S. Patent Application Publication No. 2012/0315252, the disclosures of which are herein incorporated by reference in their entirety.

In brief, heart biopsies were minced into small fragments and briefly digested with collagenase. Explants were then cultured on 20 mg/mL fibronectin-coated dishes. Stromal-like flat cells and phase-bright round cells grew out spontaneously from tissue fragments and reached confluency by 2-3 weeks. These cells were harvested using 0.25% trypsin and were cultured in suspension on 20 mg/mL poly-d-lysine to form self-aggregating cardiospheres. CDCs were obtained by plating and expanding the cardiospheres on a fibronectin-coated flask as an adherent monolayer culture. All cultures were maintained at 5% O2, 5% CO2 at 37° C., using IMDM basic medium supplemented with 10% FBS, 1% penicillin/streptomycin, and 0.1 mL 2-mercaptoethanol. CDCs were grown to 100% confluency on a fibronectin-coated flask to passage 5.

Example 2: Isolation of Exosomes from CDCs

When the CDCs reached the desired confluency, the flask was washed three times with PBS. CDCs were treated with serum-free medium (IMDM) and were incubated at 37° C. at 5% O2, 5% CO2 for 15 days. After 15 days, the conditioned medium was collected in 225 mL BD Falcon polypropylene conical tubes (BD 352075—Blue Top) and centrifuged at 2,000 rpm for 20 minutes at 4° C. to remove cells and debris (care was taken not to disturb the pellet). The conditioned medium was run through a 0.45p m membrane filter. The conditioned medium was concentrated using centrifugal filter. A 3KDa Centricon Plus-70 Centrifugal Filter was pre-rinsed with 10-25 mL of molecular grade water and was centrifuged at 3220 g for five minutes at 18° C. Once the filter was rinsed, all remaining water was carefully removed without touching the filter. 15 mL of the conditioned medium was added to the filter and was centrifuged at 3220 g for 45 minutes at 18° C. After the initial spin, the remaining medium was mixed by pipetting and then spun again until the desired concentration was reached. The final sample was then run through a 0.22 µm syringe filter. 25 µL of the concentrated conditioned medium was diluted in 975 µL of PBS for particle count using the Nanosight. Another 100 µL of the concentrated conditioned medium was used to measure protein concentration. Protein was quantified using the DC protein Assay. In some cases, historical data was used to calculate the concentration of protein in the ultra-filtration by centrifugation (UFC) sample. The concentrated conditioned medium was used immediately or was stored at −80° C.

Example 3: Exosome Precipitation with 25% Polyethylene Glycol (PEG)

The appropriate volume of 25% PEG was added to the filtered concentrated conditioned medium The samples were incubated at 4° C. for 12-16 hours on an orbital shaker. Once incubation was complete, the samples were centrifuged at 1500 g for 30 minutes at 4° C. The supernatant was carefully removed without disrupting the pellet. The pellet was resuspended in the desired volume of serum-free medium and sampled for particle count.

Example 4: CDC-EVs (10 KDa Method & 1000 KDa Method); MSC-EVs; Newt-EVs

A) 10 KDa & 1000 KDa

CDC-EV (10 KDa or 1000 KDa) drug substance is obtained after filtering CDC conditioned medium (CM) containing EVs through a 10 KDa or 1000 KDa pore size filter. The final product, composed of secreted EVs and concentrated CM, is formulated in PlasmaLyte A and stored frozen. The frozen final product is ready to use for direct subconjunctival injection or topical delivery after thawing.

Concentration: 2 mg/ml for the 10 KDa method; 0.5 mg/ml for the 1000 KDa method.

Particle concentration: $1.0 \times 10^{11}$ particles/ml for the 10 KDa method; $5.0 \times 10^{10}$ particles/ml for the 1000 KDa method.

B) MSC-EVs

Extracellular vesicles originating from human bone marrow mesenchymal stem cells (MSC-EVs) are obtained after filtering MSC CM containing EVs through a 10 KDa pore size filter following a similar process as for CDC-EV production. MSC-EVs are a non-cellular, filter sterilized product obtained from human MSCs cultured under defined, serum-free conditions. The final product, composed of secreted EVs and concentrated CM, is formulated in PlasmaLyte A and stored frozen. The frozen final product is "ready to use" for direct subconjunctival injection after thawing.

C Newt-EVs

Extracellular vesicles originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Example 5: Test and Control Articles

The test article is a non-cellular, filter sterilized product obtained from human CDCs cultured under defined, serum-free conditions, prepared as exemplified in Examples 1-3. The general characteristics of the test article are summarized in Table 2.

TABLE 2

| Characteristics | Description |
| --- | --- |
| Drug Substance | Extracellular vesicles in conditioned medium obtained from CDCs |
| Excipient | PlasmaLyte A solution (Baxter) |
| Pharmaceutical Form | Suspension for injection |
| Dosage/Strength | 0.4 ± 0.08 mg per 0.2 mL dose (10 kDa method) |
| Fill/Vial Size | 0.4 mL per 2 mL vial |
| Product Container | CellSeal ® closed-system vial with needleless luer fittings |
| Storage Conditions | Frozen at ≤−70° C. |

The control article is PlasmaLyte A, which is a sterile, non-pyrogenic crystalloid isotonic solution.

The test and control articles were thawed for dosing overnight or on the day of dosing, and kept on wet ice throughout the dosing procedures.

Example 6: Pre-Treatment Examinations

Prior to placement on study, each animal underwent an ophthalmic examination (slit-lamp biomicroscopy and indirect ophthalmoscopy). Ocular findings were scored according to a modified McDonald-Shadduck Scoring System (T. McDonald and J. A. Shadduck, "Eye irritation," in Advances in Modern Toxicology: Dermatoxicology, F. Marzulli and H. L. Maibach, Eds., pp. 579-582, Hemisphere Publishing Corporation, Washington, DC, USA, 1977), as summarized in Table 3. The acceptance criteria for placement on study were scores of "0" for all variables.

TABLE 3

| Examination | Definition | Scoring |
| --- | --- | --- |
| Conjunctival Discharge | Whitish gray precipitate from the eye | 0 = Normal; no discharge<br>1 = Discharge above normal and present on the inner portion of the eye but not on the lids or hairs of the eyelids<br>2 = Discharge is abundant, easily observed and has collected on the lids and hairs of the eyelids<br>3 = Discharge has been flowing over the eyelids so as to wet the hairs substantially on the skin around the eye. |
| Conjunctival Congestion | Enlarged blood vessels of the eye | 0 = Normal; may appear blanched to reddish pink without perilimbal injection (except at the 12:00 and 6:00 positions) with vessels of the palpebral and bulbar conjunctiva easily observed<br>1 = A flushed, reddish color predominantly confined to the palpebral conjunctiva with some perilimbal injection but primarily confined to the lower and upper parts of the eye from the 4:00 to 7:00 and 11:00 to 1:00 positions<br>2 = Bright red color of the palpebral conjunctiva with accompanying perilimbal injection covering at least 75% of the circumference of the perilimbal region<br>3 = Dark, beefy red color with congestion of both the bulbar and palpebral conjunctiva along with pronounced perilimbal injection and the presence of petechia on the conjunctiva; the petechia generally predominates along the nictitating membrane and upper palpebral conjunctiva |
| Conjunctival Swelling | Swelling of the conjunctiva | 0 = Normal or no swelling of the conjunctival tissue<br>1 = Swelling above normal without eversion of the eyelids (easily discerned by noting upper and lower eyelids are positioned as in the normal eye); swelling generally starts in the lower cul-de-sac near the inner canthus<br>2 = Swelling with misalignment of the normal approximation of the lower and upper eyelids; primarily confined to the upper eyelid so that in the initial stages, the misapproximation of the eyelids begins by partial eversion of the upper eyelid. In this stage the swelling is confined generally to the upper eyelid with some swelling in the lower cul-de-sac<br>3 = Swelling definite with partial eversion of the upper and lower eyelids essentially equivalent; this can be easily observed by looking at the animal head-on and noting the position of the eyelids; if the eye margins do not meet, eversion has occurred<br>4 = Eversion of the upper eyelid is pronounced with less pronounced eversion of the lower eyelid. It is difficult to retract the lids and observe the perilimbal region |
| Iris Involvement | Hyperemia of the blood vessels in the iris | 0 = Normal iris without any hyperemia of the blood vessels<br>1 = Minimal injection of the secondary vessels but not tertiary vessels; generally uniform but may be of greater intensity at the 12:00 to 1:00 or 6:00 position; if confined to this area, the tertiary vessels must be substantially hyperemic<br>2 = Minimal injection of tertiary vessels and minimal to moderate injection of the secondary vessels<br>3 = Moderate injection of the secondary and tertiary vessels with slight swelling of the iris stroma (the iris surface appears slightly rugose, usually most predominant near the 3:00 and 9:00 positions) |

TABLE 3-continued

| Examination | Definition | Scoring |
|---|---|---|
| | | 4 = Marked injection of the secondary and tertiary vessels with marked swelling of the iris stroma; the iris appears rugose; may be accompanied by hemorrhage (hyphema) in the anterior chamber |
| Cornea | Abnormalities in the cornea | 0 = Normal Cornea<br>1 = Some loss of transparency; only the epithelium and/or the anterior half of the stroma are involved; the underlying structures are clearly visible although some cloudiness may be readily apparent<br>2 = Involvement of the entire thickness of the stroma; with diffuse illumination, the underlying structures are just barely visible (can still observe flare, iris, pupil response, and lens)<br>3 = Involvement of the entire thickness of the stroma; with diffuse illumination, the underlying structures cannot be seen |
| Surface Area of Cornea Involvement | Cloudiness in the stromal region | 0 = Normal<br>1 = 1-25% area of stromal cloudiness<br>2 = 26-50% area of stromal cloudiness<br>3 = 51-75% area of stromal cloudiness<br>4 = 76%-100% area of stromal cloudiness |
| Pannus | Vascularization of the cornea | 0 = No pannus (vascularization of the cornea)<br>1 = Vascularization present but vessels have not invaded the entire cornea circumference<br>2 = Vessels have invaded 2 mm or more around entire corneal surface |
| Pupillary Response | Blockage or a sluggish response in the pupillary region | 0 = Normal pupil response<br>1 = Sluggish or incomplete pupil response<br>2 = No pupil response<br>3 = No pupil response due to pharmacological blockage |
| Aqueous Flare | Breakdown of the blood-aqueous barrier | 0 = None<br>1 = 1+<br>2 = 2+<br>3 = 3+<br>4 = 4+ (fibrin) |
| Cellular Flare | Cellular observation in the anterior chamber | 0 = None<br>1 = 1+<br>2 = 2+<br>3 = 3+<br>4 = 4+ |
| Lens | Cataracts in the lens | 0 = Lens clear<br>1 = Anterior (cortical/capsular)<br>2 = Nuclear<br>3 = Posterior (cortical/optical)<br>4 = Equatorial |
| Vitreous | Observe the vitreous for any abnormalities. | 0 = Clear vitreous<br>1 = Few scattered opacities, fundus unimpaired<br>2 = Moderate scattered opacities, fundus details somewhat obscured<br>3 = Many opacities, marked blurring of fundus details<br>4 = Dense opacities, no fundus view |
| Vitreal Hemorrhage | Hemorrhage in the vitreous | 0 = None<br>1 = 1-25%<br>2 = 26-50%<br>3 = 51-75%<br>4 = 76-100% |
| Retinal Detachment | Clouding of the interior of the eye, which is normally filled with vitreous fluid, due to bleeding from small retinal blood vessels during a retinal detachment | 0 = None<br>1 = Rhegmatogenous (retinal detachment occurs when subretinal fluid accumulates in the potential space between the neurosensory retina and the underlying retinal pigment epithelium)<br>2 = Exudative (occurs due to inflammation, injury, or vascular abnormalities that results in fluid accumulating underneath the retina without the presence of a hole, tear, or break)<br>3 = Tractional (occurs when fibrous or fibrovascular tissue, caused by an injury, inflammation, or neovascularization that pulls the sensory retina from the retinal pigment epithelium) |
| Retinal Hemorrhage | Abnormal bleeding of the blood vessels in the retina | 0 = None<br>1 = 1-25%<br>2 = 26-50%<br>3 = 51-75%<br>4 = 76-100% |

TABLE 3-continued

| Examination | Definition | Scoring |
|---|---|---|
| Choroidal/Retinal Inflammation | Inflammation of the retina and/or choroid | 0 = None<br>1 = Mild<br>2 = Moderate<br>3 = Severe |

Example 7: Corneal Alkali Burn Animal Model and Study Design

Eighteen (18) male Sprague Dawley rats, weighing approximately 200 grams at study start, were obtained from Charles River Laboratories.

The animals were housed individual cages and within the same room Primary enclosures were as specified in the USDA Animal Welfare Act (Section 9, Parts 1, 2 and 3, of the Code of Federal Regulations) and as described in the Guide for Care and Use of Laboratory Animals (ILAR publication, 2011, National Academy Press). No other species was housed in the same room The room was well ventilated (greater than 10 air changes per hour) with at least 60% fresh air. A 12-hour light/12-hour dark photoperiod was maintained, except when the room was illuminated during the dark cycle to accommodate necessary study procedures. The animals had ad libitum access to species specific chow. No contaminants were known to be present in the diet at levels that would interfere with the results of the study. Municipal tap water was available ad libitum to each animal. No contaminants were known to be present in the water at levels that would interfere with the results of the study. The animals were acclimated to their designated housing for at least three days prior to the first day of dosing.

The animals were anesthetized with an intramuscular or subcutaneous injection of ketamine hydrochloride (up to approximately 80 mg/kg) and xylazine (up to approximately 12 mg/kg) prior to the creation of corneal alkali burns. Isoflurane may be used as an alternative. One to two drops of topical proparacaine hydrochloride anesthetic (0.5%) were applied to the animal's eye prior to the procedure. Additional topical ocular anesthesia dosing was utilized during the procedure as needed. During recovery from anesthesia, the animals were monitored until sternal recumbancy was achieved.

After the animals were anesthetized, corneal alkali burns were created on Day O in the right eye (OD) of each rat with sodium hydroxide (NaOH). A round filter paper (~2-3.5 mm in diameter) soaked with IN NaOH was placed on the center of the corneal surface for ~30 seconds to induce the corneal burn. Then the ocular surface was rinsed with ~60 mL of normal saline. Buprenorphine (0.5 to 1.0 mg/kg) was given for postoperative analgesia.

After alkali burn creation and prior to dosing, wound severity was evaluated in all animals, and the animals were assigned to one of 3 experimental groups (see below in Table 2) based on wound severity. The animals were assigned a numeric rank from 1 to 18 according to wound severity in a decreasing order (e.g., the animal with the highest wound severity was assigned rank of 1), and were assigned to the experimental groups according to the scheme as shown in Table 4.

TABLE 4

| Group 1 | Group 2 | Group 3 |
|---|---|---|
| 1 | 2 | 3 |
| 6 | 5 | 4 |
| 7 | 8 | 9 |
| 12 | 11 | 10 |
| 13 | 14 | 15 |
| 18 | 17 | 16 |

The test and control articles were administered according to the study design as shown in Table 5.

TABLE 5

| Group | Treatment OD | Treatment OS | Dose route (OD) | Dose (µg/eye) | Dose Volume (µL) | Concentration (mg/mL) | Examination Schedule* | Sacrifice Time Points | Tissues Collected |
|---|---|---|---|---|---|---|---|---|---|
| 1 | Control article | Untreated | Topical (TID starting Day 1) | NA | 10 | NA | Day 0 (immediately after wound creation), Days 4, 7, 14, 21 (immediately prior to euthanasia) on treated eyes only (OD) | Day 21 | Eyes (entire globe) OU |
| 2 | Test article | | Topical (TID starting Day 1) | 60 (3 × 20 µg) | 10 | 2 | | | |
| 3 | Test article | | Single Subconjunctival Injection on Day 1 | 20 | 10 | 2 | | | |

OD: right eye;
OS: left eye;
TID: 3 times daily;
NA: not applicable
*Examinations include slit lamp biomicroscopy, fluorescein staining, and digital photographs For Groups 1 and 2, the test or control articles were administered to the right eye (OD) via 3 times daily (TID) topical administration at a volume of 10 μL per eye starting on Day 1 and continuing until the end of the study. For Group 3, the test article was administered OD as a single subconjunctival injection on Day 1. The animals were anesthetized as described above. Using forceps, the conjunctiva was grabbed and gently pulled up until the junction between the conjunctiva and sclera was exposed. A small gauge needle (30G, 31G, or 32G) was inserted laterally into the eye at the junction. 10 μL of the test article was administered and the needle was removed. After application of the test article, the eye was examined via slit-lamp examination to ensure that minimal compound has left the eye.

All surviving animals in all groups were sacrificed on Day 21 and subjected to necropsy. Unscheduled deaths were also subjected to necropsy. At scheduled sacrifice, the following organs (when present) were weighed before fixation: brain, cervical lymph nodes (submandibular), heart, kidneys, liver, lung, and testes. The following tissues from all scheduled sacrifice animals were collected and preserved in 10% neutral buffered formalin (except for the eyes which were preserved in Davidson's fixative buffer and the testes that were preserved in Bouin's solution): brain, cervical lymph nodes (submandibular), eyes, heart, kidneys, liver, lung, and testes. The eyes were collected for all animals including unscheduled deaths.

Alternatively, New Zealand White rabbits (*Oryctolagus cuniculus*; single sex) may be used to evaluate the efficacy of CDC-EVs (10 KDa or or 1000 KDa), MSC-EVs, or Newt-Evs, following a similar protocol as for Sprague Dawley rats. For instance, the test and control articles may administered according to the study design as shown in Table 6, wherein each group includes 6 rabbits assigned in a similar manner as described in Example 7.

TABLE 6

| Group | Treatment OD | OS | Dose route (OD) | Dose (μg/eye) | Dose Volume (μL) | Concentration (mg/mL) | Examination Schedule* | Sacrifice Time Points |
|---|---|---|---|---|---|---|---|---|
| 1 | Control article | Untreated | Single Subconjunctival Injection on Day 1 | NA | 100 (2 × 50) | NA | Day 0 (immediately after wound creation), Day 2 (~24 hrs after first dose), Days 4, 7, 14 (±1), 21 (±1), and optionally 28 (±2) (immediately prior to euthanasia) on treated eyes only (OD) | Day 22 (±1), or Day 28 (±2) |
| 2 | CDC-EVs (10 kD Method) | | | 200 (2 × 100) | 100 (2 × 50) | 2 | | |
| 3 | CDC-EVs (1000 kD Method) | | | 50 (2 × 25) | 100 (2 × 50) | 0.5 | | |

Further alternatively, Table 7 shows another variation of the study design to evaluate the efficacy of CDC-EVs, MSC-EVs, or newt-Evs, using the corneal alkali burn rat model, wherein each group includes 6 rats assigned in a similar manner as described in Example 7.

TABLE 7

| Group | Treatment OD | OS | Dose route (OD) | Dose (μg/eye) | Dose Volume (μL) | Concentration (mg/mL) | Examination Schedule* | Sacrifice Time Points |
|---|---|---|---|---|---|---|---|---|
| 1 | Control article | Untreated | Topical (TID starting Day 1) | NA | 10 | NA | Day 0 (immediately after wound creation), Day 2 (~24 hrs after first dose), Days 4, 7, 14 (±1), 21 (±1), and optionally 28 (±2) (immediately prior to euthanasia) on treated eyes only (OD) | Day 22 (±1), or Day 28 (±2) |
| 2 | Prednisolone acetate (Positive Control) | | | ~30 (1 drop) | 10 | 10 (1%) | | |
| 3 | CDC-EVs | | Topical (QD starting Day 1) | TBD | 10 | TBD | | |
| 4 | CDC-EVs | | Topical (Q3 D starting Day 1) | TBD | 10 | TBD | | |
| 5 | CDC-EVs | | Topical (QWK starting Day 1) | TBD | 10 | TBD | | |

TABLE 7-continued

| Group | Treatment OD | OS | Dose route (OD) | Dose (µg/eye) | Dose Volume (µL) | Concentration (mg/mL) | Examination Schedule* | Sacrifice Time Points |
|---|---|---|---|---|---|---|---|---|
| 6 | Control article | | Subconjunctival Injection on Day 1 & Day 14 | NA | 10 | NA | | |
| 7 | CDC-EVs | | | TBD | 10 | TBD | | |
| 8 | MSC-EVs | | | TBD | 10 | TBD | | |
| 9 | Newt-EVs | | | TBD | 10 | TBD | | |

QD: 1 time daily;
Q3 d: every 3 days;
QWK: every week

Further alternatively, Table 8 shows another variation of the study design to evaluate the efficacy of CDC-EVs (10 KDa or 1000 KDa) with the corneal alkali burn rat model, wherein each group includes 6 rats assigned in a similar manner as described in Example 7.

TABLE 8

| Group | Treatment OD | OS | Dose route (OD) | Dose (µg/eye) | Dose Volume (µL) | Concentration (mg/mL) | Examination Schedule* | Sacrifice Time Points |
|---|---|---|---|---|---|---|---|---|
| 1 | Control article | Untreated | Single Subconjunctival Injection on Day 1 | NA | 10 | NA | Day 0 (immediately after wound creation), Day 2 (~24 hrs after first dose), Days 4, 7, 14 (±1), 21 (±1), and optionally 28 (±2) (immediately prior to euthanasia) on treated eyes only (OD) | Day 22 (±1), or Day 28 (±2) |
| 2 | CDC-EVs (10 kD Method) | | | 20 | 10 | 2 | | |
| 3 | CDC-EVs (1000 kD Method) | | | 5 | 10 | 0.5 | | |

Further alternatively, Table 9 shows another variation of the study design to evaluate the efficacy of EVs with the corneal alkali burn rat model, wherein each group includes 6 rats assigned in a similar manner as described in Example 7.

TABLE 9

| Group | Treatment OD | OS | Dose route (OD) | Dose (µg/eye) | Dose Volume (µL) | Concentration (mg/mL) | Examination Schedule* | Sacrifice Time Points |
|---|---|---|---|---|---|---|---|---|
| 1 | Control article | Untreated | Subconjunctival Injection on Day 1 & Day 14 | NA | 20 µL (10 µL on Day 1 + 10 µL on Day 14) | TBD | Day 0 (immediately after wound creation), Day 2 (~24 hrs after first dose), Days 4, 7, 14 (±1), 21 (±1), and optionally 28 (±2) (immediately prior to euthanasia) on treated eyes only (OD) | Day 22 (±1), or Day 28 (±2) |
| 2 | TBD | | | TBD | | TBD | | |
| 3 | TBD | | | TBD | | TBD | | |

Further alternatively, Table 10 shows another variation of the study design to evaluate the efficacy of CDC-EVs with the corneal alkali burn rat model, wherein each group includes 6 rats assigned in a similar manner as described in Example 7.

TABLE 10

| Group | Treatment OD | OS | Dose route (OD) | Dose (μg/eye) | Dose Volume (μL) | Concentration (mg/mL) | Examination Schedule* | Sacrifice Time Points |
|---|---|---|---|---|---|---|---|---|
| 1 | Control article | Untreated | Subconjunctival Injection on Day 1 & Day 14 | NA | 20 μL (10 μL on Day 1 + 10 μL on Day 14) | NA | Day 0 (immediately after wound creation), Day 2 (~24 hrs after first dose), Days 4, 7, 14 (±1), 21 (±1), and optionally 28 (±2) (immediately prior to euthanasia) on treated eyes only (OD) | Day 22 (±1), or Day 28 (±2) |
| 2 | CDC-EVs (UC isolated) | | | TBD | | TBD | | |
| 3 | CDC-EVs (UFC isolated; 10 KDa) | | | TBD | | TBD | | |
| 4 | CDC-EVs (UFC isolated; 1000 KDa) | | | TBD | | TBD | | |

Example 8: Histopathologic Examination

The treated eyes from all animals, including unscheduled deaths, were processed, embedded in paraffin, sectioned and stained with hematoxylin and eosin (H&E). Animal information was entered into Pristima®. All microscopic slides were evaluated directly into Pristima®. In Pristima®, scoring criteria is as follows: 1=minimal; 2=mild; 3=moderate; 4=marked; 5=severe. Microscopic findings are presented in the Histopathology Incidence Table 11.

TABLE 11

| Eye, right | Dosage Group: | Group 1 | Group 2 | Group 3 |
|---|---|---|---|---|
| | Number of animals: | 6 | 4 | 6 |
| | Number examined: | 6 | 4 | 6 |
| | Number unremarkable: | 1 | 1 | 1 |
| Erosion, corneal epithelium | 3> | 1 | 0 | 0 |
| | Total finding incidence: | 1 | 0 | 0 |
| Fibrosis | 1> | 0 | 0 | 1 |
| | 2> | 2 | 1 | 2 |
| | 4> | 1 | 0 | 0 |
| | Total finding incidence: | 3 | 1 | 3 |
| Hemorrhage | 1> | 0 | 1 | 0 |
| | 2> | 1 | 0 | 0 |
| | 3> | 1 | 0 | 0 |
| | Total finding incidence: | 2 | 1 | 0 |
| Hyperplasia, corneal epithelium | 1> | 0 | 0 | 2 |
| | 3> | 1 | 0 | 0 |
| | Total finding incidence: | 1 | 0 | 2 |
| Mixed infiltration, cornea | 1> | 1 | 0 | 0 |
| | 2> | 1 | 1 | 1 |
| | 3> | 1 | 0 | 0 |
| | Total finding incidence: | 3 | 1 | 1 |
| Mononuclear infiltration, cornea | 1> | 1 | 0 | 0 |
| | Total finding incidence: | 1 | 0 | 0 |
| Mononuclear infiltration, iris | 1> | 4 | 2 | 5 |
| | Total finding incidence: | 4 | 2 | 5 |

TABLE 11-continued

| Eye, right | Dosage Group: | Group 1 | Group 2 | Group 3 |
|---|---|---|---|---|
| Neovascularization | 1> | 2 | 0 | 3 |
| | 2> | 0 | 1 | 0 |
| | Total finding incidence: | 2 | 1 | 3 |
| Synechiae | 1> | 1 | 2 | 3 |
| | 2> | 2 | 0 | 0 |
| | Total finding incidence: | 3 | 2 | 3 |
| Vacuolar degeneration, corneal epithelium | 2> | 0 | 0 | 1 |
| | 3> | 0 | 0 | 1 |
| | Total finding incidence: | 0 | 0 | 2 |
| Vesicles, corneal epithelium | 2> | 1 | 2 | 0 |
| | Total finding incidence: | 1 | 2 | 0 |

There were two unscheduled deaths on Day 14 in Group 2 that occurred under anesthesia. These deaths were not considered treatment related.

At study Day 21, lesions were found in all test groups in the cornea and iris. Lesions were found in the anterior and posterior aqueous and vitreal chambers in two Group 1 animals and one Group 2 animal. The presence and severity of lesions within treatment groups suggests significant variability in model induction.

Cornea

There was epithelial degeneration characterized by mild to moderate epithelial vacuolar degeneration present in 2 of 6 Group 3 animals and mild focal sub-basilar epithelial vesicle formation in 1 of 6 Group 1 and 2 of 4 Group 2 animals.

Stroma

There was fibrosis of the stroma as well as formation of subcorneal fibrotic membrane in all groups. Stromal fibrosis occurred in 2 of 6 animals in Group 1; 1 of 4 animals in Groups 2; and 3 of 6 animals in Group 3, and consisted of focal, centrally located, subepithelial fibrosis and frequently occurred along with neovascularization. Neovascularization occurred at comparable incidence and severity in all groups. Subcorneal fibrotic membranes occurred in 3 of 6 Group 1 animals and 1 animal from each Group 2 and Group 3, and were characterized by loose fibrotic tissue, frequently admixed with inflammatory cells, and adhered to the posterior aspect of the cornea.

There was occasional infiltration within the corneal stroma that was minimal to moderate and was composed of either mononuclear or mixed inflammatory cells. The incidence and severity of infiltration was lower in Group 3 compared to controls with only one animal of 6 with mild infiltration compared to minimal to moderate infiltration occurring in 4 of 6 control animals. Group 2 also had a reduced incidence and severity of infiltration relative to controls with an incidence of one animal of 4 with minimal infiltration.

Iris, Lens, and Chambers of the Eye

Minimal to mild mononuclear infiltration occurred in all treatment groups. In addition, minimal to mild anterior and/or posterior synechiae occurred in 3 of 6 animals from each Group 1 and Group 3, and 2 of 4 animals in Group 2. This was likely a sequela of the inflammatory response to wound induction.

There was minimal to moderate hemorrhage in two Group 1 animals (mild or moderate) and one Group 2 animal (minimal). This was likely secondary to the trauma of wound formation.

In summary, there was decreased incidence and severity of corneal inflammation with both a single subconjunctival injection of the test article at a dose of 20 µg/eye and daily topical administration of the test article at a dose of 20 µg/eye three times per day compared to control treated animals. There was also a slight decrease in the severity in the type of corneal lesion present (epithelial vacuolar degeneration versus erosion and vesicle formation) in animals treated with the subconjunctival test article at 20 µg/eye compared to both control treated animals and animals treated with the topical test article at 20 µg/eye three times per day.

Conclusion

Under the conditions of this study, a single subconjunctival injection of the test article at a dose of 20 µg/eye and daily topical administration of the test article at 20 µg/eye three times daily for 21 days slightly decreased the incidence and severity of corneal inflammation compared to controls, and a single subconjunctival injection of the test article at a dose of 20 µg/eye slightly decreased the severity of corneal epithelial lesions compared to both control treated eyes and eyes treated with the topical test article at 20 µg/eye three times daily in a corneal alkali burn model in rats.

Example 9: In-Life Observations and Measurements

Key study parameters and schedule are summarized in Table 12.

TABLE 12

| Group # | # of Animals | # of Eyes | Treatment OD | OS |
|---|---|---|---|---|
| 1 | 6 | 12 | Control article topical delivery | Untreated |
| 2 | 6 | 12 | Test article topical delivery | Untreated |
| 3 | 6 | 12 | Test article subconjunctival delivery | Untreated |

| | |
|---|---|
| Study Duration | 22 days |
| General Health Observations | Daily |
| Body Weights | Prior to wounding procedure, weekly, and prior to termination |

TABLE 12-continued

| | |
|---|---|
| Clinical Ophthalmic Exams (with Fluorescein Staining and Slit-lamp Photography) | Baseline, Day 0 immediately after wound creation, Days 4, 7, and 14, and Day 21 immediately prior to euthanasia |
| Tissue Collection | Day 21: Both eyes (entire globes) Collected into Davidson fixation buffer Samples were stored refrigerated at 2-8° C. Total samples: 36 eyes |

The animals were observed within their cages once daily throughout the study period. Each animal was observed for changes in general appearance and behavior. General health observations were recorded daily beginning on Day 0. The animals were weighed prior to the wounding procedure, weekly, and prior to termination. Clinical ophthalmic examinations (including slit-lamp biomicroscopy and fluorescein staining) were performed at baseline, on Day O immediately after the wounding procedure, on Days 4, 7, and 14, and on Day 21 immediately prior to euthanasia. Examinations were performed by utilizing the modified McDonald-Shadduck scoring system, as summarized above in Table 3.

Figure 3:
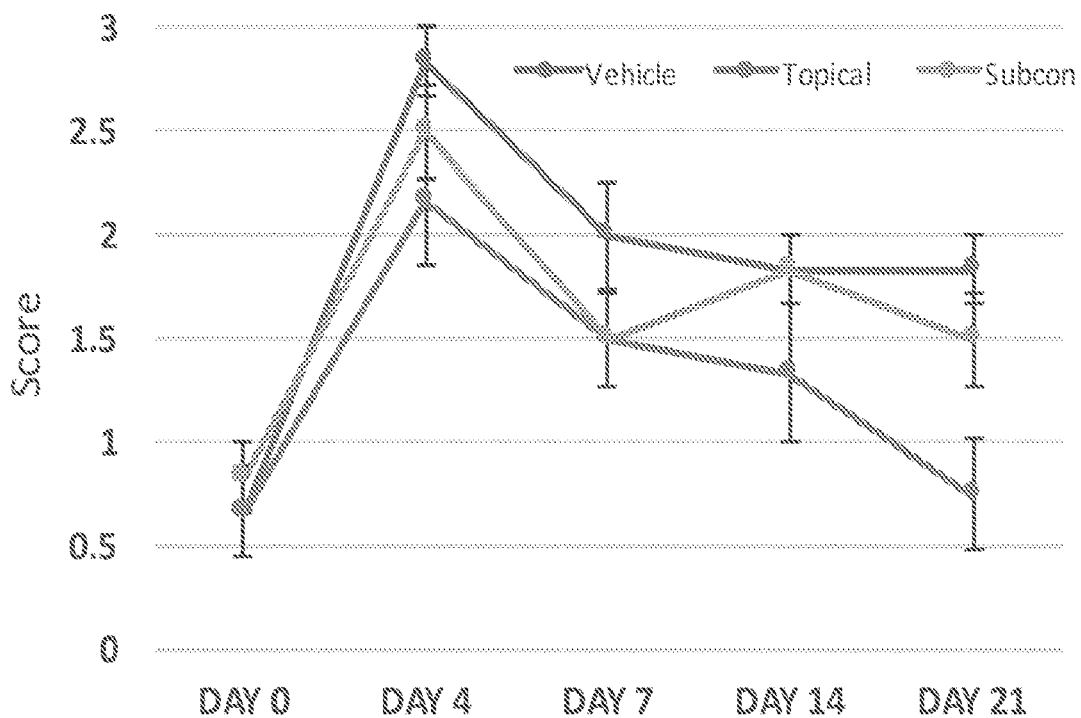
FIG. 3 graphically shows the effects of topical and subconjunctival administration of exosomes relative to the control group over 21 days, on the parameter of conjunctival congestion.
Figure 4:
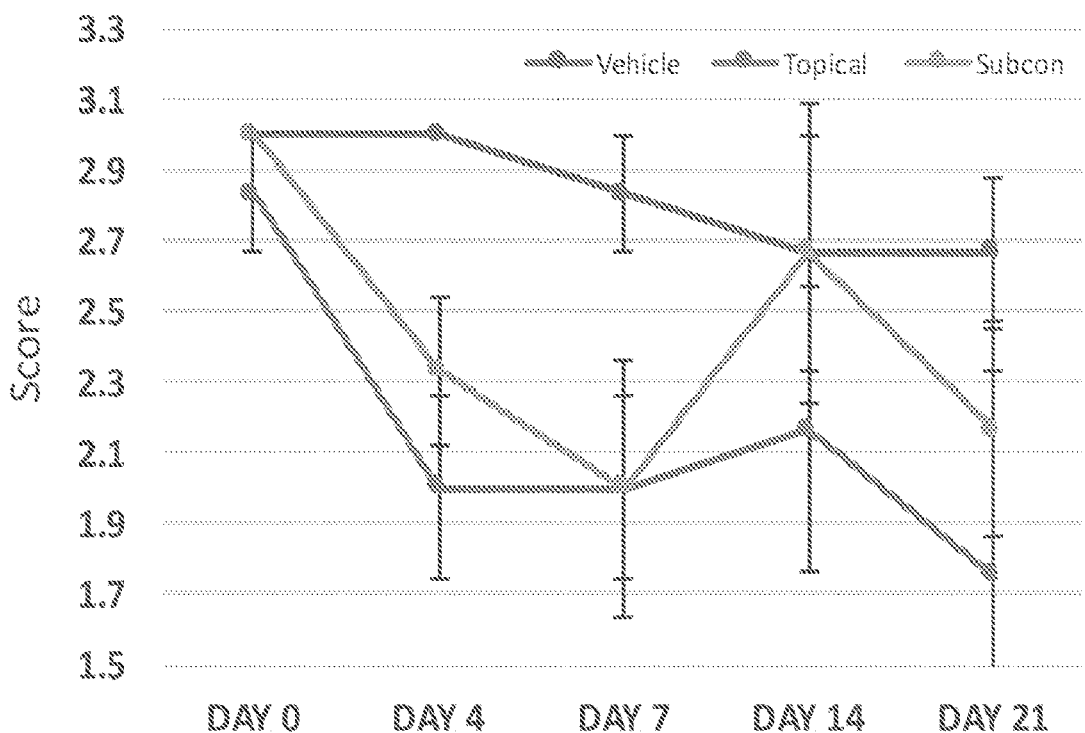
FIG. 4 graphically shows the effects of topical and subconjunctival administration of exosomes relative to the control group over 21 days, on the parameter of corneal opacification.
Figure 5:
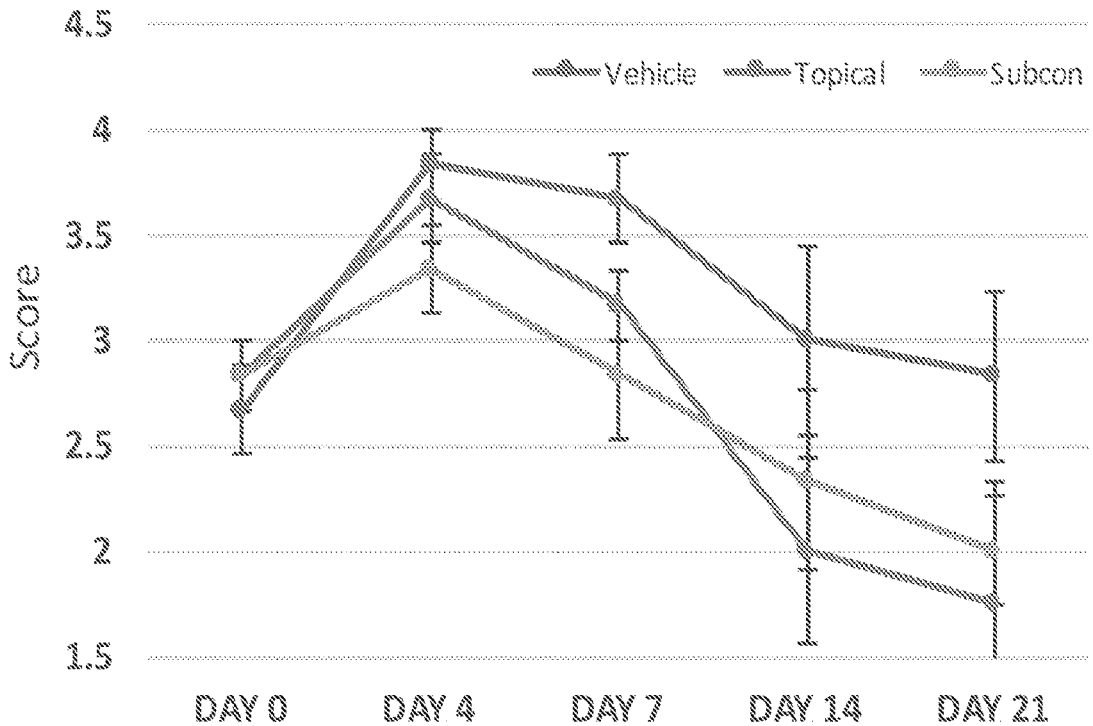
FIG. 5 graphically shows the effects of topical and subconjunctival administration of exosomes relative to the control group over 21 days, on the parameter of corneal surface area affected.
Figure 6:
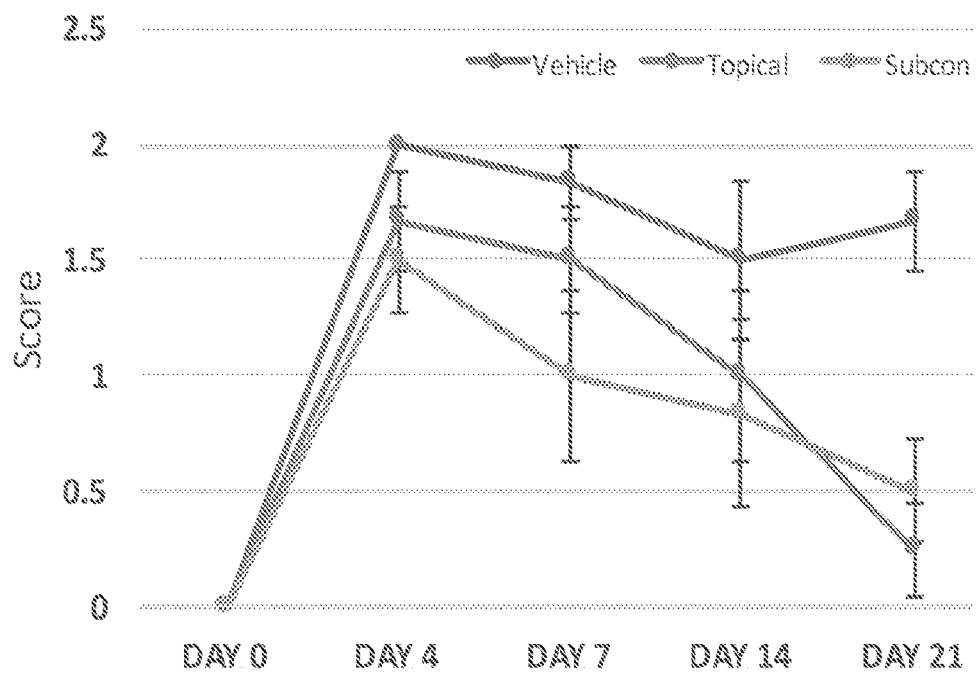
FIG. 6 graphically shows the effects of topical and subconjunctival administration of exosomes relative to the control group over 21 days, on the parameter of corneal vascular pannus.
Figure 7:
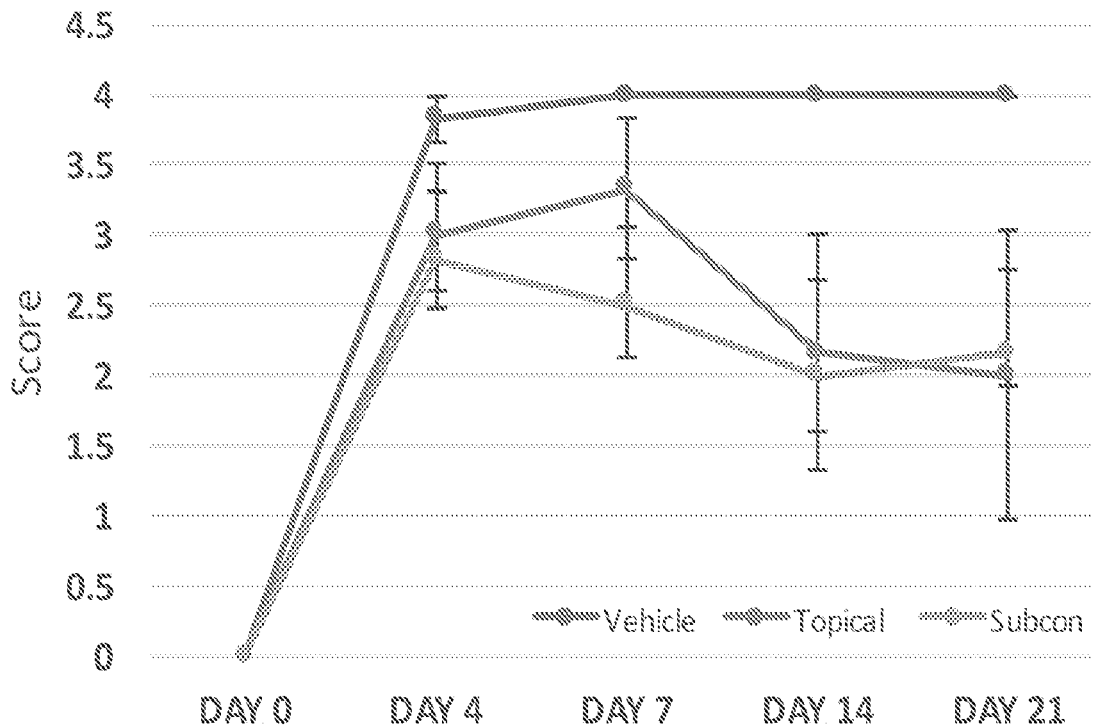
FIG. 7 graphically shows the effects of topical and subconjunctival administration of exosomes relative to the control group over 21 days, on the parameter of aqueous flare as a measure of inflammation.
Figure 8:
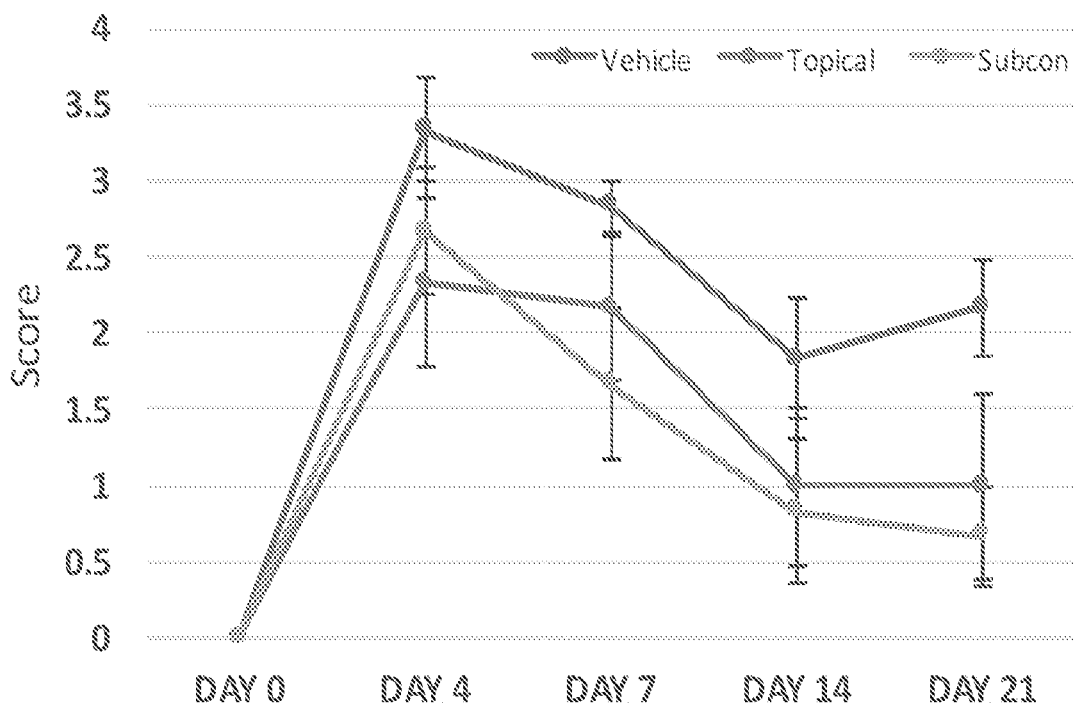
FIG. 8 graphically shows the effects of topical and subconjunctival administration of exosomes relative to the control group over 21 days, on the parameter of aqueous cell as a measure of inflammation.
Figure 9:
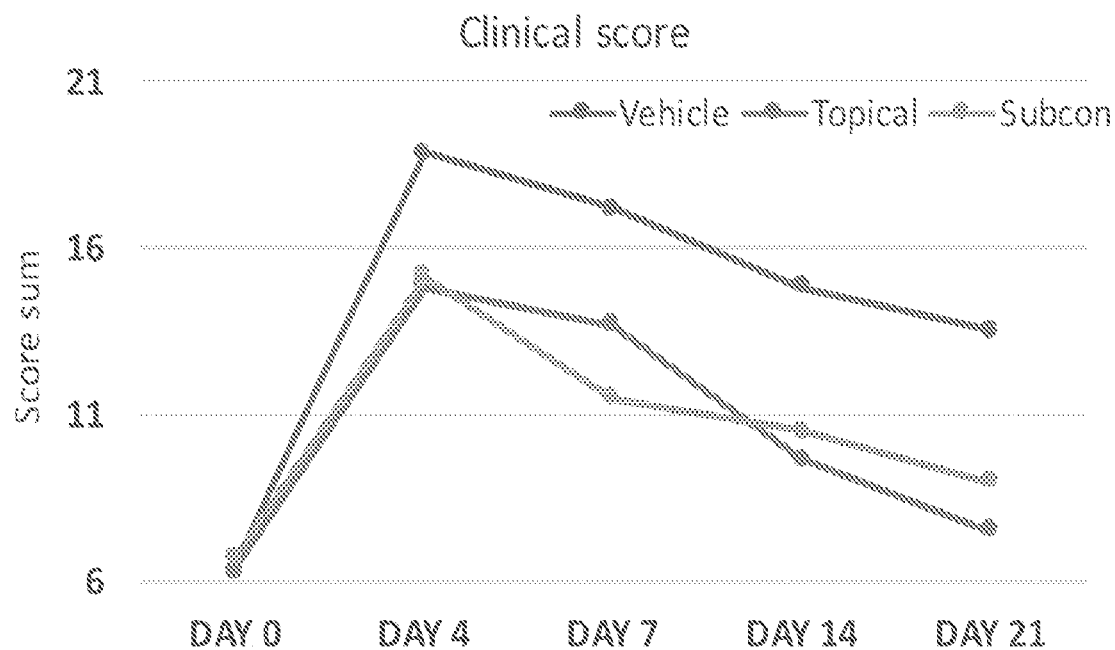
FIG. 9 graphically shows the effects of topical and subconjunctival administration of exosomes relative to the control group over 21 days, on the overall clinical score which is a sum of the score average of the parameters of conjunctival congestion as shown in FIG. 3, corneal opacification as shown in FIG. 4, corneal surface area affected as shown in FIG. 5, corneal vascular pannus as shown in FIG. 6, aqueous flare as shown in FIG. 7, and aqueous cell as shown in FIG. 8.

FIG. 9 graphically shows the effects of topical and subconjunctival administration of the test article relative to the control article over 21 days, on the overall clinical score which is a sum of the score average of the parameters of conjunctival congestion as shown in FIG. 3, corneal opacification as shown in FIG. 4, corneal surface area affected as shown in FIG. 5, corneal vascular pannus as shown in FIG. 6, aqueous flare as shown in FIG. 7, and aqueous cell as shown in FIG. 8 (maximum score 20 points).

As shown in FIG. 6, both topical and subconjunctival administration of the test article dramatically reduced the degree of neovascularization of the cornea which is an inevitable, worsening, typically irreversible, and devastating consequence of limbal stem cell and corneal epithelial deficiency. Without an intact epithelium, conjunctival epithelium (which is opaque and highly vascularized) and new blood vessels in the deeper layers of the cornea, migrate from the periphery (limbus) in toward the center of the cornea. When this happens, visual acuity is significantly reduced and the patient ceases to be a cornea transplant candidate, due to the presence of new blood vessels that would stimulate graft rejection. This is not a parameter that heals on its own; in fact, over, time, it will worsen without treatment, and there is a point of no return. The fact that these data show such significant reduction in vascular pannus in the test article-treated groups also supports that exosomes enhance recovery of the corneal epithelium, which is critical for effectively treating chemical injuries of the eye.

Figure 10:
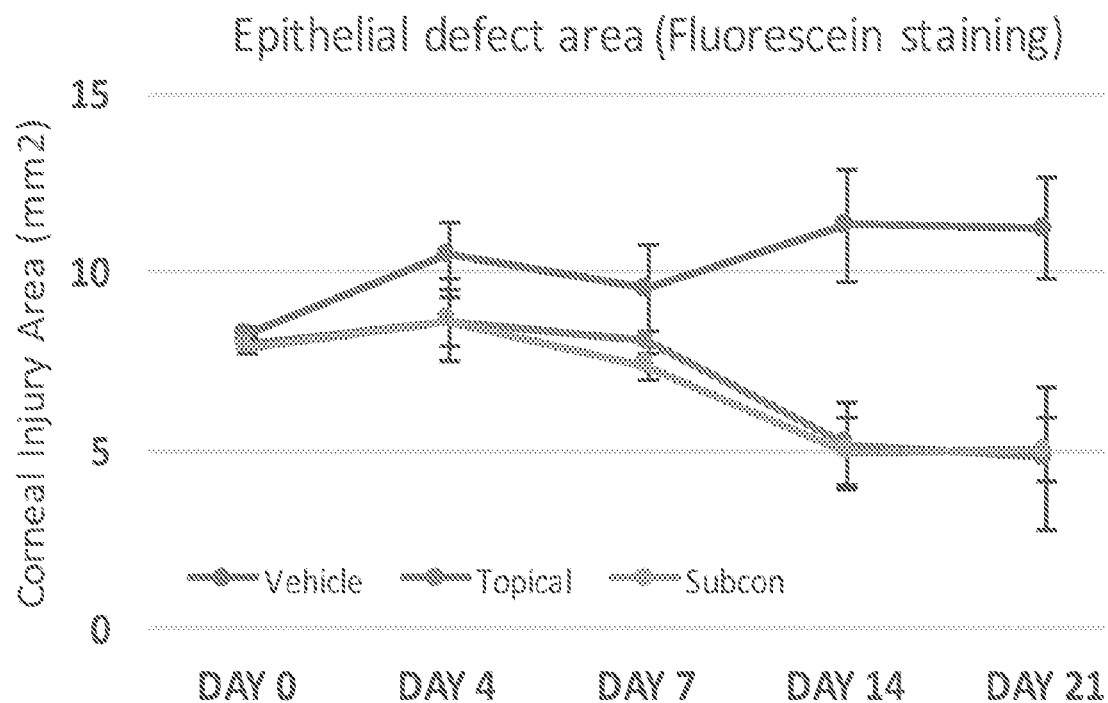
FIG. 10 graphically shows the effects of topical and subconjunctival administration of exosomes relative to the control group over 21 days, on the parameter of epithelial defect area evaluated using fluorescein staining.

As shown in FIG. 10, both topical and subconjunctival administration of the test article dramatically reduced the size of corneal epithelial defect, whereas the control article-treated eyes actually worsened over time (consistent with natural history of untreated burns). These data reflect a real clinical effect. Reduction in epithelial defect area evaluated using fluorescein staining is the most clinically significant endpoint because, without it, corneal infections, melting and permanent opacification of the corneal stroma, and permanent corneal neovascularization (conjunctivalization) would occur. Since fluorescein does not get cleared from the cornea immediately after being applied, it essentially "paints" de-epithelialized tissues, permitting it to glow. The corneal epithelial regrowth depends on the limbal epithelial stem cells, which reside at the junction between the clear cornea and the white/opaque conjunctiva/sclera. The limbal stem cells are very sensitive to chemical injury and die in the presence of chemical insult and/or severe inflammation. The only parameter that impacts epithelial defect size is absence or presence of healthy epithelium, and the fact that these data show recovery of the corneal epithelium suggests that the test article possesses biologic activity in supporting the limbal epithelial stem cells, which is critical for effectively treating severe ocular surface injuries.

FIG. 6 and FIG. 10 together demonstrate that the test article, when administered as indicated, is efficacious in enhancing recovery of the corneal epithelium.

As shown in FIG. 4, topical administration of the test article appears effective in reducing the density of the corneal opacification after chemical injury. Corneal opacification was scored throughout the entire cornea. When the blue light is not shining on the eye, it is not easy to make out the epithelial defect area. Generally, the worse the epithelial defect, the denser and broader the corneal opacification (especially on a long-term basis, well outside the 21 day window). Early closure of the epithelial defect is critical for reduction in long-term scarring/opacification of the underlying corneal stroma. These data suggest that collagen synthesis is promoted and/or collagen breakdown is inhibited by the test article. This finding has significant clinical implications in view of the fact that corneal opacification is caused by disruption (via melting or cross-linking) of the collagen fibers via direct chemical insult and/or immune-mediated effects such as release of matrix metalloproteinases. When corneal stromal keratocytes are injured, they fail to synthesize and lay down new collagen fibers.

As shown in FIG. 5, topical and subconjunctival administration of the test article equally reduced the affected surface area of corneal opacification in this model, suggesting that collagen synthesis is promoted and/or collagen breakdown is inhibited by the test article. This finding has significant clinical implications in view of the fact that the impact of corneal opacification is proportional to both its density (reduction in transparency) and surface area.

FIG. 4 and FIG. 5 together demonstrate that the test article, when administered as indicated, is efficacious in augmenting collagen synthesis while minimizing collagen breakdown and sterile ulceration.

As shown in FIG. 7, both topical and subconjunctival administration of the test article significantly reduced aqueous flare, which is an important measure of intraocular inflammation, whereas the test article-treated eyes remained at a score of 4/4 across every measured time point. This is extremely significant clinically for two reasons. First, intraocular inflammation in the setting of chemical burns is largely responsible for permanent damage to critical internal structures of the eye, including the drainage channels (trabecular meshwork—leading to elevated intraocular pressure and glaucoma), retina, and optic nerve. There has been great interest recently in controlling intraocular inflammation in chemical burn patients with biologics such as anti-TNF drugs. Second, the only currently available therapy for intraocular and ocular surface inflammation in the setting of chemical burns is topical steroid eye drops. However, the use of such drops is limited to 10-14 days of continuous use due to the likelihood of causing a paradoxical "corneal melt" which, as its name suggests, causes the collagen fibers in the corneal stroma to break down and perforate the cornea. As such, there is a major unmet need for a safe, steroid-sparing anti-inflammatory agent with strong effect on both ocular surface and intraocular inflammation, which can be used far beyond the 10-14 day limit for steroids. Therefore, even if exosomes exhibit similar reduction in inflammation as steroids do, the likelihood that exosome treatment could safely be used far beyond the safety window for steroids shows it would fulfill a significant unmet need in the presently claimed indications of chemical injuries of the eye.

As shown in FIG. 8, both topical and subconjunctival administration of the test article significantly reduced cellular flare (i.e., aqueous cell), which is an important measure of intraocular inflammation, whereas the test article-treated eyes leveled out at a moderate level of inflammation. Aqueous cell refers to the actual presence (visible clinically with the slit lamp biomicroscope) of inflammatory cells floating in the anterior chamber of the eye, between the posterior surface of the eye and the anterior surface of the iris.

FIG. 7 and FIG. 8 together demonstrate that the test article, when administered as indicated, is efficacious in controlling inflammation of the eye, which is a critical component of efficacious treatment of chemical burns of the ocular surface according to the methods of the present invention.

Example 10: Efficacy of CDC-EVs in Rabbit Acute LPS Keratitis Model

The experimental study was divided in two phases:

Phase I: creation of ocular inflammation model (abrasion+ lipopolysaccharides (LPS) from *Serratia marcescens*). The acute keratitis was produced adapting the protocol described by Schultz et al., Exp Eye Res. 1997 January; 64(1):3-9.

Phase II: subconjunctival injection of extracellular vesicles. Follow-up and data collection. After euthanasia, eyes and parotid lymph nodes were harvested and submitted for histological evaluation.

A total of 18 female New Zealand rabbits (3-4 kg) were used for evaluation. Buprenorphine (0.02 mg/kg/12 h, IM) was administered to all animals for three days after the corneal epithelial abrasion. Animals were housed in individual cages with free access to food and water.

Phase I (Days 0, 1 and 2)

Pre-procedure pachymetry and slit lamp evaluations were performed to ensure animals had normal anatomy and corneal thickness.

Animals were pre-medicated by IM administration of atropine sulfate (0.05 mg/kg) and midazolam (0.5 mg/kg). Anesthetic induction was performed with propofol (4 mg/kg). After endotracheal intubation, animals were connected to a mechanical ventilation system and a sevoflurane vaporizer, setting the anesthetic agent flow to 3.5% sevoflurane. Analgesia was ensured by administering 1 mg/kg of ketorolac and 2 mg/kg of tramadol. Animals were 25 then placed in the left lateral decubitus keeping the right eye (RE) open with an eye speculum.

A 5 millimeter diameter punch was used to mark the area for debridement.

Subsequently, a superficial debridement was performed in the ocular surface (without penetrating into the corneal stroma) with a PVA spear. Finally, an inoculation of LPS from *Serratia marcescens* was performed in the RE leaving 10 seconds for its absorption. This protocol was carried out by the same surgeon (Day 0, 1 and 2) in all the animals of the study.

Follow-up was performed by pachymetry and slit lamp to assess the feasibility of the ocular inflammation model at least once per day. Clinical score as described below was registered during this phase.

During the creation of the inflammatory ocular model, there were no intra or postoperative complications. Anesthetic recovery was uneventful in all cases. Chemosis and conjunctival congestion were obtained as well as ocular dense exudate and corneal edema. The arrows in FIG. 14A indicate blepharitis, chemosis and ocular dense exudate. The arrow in FIG. 14B indicates details of the congested palpebral conjunctiva vessels. Fluorescein stain was used to quantify the corneal ulcer size at different times prior to subconjunctival injection of the exosomes, as shown in FIGS. 15A (Group A), 15B (Group B) and 15C (Group C) for each group at Day 2.

FIGS. 14A-B and 15A-C, and the data obtained in Phase I, confirmed that the combination of corneal epithelial abrasion and LPS from *Serratia marcescens* inoculation induced strong conjunctivitis and corneal edema in the rabbit ocular keratitis model, which were necessary to assess the performance of exosomes.

Phase II (Day 2) (4-6 Hours after $3^{rd}$ LPS Administration)

General anesthesia was obtained using the above-described protocol.

Pre-procedural pachymetry and slit lamp were performed to measure the ulcer area (baseline area) and assess corneal inflammation.

Two subconjunctival injections of extracellular vesicles or Plasmalyte were performed in the RE. Animals were divided in 3 groups of 6 rabbits each:
  Group A: Plasmalyte injection (total volume 100 µl);
  Group B: Extracellular vesicles injection (low dose, 40 µg) (total volume 100 µl);
  Group C: Extracellular vesicles injection (high dose, 200 µg) (total volume 100 µl).

For administration according to each group, each eye (RE) received one injection in the superotemporal quadrant (50 µl) and another in the inferonasal quadrant (50 µl), underneath the conjunctiva (not sub-Tenon's). For this, a 30G needle was used and advanced at least 5 mm from the site of the needle entry to prevent reflux of fluid through the hole.

Animals were then allowed to recover from anesthesia and returned to the animal housing facility, where they were checked daily by a veterinarian to assess their clinical state and presence of pain.

The effect of the exosome preparations on various clinical and histological parameters were determined essentially as described in T. McDonald and J. A Shadduck, Eye irritation in Advances in Modern Toxicology: Dermatoxicology, F. Marzulli and H. IMaibach, Eds., pp. 579-582, Hemisphere Publishing Corporation, Washington, DC, USA, 1977. The results indicate that high dose exosomes are superior to vehicle both clinically and histologically, across various parameters including conjunctivitis, corneal edema, corneal wound healing, and inflammation (FIGS. 6-12).

Pachymetry, slit lamp and fluorescein staining were monitored during the study (Days 3, 4 and 5).

Follow-up included Schirmer test, photophobia, corneal thickness measurements, corneal scarring evolution, clinical score, and food and water intake.

Figure 40:
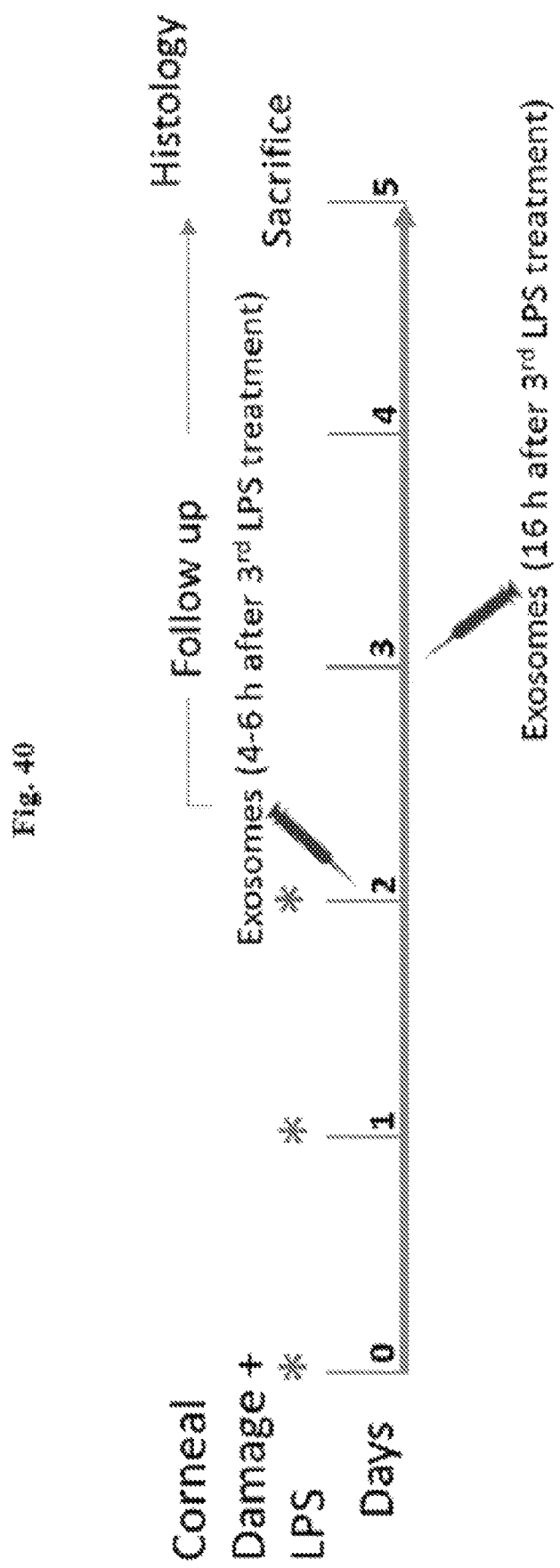
FIG. 40 schematically depicts the study design for evaluating the efficacy of CDC-EVs in acute LPS keratitis rabbit model.

Alternatively, Phase II of this study may be performed on Day 3 (e.g., 16 hours after 3rd LPS administration), as illustrated in FIG. 40.

Further alternatively, keratitis may be induced in this animal model without using LPS, i.e., with only abrasion.

A) Schirmer Test

Figure 16B:
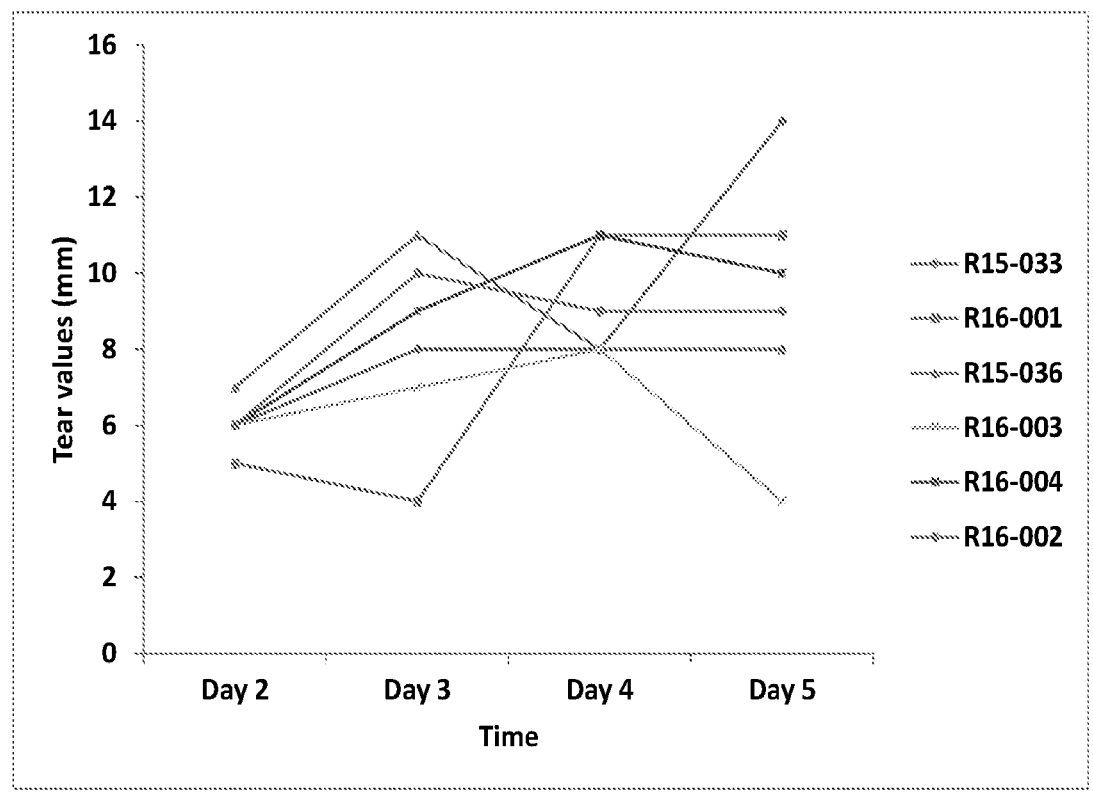
FIG. 16B shows tear production evolution in Group B (low-dose exosomes) animals.
Figure 16C:
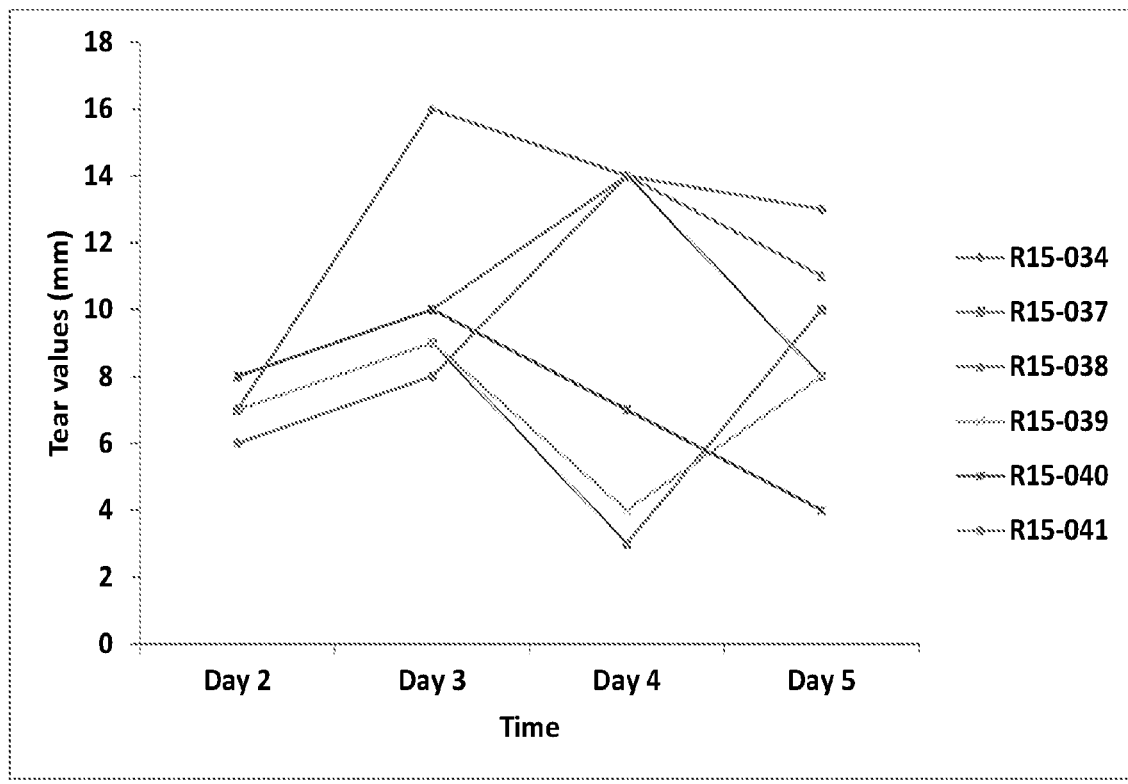
FIG. 16C shows tear production evolution in Group C (high-dose exosomes) animals.

The evolution of the amount of tear was measured using the Schirmer test. No abnormalities were detected in tear production with parameters remaining within clinically acceptable ranges. There were individual cases of increased tear production that remain within normal ranges in the eyes suffering from conjunctivitis and corneal ulcers (FIGS. 16A-C).

B) Corneal Thickness Measurements

The evolution in corneal thickness was measured by pachymetry (µm). An increase in corneal thickness reflects the amount of fluid in the cornea. Tables 13A-C show the values for Groups A-C, respectively.

TABLE 13A

| Rabbit # | Day 0 | Day 1 | Day 2 | Day 2 (after) | Day 3 | Day 4 | Day 5 |
|---|---|---|---|---|---|---|---|
| 005 | 394 | 597 | 681 | 677 | 716 | 641 | 558 |
| 006 | 398 | 555 | 683 | 672 | 639 | 677 | 680 |
| 008 | 372 | 501 | 725 | 718 | 677 | 572 | 561 |
| 009 | 397 | 593 | 728 | 665 | 608 | 481 | 449 |
| 010 | 392 | 427 | 621 | 663 | 593 | 465 | 441 |
| 011 | 379 | 616 | 604 | 654 | 573 | 508 | 510 |

TABLE 13B

| Rabbit # | Day 0 | Day 1 | Day 2 | Day 2 (after) | Day 3 | Day 4 | Day 5 |
|---|---|---|---|---|---|---|---|
| 033 | 453 | 712 | 669 | 734 | 823 | 888 | 883 |
| 001 | 415 | 665 | 739 | 745 | 763 | 774 | 795 |
| 036 | 394 | 653 | 682 | 652 | 701 | 473 | 407 |
| 003 | 384 | 421 | 697 | 726 | 697 | 444 | 494 |
| 004 | 381 | 696 | 670 | 690 | 720 | 672 | 716 |
| 002 | 427 | 632 | 636 | 670 | 696 | 743 | 560 |

TABLE 13C

| Rabbit # | Day 0 | Day 1 | Day 2 | Day 2 (after) | Day 3 | Day 4 | Day 5 |
|---|---|---|---|---|---|---|---|
| 034 | 489 | 538 | 751 | 877 | 849 | 538 | 510 |
| 037 | 494 | 634 | 673 | 661 | 738 | 524 | 502 |
| 038 | 419 | 595 | 686 | 752 | 750 | 557 | 567 |
| 039 | 387 | 511 | 673 | 687 | 685 | 586 | 558 |
| 040 | 386 | 481 | 601 | 703 | 448 | 401 | 436 |
| 041 | 404 | 567 | 687 | 726 | 749 | 689 | 758 |

Table 13D shows mean values±standard deviation (µm) obtained in pachymetry measurements from all groups over time.

TABLE 13D

|  | Day 2 (preinj) | Day 3 | Day 4 | Day 5 |
|---|---|---|---|---|
| Group A | 674.83 ± 22.57 | 634.33 ± 54.18 | 557.33 ± 87.54 | 533.17 ± 88.39 |
| Group B | 702.83 ± 37.72 | 733.33 ± 50.71 | 665.67 ± 175.18 | 642.50 ± 184.83 |
| Group C | 734.33 ± 76.59 | 703.17 ± 135.80 | 549.17 ± 93.47 | 555.17 ± 109.87 |

Figure 36:
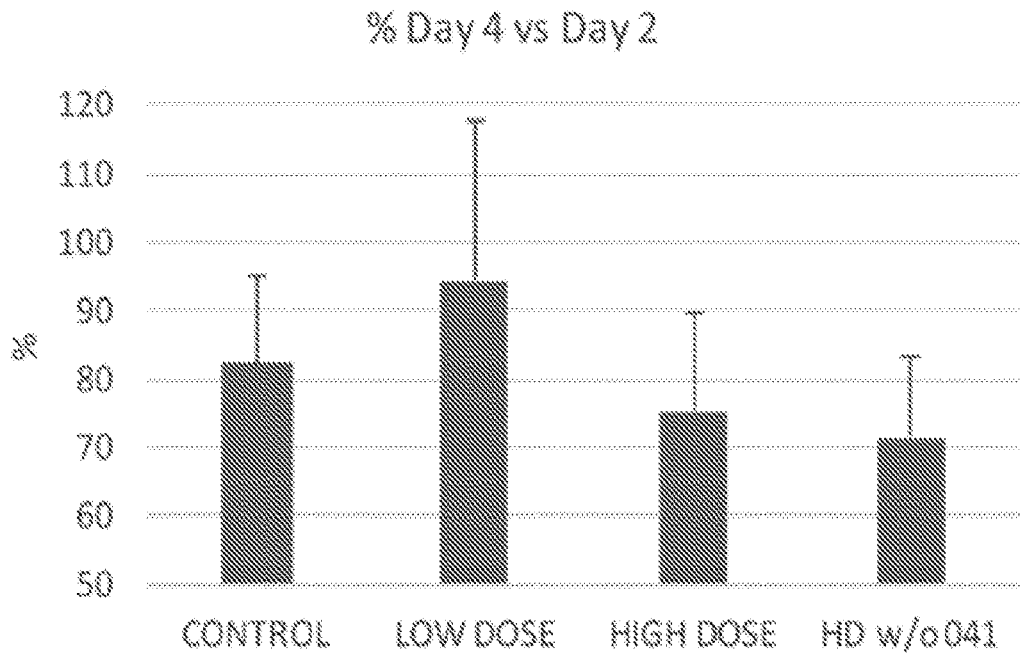
FIG. 36 depicts levels of pachymetry in the vehicle, low-dose exosome, and high-dose exosome treated rabbits at Day 4 versus Day 2. A greater reduction in corneal thickness analyzed by pachymetry was observed in the high-dose exosome group when compared with control group.

FIG. 36 graphically shows a greater reduction in corneal thickness at Day 4 versus Day2 in Group C (high dose of exosomes; 24.7% reduction) compared to Group A (vehicle control; 17.5% reduction), especially when the outlier Rabbit #041 was excluded from the analysis (almost 30% reduction).

C) Corneal Ulcer Size

Corneas were stained with fluorescein solution. Images were processed using the ImageJ program 1.440 (National Institutes of Health, USA). The evolution in corneal ulcer size was measured by slit lamp. Tables 14A-C show the % of affected cornea for Groups A-C, respectively.

TABLE 14A

| Rabbit # | Day 2 (aft) | Day 3 | Day 4 | Day 5 |
|---|---|---|---|---|
| 005 | 40.34 | 2.32 | 5.65 | Diffuse staining |
| 006 | 39.74 | 4.05 | 7.29 | 8.80 |
| 008 | 30.28 | 3.88 | Diffuse staining | Diffuse staining |
| 009 | 35.62 | 2.17 | Diffuse staining | Diffuse staining |
| 010 | 33.82 | 0.35 | Diffuse staining | Diffuse staining |
| 011 | 26.66 | 3.32 | 1.31 | Diffuse staining |

TABLE 14B

| Rabbit # | Day 2 (aft) | Day 3 | Day 4 | Day 5 |
|---|---|---|---|---|
| 033 | 29.57 | 23.45 | 29.61 | 15.33 |
| 001 | 39.35 | 11.61 | 10.95 | 13.83 |
| 036 | 25.99 | 8.17 | Diffuse staining | Diffuse staining |
| 003 | 34.02 | 20.70 | Diffuse staining | Diffuse staining |
| 004 | 46.03 | 15.46 | 15.33 | 11.45 |
| 002 | 23.01 | 10.41 | 4.39 | 6.56 |

TABLE 14C

| Rabbit # | Day 2 (aft) | Day 3 | Day 4 | Day 5 |
|---|---|---|---|---|
| 034 | 27.21 | 6.87 | Diffuse staining | Diffuse staining |
| 037 | 30.98 | 15.87 | 1.36 | 13.83 |
| 038 | 28.70 | 11.27 | Diffuse staining | Diffuse staining |
| 039 | 24.99 | 11.92 | Diffuse staining | Diffuse staining |
| 040 | 28.76 | 10.63 | Diffuse staining | 0.00 |
| 041 | 29.46 | 12.67 | 15.05 | 4.29 |

Table 14D shows mean values±standard deviation (% of affected area).

TABLE 14D

| | Day 2 (preinj) | Day 3 | Day 4 | Day 5 |
|---|---|---|---|---|
| Group A | 34.41 ± 5.34 | 2.68 ± 1.38 | 4.74 ± 3.08 | 8.79* |
| Group B | 29.20 ± 15.87 | 14.96 ± 6.05 | 15.07 ± 10.69 | 11.79 ± 3.83 |
| Group C | 28.35 ± 2.05 | 11.54 ± 2.93 | 8.20 ± 9.69 | 2.14 ± 3.03 |

*indicates that, in this group and time, only one eye had measurable ulcer, therefore no standard deviation can be obtained (n = 1).

In summary, an apparent deceleration could be observed in corneal ulcer healing in the groups treated with extracellular vesicles versus the group receiving Plasmalyte injection on the post-administration day. After that, the 3 study groups followed a similar pattern with a trend towards greater epithelial recovery in the animals treated with high dose of extracellular vesicles.

Figure 37:
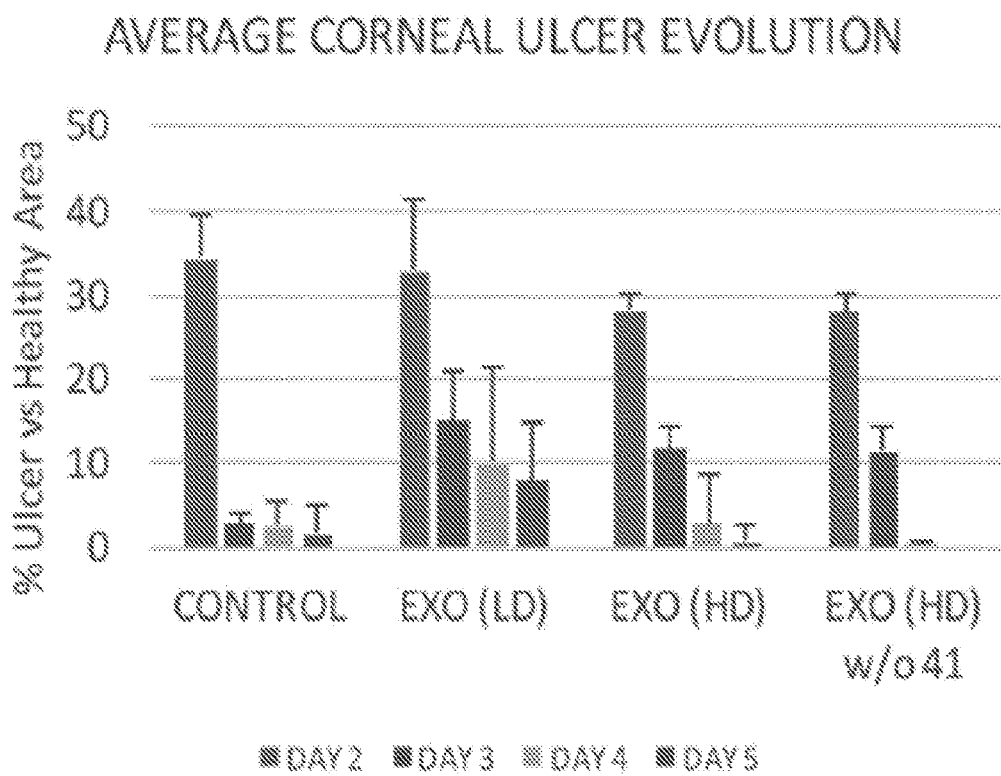
FIG. 37 depicts average corneal ulcer evolution in the vehicle, low-dose exosome, and high-dose exosome treated rabbits at Days 2, 3, 4, and 5.
Figure 38:
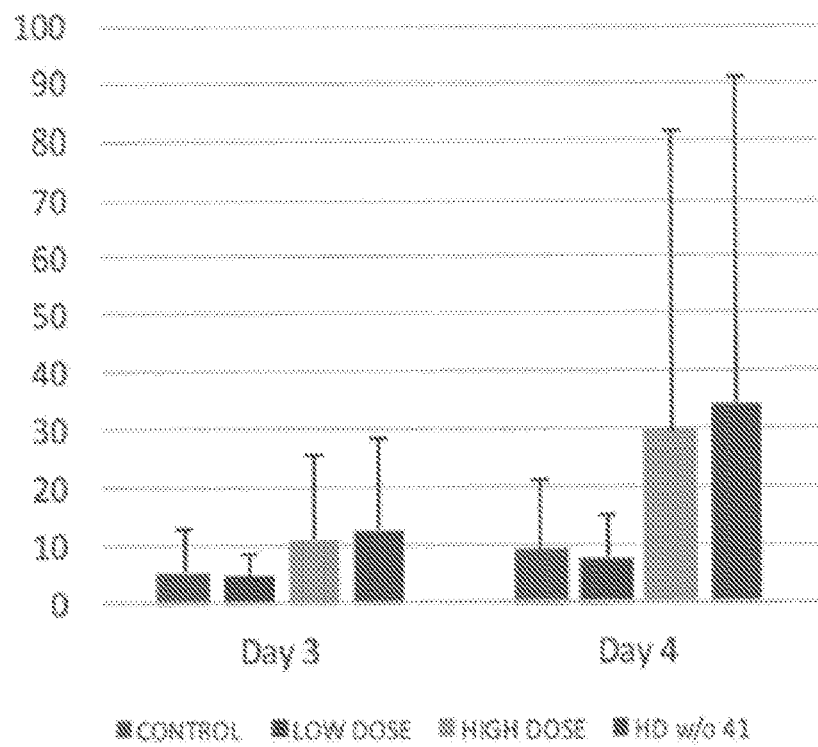
FIG. 38 depicts fold food intake versus basal in the vehicle, low-dose exosome, and high-dose exosome treated rabbits at Days 3 and 4.
Figure 39:
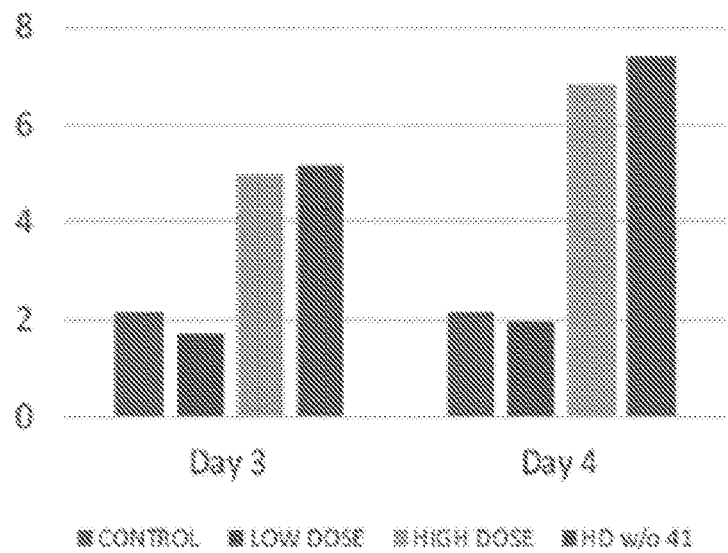
FIG. 39 depicts fold water intake versus basal in the vehicle, low-dose exosome, and high-dose exosome treated rabbits at Days 3 and 4.

FIG. 37 graphically shows that the three study groups followed a similar pattern with a trend towards greater epithelial recovery in Group C (high-dose exosomes), especially when the outlier Rabbit #041 was excluded from the analysis.

D) Clinical Conjunctivitis Score

The animals were assessed 2 days after treatment (Day 4) on a 4-point scale for global conjunctival hyperemia, chemosis and discharge, and the results are summarized in Table 15.

TABLE 15

| | Rabbit # | Day 2 | Day 4 |
|---|---|---|---|
| Group A | 005 | 3 | 3 |
| | 006 | 3 | 3 |
| | 008 | 3 | 2 |
| | 009 | 3 | 2 |
| | 010 | 3 | 2 |
| | 011 | 3 | 2 |
| Group B | 033 | 3 | 2 |
| | 001 | 3 | 3 |
| | 036 | 3 | 1 |
| | 003 | 3 | 3 |
| | 004 | 3 | 3 |
| | 002 | 3 | 2 |
| Group C | 034 | 3 | 2 |
| | 037 | 3 | 1 |
| | 038 | 3 | 1 |
| | 039 | 3 | 1 |
| | 040 | 3 | 1 |
| | 041 | 3 | 3 |

The proportion of the animals with a 2-step (on 4-point scale) improvement in clinical conjunctivitis score between immediately before treatment (Day 2) and 2 days after (Day 4) vehicle or exosome delivery was: 0% (0/6 rabbits) for Group A (vehicle control), 16.7% (1/6 rabbits) for Group B (low-dose exosomes), and 66.7% (4/6 rabbits) for Group C (high-dose exosomes).

The average degree of improvement of clinical conjunctivitis score between immediately before treatment (Day 2) and 2 days after (Day 4) vehicle or exosome delivery was: −0.67 for Group A (vehicle control), −0.67 for Group B (low-dose exosomes), and −1.50 for Group C (high-dose exosomes).

Table 16 shows mean values of clinical conjunctival scores, wherein a statistically significant difference was seen on Day 4 between Group C (high-dose exosomes) and Group A (Plasmalyte injection) (p=0.047), indicating less conjunctival affectation in Group C than Group A

TABLE 16

| | Day 2 (preinject) | Day 3 | Day 4 | Day 5 |
|---|---|---|---|---|
| Group A | 3.00 | 2.67 | 2.33 | 0.83 |
| Group B | 3.00 | 2.17 | 2.33 | 1.83 |
| Group C | 2.67 | 2.83 | 1.5 | 1.17 |

E) Clinical Corneal Edema Score

Table 17 shows that a statistically significant difference in the clinical corneal edema score was seen on Day 4 between Group C (high-dose exosomes) and Group A (Plasmalyte injection) (p=0.011), indicating less corneal affectation in Group C than Group A.

TABLE 17

| | Day 2 (preinject) | Day 3 | Day 4 | Day 5 |
|---|---|---|---|---|
| Group A | 1.00 | 1.83 | 2.00 | 1.83 |
| Group B | 1.00 | 1.00 | 1.33 | 1.00 |
| Group C | 1.00 | 1.5 | 1.83 | 1.17 |

F) Food and Water Intake

Food and water intake were analyzed as surrogate markers of ocular pain. See, e.g., Recognition and assessment of pain and distress, Pennsylvania University (2000); Guidelines on anesthesia and analgesia in laboratory animals, University of South Florida (2007). The majority of the animals showed decreased food intake during Phase I, consistent with the expected discomfort caused by the epithelial abrasion. From Day 3 onwards, the animals' food intake increased, showing a pain reduction and a positive recovery.

Figure 17A:
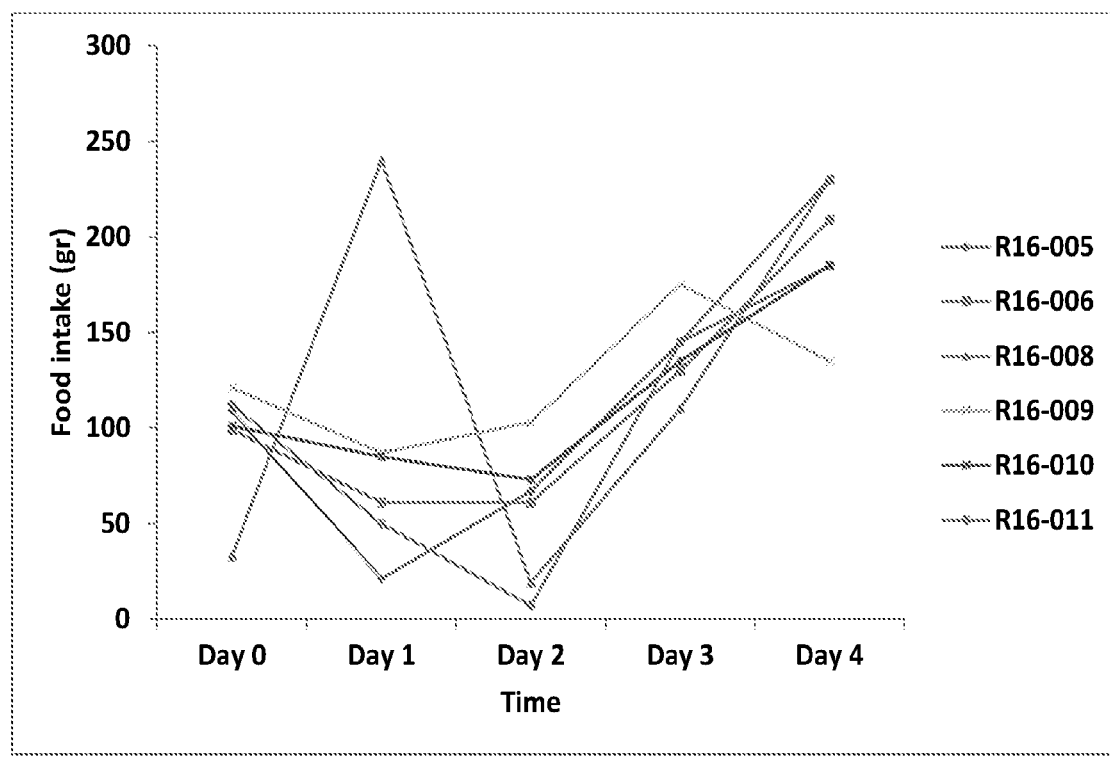
FIG. 17A shows food intake evolution in Group A (vehicle control) animals.
Figure 17B:
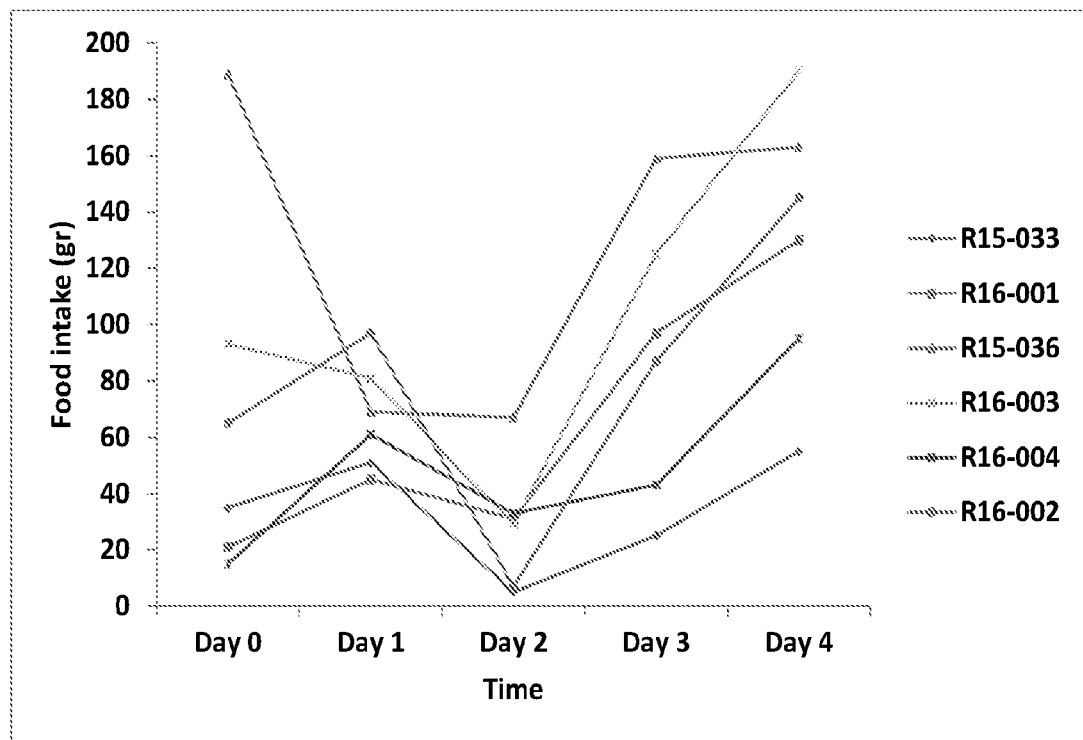
FIG. 17B shows food intake evolution in Group B (low-dose exosomes) animals.
Figure 17C:
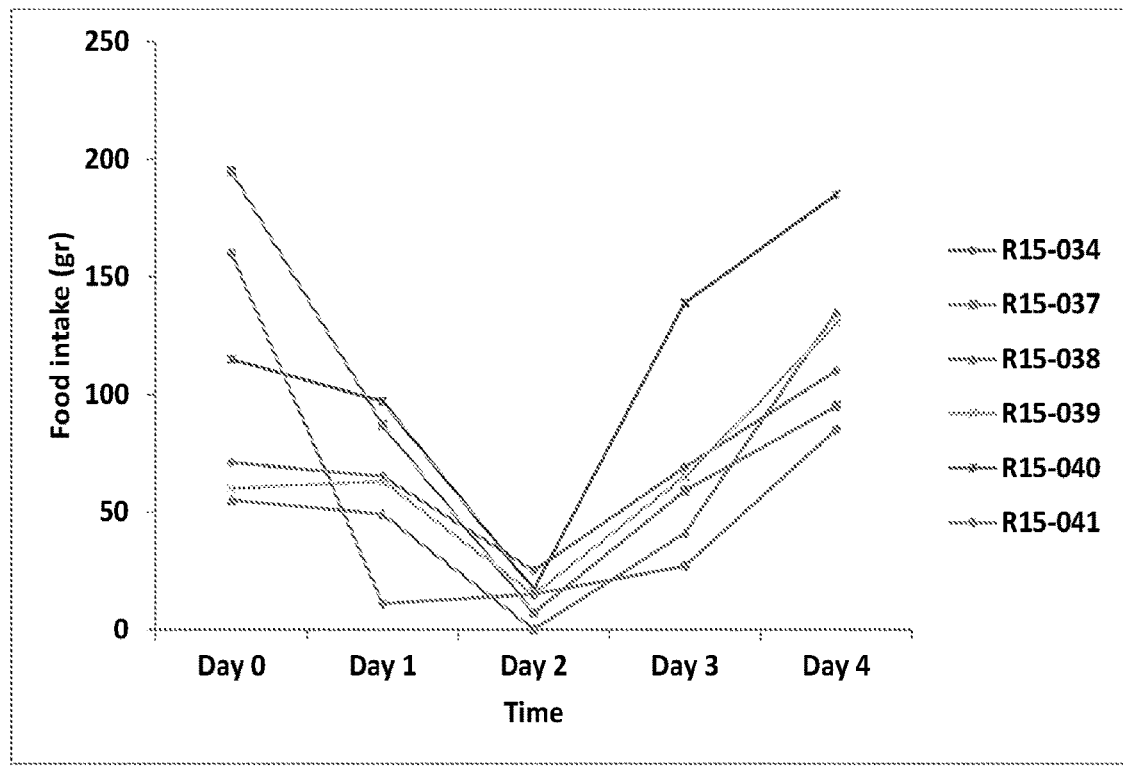
FIG. 17C shows food intake evolution in Group C (high-dose exosomes) animals.
Figure 18:
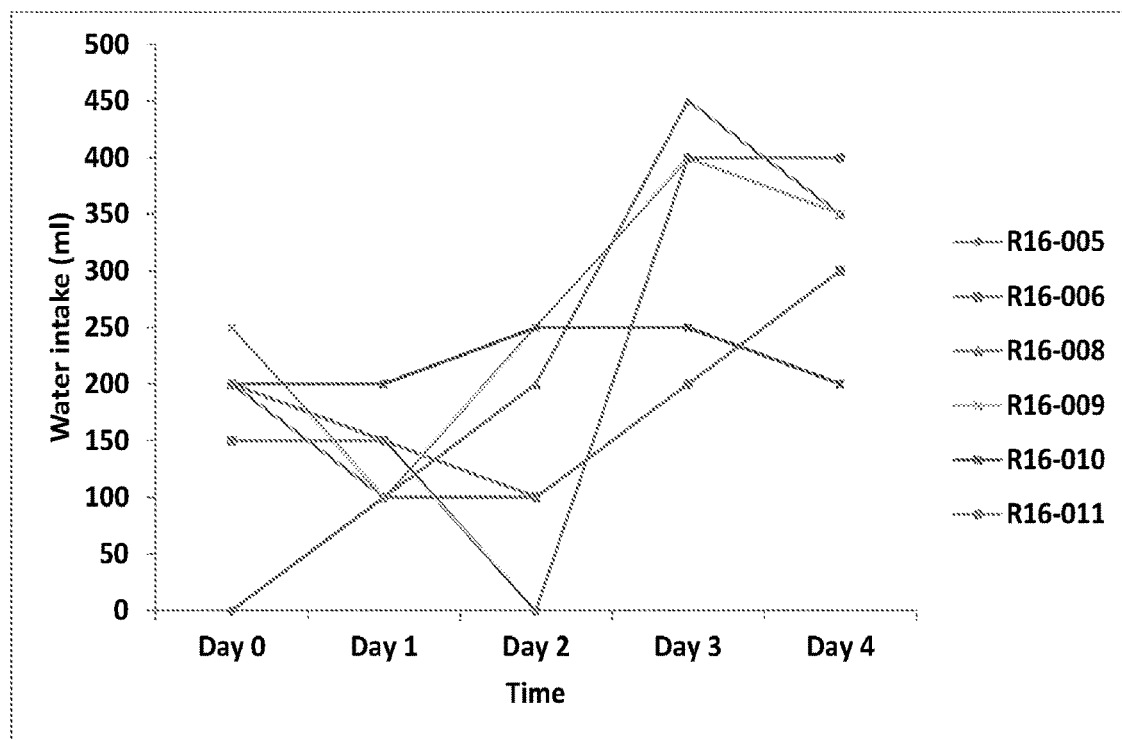
FIG. 18 shows water intake evolution in Group A (vehicle control) animals.
Figure 19:
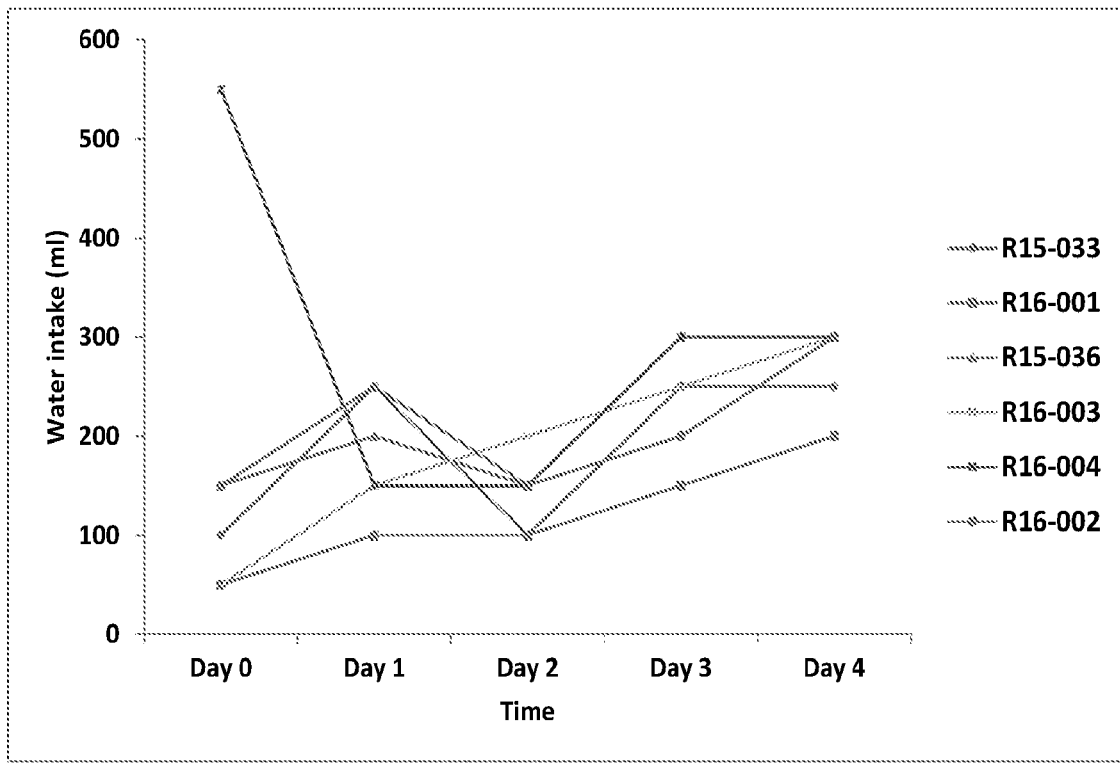
FIG. 19 shows water intake evolution in Group B (low-dose exosomes) animals.
Figure 20:
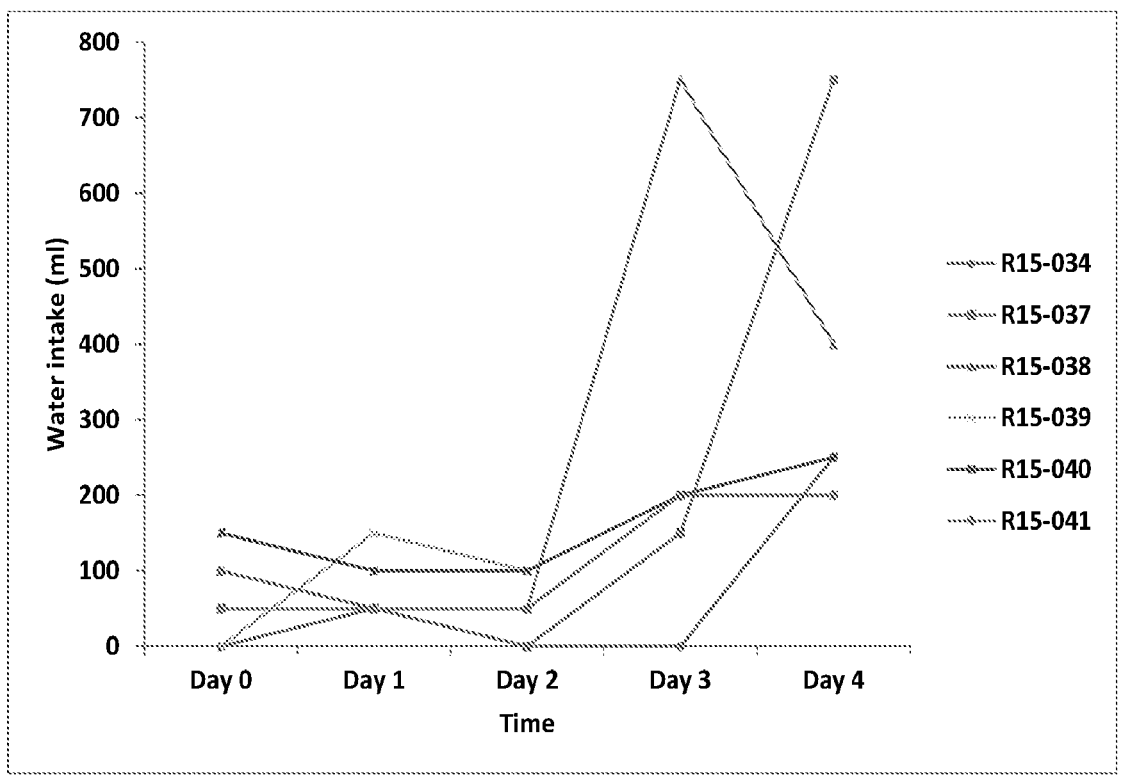
FIG. 20 shows water intake evolution in Group C (high-dose exosomes) animals.

FIGS. 17A-C graphically show the food intake evolution for Groups A-C, respectively. FIGS. 18A-C graphically show the water intake evolution for Groups A-C, respectively. FIGS. 9 and 10 show that Group C (high-dose exosomes) showed a trend toward being superior compared to Group A (vehicle control) at Day 4 (2 days after exosome administration), especially when the outlier Rabbit #041 was excluded from the analysis.

G) Histological Evaluation

At day 5, animals were sacrificed. The right eyes and parotid lymph nodes (right side) of the animals were analyzed using hematoxylin and eosin (HE) or Masson's trichrome stain (MTC) in order to evaluate the grade of fibrosis in the analyzed samples. Slides were microscopically examined for histological lesions or cellular infiltration in the affected area of the eyes. A grading score of lesions was established on a 0-4 scale as: 0 being no changes or within normal limits, 1 being slight, 2 being mild, 3 being moderate, and 4 being severe, with the results summarized in Table 18 showing the mean values of histological lesions score.

TABLE 18

| | Group A | Group B | Group C |
|---|---|---|---|
| Cornea | | | |
| Detachment epithelium | 2.5 | 2 | 1.17 |
| Inflammatory cell infiltrate | 1.5 | 1.67 | 1.67 |
| Edema | 0.17 | 0 | 0 |
| Reactive endothelium | 0 | 0 | 0 |
| Fibrosis | 0.33 | 0 | 0.83 |
| Necrosis | 0.17 | 0.5 | 0 |
| Iris/ciliary bodies | | | |
| Inflammatory cells infiltrate | 1.5 | 1.67 | 1.5 |
| Edema | 1.67 | 1 | 1.33 |
| Congestion | 0.17 | 0.17 | 0 |
| Fibrosis | 1 | 0.83 | 0.67 |
| Hemosiderin deposition | 0 | 0 | 0 |
| Bulbar conjunctiva | | | |
| Inflammatory cells infiltrate | 2.17 | 2.17 | 1.83 |
| Fibrosis | 2.83 | 2.17 | 2.67 |
| Edema | 1.5 | 1.33 | 1.5 |
| Hemorrhage | 1.83 | 0.33 | 0.17 |
| Retina | | | |
| Detached | 0.5 | 0.33 | 0 |
| Degeneration | 0.67 | 0.17 | 0.67 |
| Vascular proliferation | 0 | 0 | 0 |
| Total score | 18.5 | 14.3 | 14.0 |

Group a (Vehicle Control)

In Group A, the corneas showed detachment of the epithelium higher than 75% of the corneal surface in 2/6 animals and higher than 50% in another one. In addition, a mild inflammatory cell infiltration was observed in 3 corneas. The detected inflammation infiltration was consistent with the presence of corneal edema. FIGS. 21A-D show detachment of epithelial cells, fibrosis and mild infiltrate of inflammatory cell in the stroma, in Rabbit #005.

Group B (Low-Dose Exosomes)

In Group B, the corneas showed detachment of the epithelium higher than 50% of the corneal surface in 3/6 animals, but in the rest the loss of epithelial cells was below 25%. The affected area of the cornea was lower than in Group A, as shown in FIGS. 22A-D for Rabbit #004.

Group C (High-Dose Exosomes)

In Group C, only 3 eyes showed loss of epithelial cells of the cornea, which was moderate, as shown in FIGS. 23A-D for Rabbit #037, indicating a greater recovery of this layer. One of the evaluated eyes in Rabbit #040 had a full recovery of the epithelial layer, as shown in FIGS. 24A-D.

In summary, although detachment in the corneal epithelium and inflammatory cell infiltrate were observed in the 3 groups, those finding were more severe in Group A (vehicle control). None of the animals in Group B (low-dose exosomes) and Group C (high-dose exosomes) showed higher than 75% of detachment. In fact, 3/6 rabbits in Group C (high-dose exosomes) exhibited complete corneal epithelial regeneration, and another one had an epithelial defect comprising less than 25% of the corneal surface.

In the iridocorneal angles, the most frequent morphological findings were fibrosis in the bulbar conjunctive that was present in the 3 groups and in the majority of analyzed eyes. The inflammatory cell infiltration and edema in the bulbar conjunctive and ciliary bodies were also common. However, the severity of most of these lesions was higher in Group A (vehicle control), as shown in FIGS. 25A-F for Rabbit #005, than in Group B (low-dose exosomes) and Group C (high-dose exosomes). In Group B (low-dose exosomes), the lesions were less severe, with cases in which inflammatory cell infiltrate was minimal, and without the presence of fibrosis, as shown in FIGS. 26A-F for Rabbit #004 and FIGS. 27A-D for Rabbit #036. Group C also had mild to moderate inflammatory infiltrate in the bulbar conjunctive, and the majority of ciliary bodies showed minimal edema or did not have fibrosis, as shown in FIGS. 28A-D for Rabbit #037, FIGS. 29A-D and 30A-D for Rabbit #040.

There was only one case in Group C of severe fibrosis on the iridocomeal angle in Rabbit #041, as shown in FIGS. 31A-D. On Day 5, this was the only animal who showed a corneal edema, chemosis, iris vessels congestion as well as severe conjunctivitis, as shown in FIG. 32. The eyelids exhibited slight alopecia and severe exudate. These signs could indicate discomfort accompanied with scratching, which may explain the presence of a defined ulcer area.

In Rabbit #039 (Group C), a cartilaginous metaplasia was observed between the stromal cells in the bulbar conjunctive, as shown in FIGS. 33A-B. However, this is a chronic lesion, and therefore probably not associated with the exosome treatment. In the retina, no lesions were observed. Only slight focal retinal detachment (probably caused by sample collection) and small isolated clusters of enlarged cells (probably hypertrophied retinal cells), which are incidental findings in the animals, were present.

Across all 17 quantitative histological analyses performed using the totality of pathology data, Group C (high-dose exosomes) showed a trend toward being superior to vehicle in 9 cases, equivalent in 5 cases, and inferior in 3 cases. Across the 12 quantitative histological analyses performed using a clinically relevant subset of pathology data, Group C (high-dose exosomes) showed a trend toward being superior to Group A (vehicle control) in 7 cases, equivalent in 4 cases, and inferior in only 1 case.

Referring to FIGS. 34A-F, the parotid lymph node of Rabbit #034 (Group C) treated with the high-dose exosomes had a smaller area (mean area: 3.52 mm2) of lymphoid tissue than Rabbit #010 (Group A) treated with vehicle (mean area: 4.69 mm2). The mean area of lymphoid tissue in the parotid lymph node was higher (10.43 mm2) in Group B (low-dose exosomes) compared with Group A (vehicle control) and Group C (high-dose exosomes). In Group C, the mean of area of lymphoid tissue was lower than the other two groups, suggesting a reduced immune reaction in lymph nodes to the administered substance.

Example 11: Efficacy of CDC-EVs in Rabbit Siogren's Model

The efficacy of extracellular vesicles derived from cardiosphere-derived cells (CDC-EVs) was evaluated in a rabbit Sjogren's model of induced mild-to-moderate dry eye disease (DED). This model produces a very mild form of autoimmune inflammatory DED with moderate variability between eyes and between animals in clinical measures of ocular surface staining and tear production.

CDCs from a donor line were conditioned in serum-free medium for 15 days at 37° C. and 5% O2. The conditioned media was collected, filtered through 0.45 μm filter, and concentrated using 10 kDa Centricon Plus-70 Centrifugal Filter (Millipore). Sample was diafiltrated with PlaymaLyte A. After concentrating, CDC-EV sample was filtered through a 0.22 μm filter. Protein concentration was measured using DC assay (Biorad).

Figure 11:
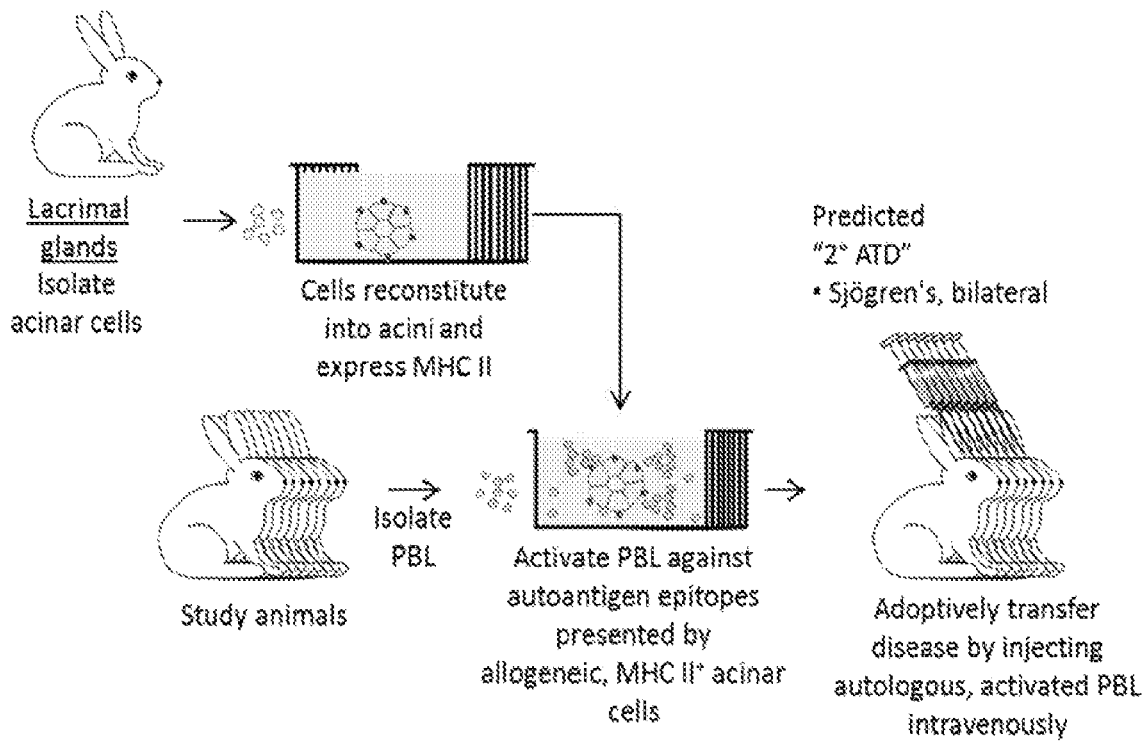
FIG. 11 illustrates the adoptive transfer rabbit model of inflammatory autoimmune dry eye syndrome, wherein autologous peripheral blood lymphocytes activated against lacrimal gland autoantigens were adoptively transferred into study animals using intravenous administration, leading to mild-to-moderate autoimmune inflammatory dry eye disease.

As shown in FIG. 11, inflammatory autoimmune DED was adoptively transferred (AT) to 6 rabbits by intravenous injection of autologous peripheral blood lymphocytes (PBLs) that had been activated ex vivo against lacrimal gland (LG) acinar cell autoantigens. Microparticles, which include exosomes that LG acinar cell secrete constitutively, are naturally microencapsulated samples of autoantigens from both the cytosol and the cells' membrane-bounded compartments. Microparticles were isolated from supernatant primary culture medium and used as the source of autoantigens for dendritic cells (mDCs) that were matured from bone marrow monocytes and stimulated with LPS. PBLs were isolated from study animals (n=6); activated in ex vivo mixed cell reactions with MP-primed mDCs; then reintroduced by injection via marginal ear veins. As PBLs were reintroduced autologously, any inflammatory process they transferred would be autoimmune.

CDC-EVs were delivered to the right eye of each animal (OD) with 2 subconjunctival injections per eye (one into superotemporal quadrant, the other into inferonasal quadrant) of 50 μL each (100 μL total per eye), at a concentration of 4 mg/mL). Plasmalyte vehicle was delivered to the left eye of each animal (OS) with 2 injections subconjunctival per eye of 50 μL each (100 μL total per eye). Injections were performed at 12 (Rx1) and 24 (Rx2) weeks after AT, corresponding to peaks of corneal Rose Bengal staining.

Ocular surface status was evaluated by Rose Bengal staining using the modified van Bijsterveld schema and Schirmer I tear production tests (STT-1) 1 day prior to Rx1 and at biweekly intervals through week 28 post AT. For Rose Bengal staining, intensity was scored in 2 exposed conjunctival zones (nasal and temporal) and cornea with a score of 0-3 for each zone, adding to a maximum score 9 at each time point.

Significance of differences between right (CDC EV-treated) and left (PlasmaLyte vehicle-treated) eyes was determined using student's T-test versus vehicle with p<0.05.

Figure 12A:
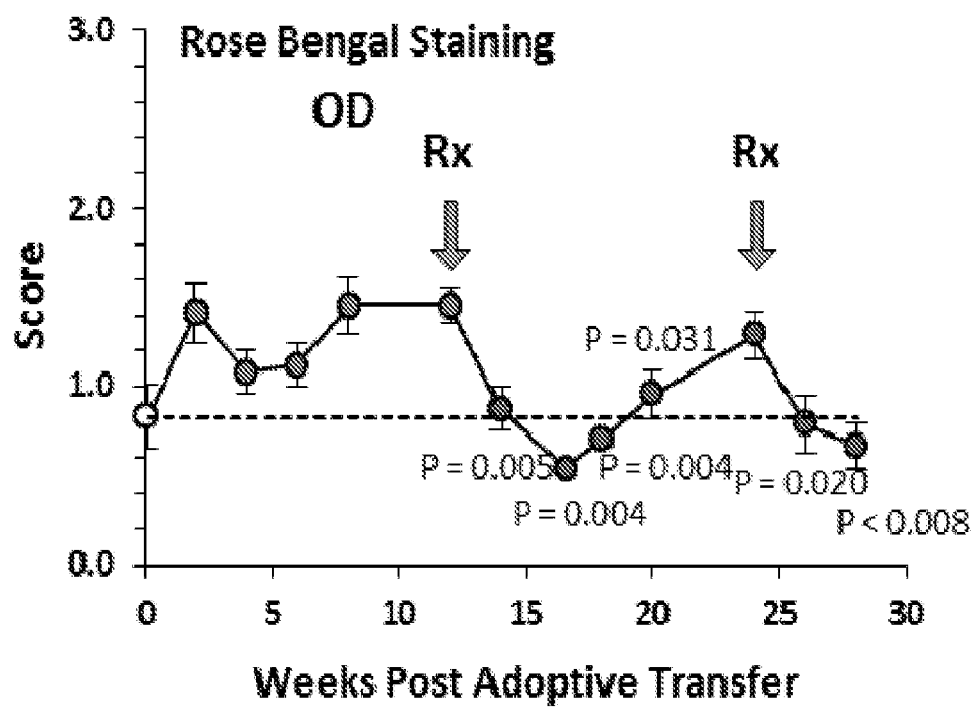
FIGS. 12A-B graphically show the mean Rose Bengal scores after adoptive transfer by IV injection of autologous, MCR (mixed cell reaction)-activated peripheral blood lymphocytes and two subconjunctival treatments with CDC-EVs (OD eyes) and vehicle (OS eyes). For approximately four weeks after each subconjunctival injection of CDC-EVs into OD eyes, there was a significant reduction in Rose Bengal staining score, whereas such a significant difference was not detected in OS eyes of the same animals, which received injections of vehicle. P-values are shown at significant time points.
Figure 12B:
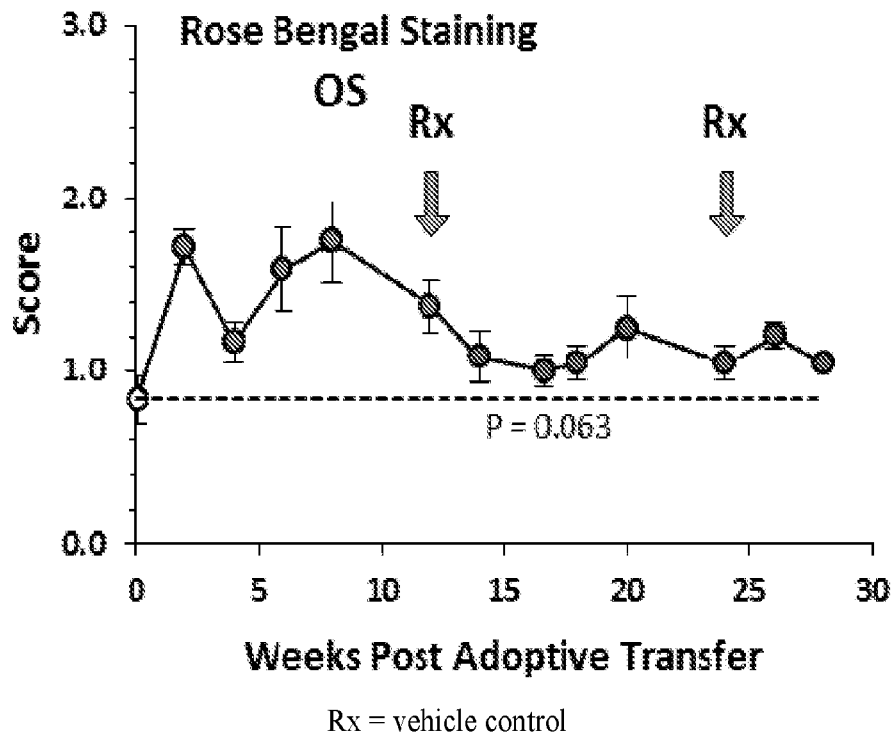

One eye with high baseline Rose Bengal score (1.5) and low STT-1 score (6.0 mm/min) was excluded as spontaneously diseased. Ocular surface inflammation developed over bi-phasic time-courses in the remaining 11 eyes. By week 2, Rose Bengal scores were increased from 0.8±0.1 to 1.6±0.1. Mean scores then subsided but recrudesced by week 8. By week 12, Rose Bengal scores remained elevated (1.5±0.1) in 10 eyes and returned to baseline in 1 eye (FIGS. 12A-B). Mean Rose Bengal scores across both OD and OS eyes reached peak levels of approximately 1.5 by week 12 after AT. For approximately four weeks after each subconjunctival injection of CDC-EVs into OD eyes, there was a significant reduction in Rose Bengal staining score, whereas such a significant difference was not detected in OS eyes of the same animals, which received injections of vehicle. P-values are shown at significant time points.

Figure 13A:
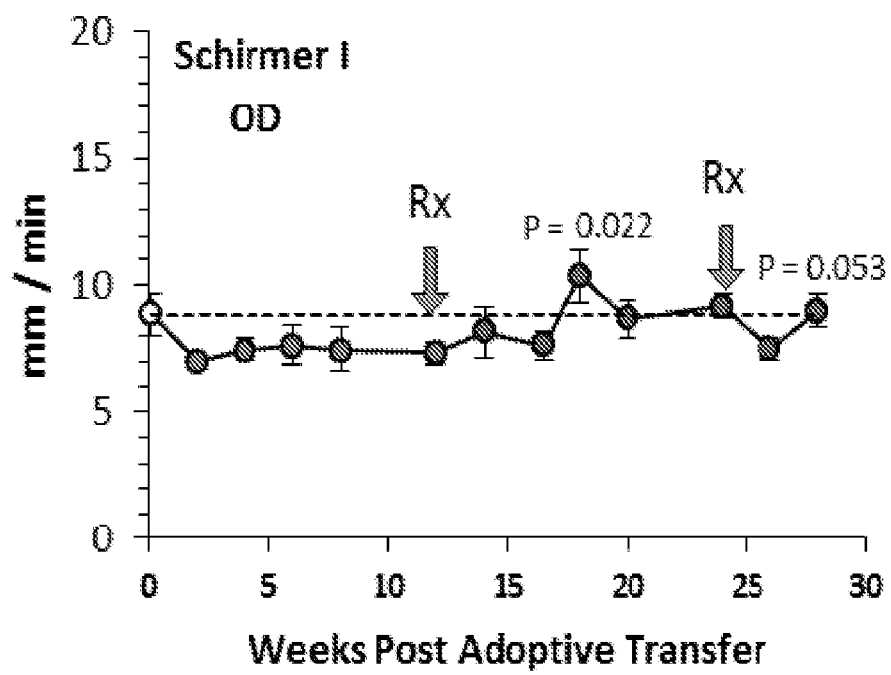

By week 2, STT-1 scores were decreased in 8 eyes (9.8±0.4 mm to 6.4±0.4 mm), unchanged in 2 eyes, and increased 1.0 mm above baseline in 1 eye. By week 12, STT-1 scores were decreased by 2.1±mm in 7 eyes; returned to baseline in 1 eye; increased 2.0 mm above baseline in 1 eye that had not changed at week 2; and increased 3 mm above baseline in the eye that had increased by week 2 (FIGS. 13A-B). Rx appeared to increase STT-1 scores in both eyes. The mean STT-1 increase reached statistical significance in OD (P=0.046) but not in OS (P=0.100).

As such, CDC-EVs are a promising therapy for mild-to-moderate autoimmune inflammatory DED, as well as related inflammatory diseases of the ocular surface including ocular GVDD, as they produced small yet significant increases in tear production and returned ocular surface staining to baseline in this model.

Example 12: Efficacy of CDC-EVs in Ocular GVHD Mouse Model

Figure 41:
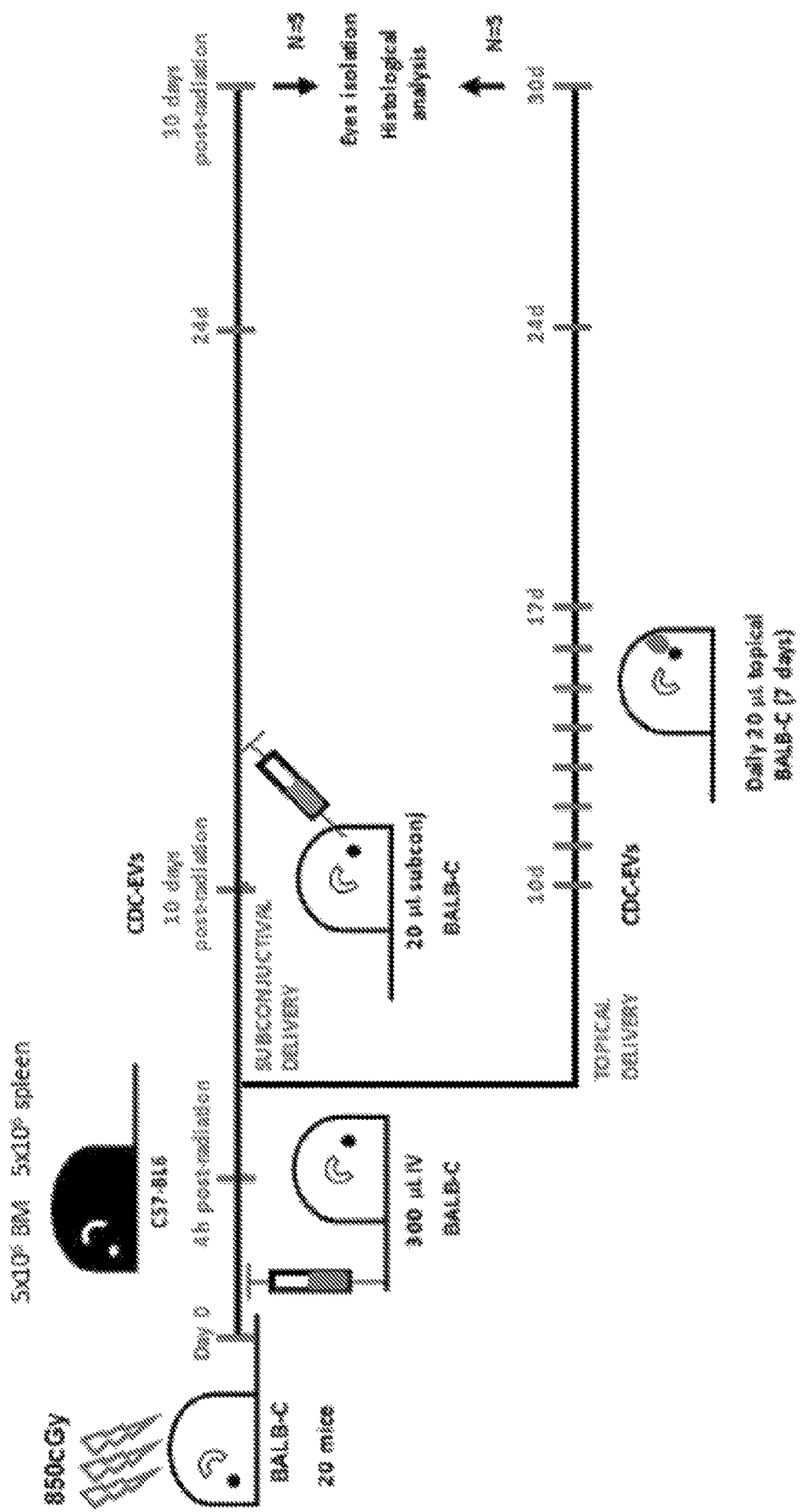
FIG. 41 schematically depicts the study design for evaluating the efficacy of CDC-EVs in acute ocular GVHD mouse model.
Figure 42:
FIG. 42 depicts subconjunctival injection delivery after subconjunctival delivery of free dye or dye-loaded exosomes (UFC) exosomes. Healthy mice were subconjunctivally injected with 7.6×107 particles labeled with DiR in a volume of 10 microliters and 1 hour later the presence of DiR in the eye was quantified using Xenogen IVIS Imaging System Control animals received the vehicle with a similar amount of DiR.
Figure 43:
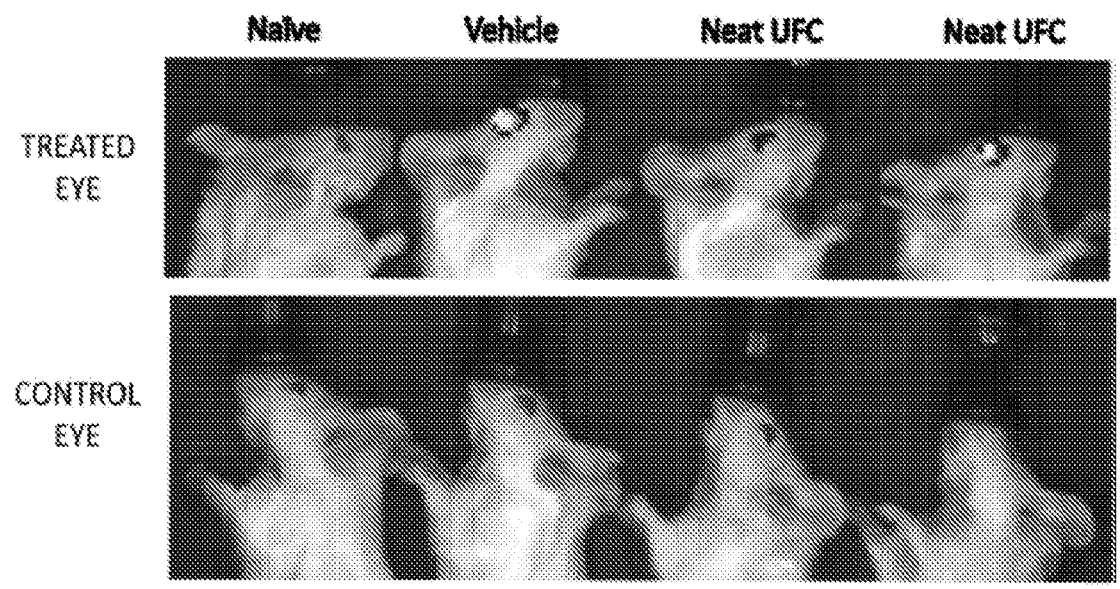
FIG. 43 depicts biodistribution at 1 hour after subconjunctival delivery to mice of free dye ("vehicle") or dye-loaded exosomes (0.5×109 exosomes, "Neat UFC") in the treated (right) and untreated (left) eyes as compared to an untreated mouse ("naïve").
Figure 44:
FIG. 44 depicts biodistribution and retention of exosomes after subconjunctival delivery. Three different amounts of exosomes containing fluorescent dye were delivered by subconjunctival injection into the eyes of the mice and the mice were assessed for fluorescence at 24 hours after administration.

The efficacy of CDC-EVs may be further evaluated in an ocular GVHD mouse model, according to the protocol design as illustrated in FIG. 41, wherein:
Balb/c mice will be radiated in two rounds with a gap of 4 hours and a total dose of 850 cGy.
After the second radiation, mice will be injected with 5×106 bone marrow cells plus 5×106 splenocytes from C57-BL6 mice in a 300 μl volume of RPMI. Three C57-BL6 mice will be used for BM and spleen cells isolation.
On day 10 after radiation each animal will undergo an ophthalmic examination. Ocular findings will be scored.
Animals will be randomized in three groups, as shown in Table 19.

TABLE 19

| GROUP | N BALB/C | RADIATION | BM CELLS | SPLEEN CELLS | ADMIN TOPICAL | ADMIN SUBCONJ |
|---|---|---|---|---|---|---|
| 1 | 8 | YES | $5 \times 10^6$ | $5 \times 10^6$ | — | — |
| 2 | 8 | YES | $5 \times 10^6$ | $5 \times 10^6$ | YES | — |
| 3 | 8 | YES | $5 \times 10^6$ | $5 \times 10^6$ | — | YES |

Subconjunctival group: mice will receive a single subconjunctival administration of CDC-EVs on day 10 after radiation.

Topical group: mice will receive daily topical administration of CDC-EVs for 7 days starting on day 10 after radiation.

Control group: mice will receive a single subconjunctival injection of vehicle in the left eye and topical administration for 7 days starting on day 10 after radiation on the right eye.

Both for subconjunctival and for topical administration, a volume of 10 µl in each delivery is proposed.

Animals will be follow up for 20 days after CDC-EV administration.

Follow up:
 Corneal epithelium stain using fluorescein
 Weight change
 Signs of GVHD will be analyzed (behavior, activity, skin and fur integrity will be analyzed using a 0-2 scale (Cooke K R et al., Blood, 15; 88(8):3230-9 (1996))
 Macroscopic analysis of both eyes will be done twice per week. Evaluate periocular fur, palpebral edge, blepharospasm using a 3 grade clinical scale (Lorenzo R., Biol Blood Marrow Transplant, 17: 270-273 (2011)) Animals will be sacrificed 20 days after treatment.

Following euthanasia, both eyes (entire globe) from all animals will be collected, enucleated, and placed into Davidson fixation buffer in individual vials. Spleen, Parotid lymph nodes, liver, lungs and kidneys will be also collected.

Figure 45:
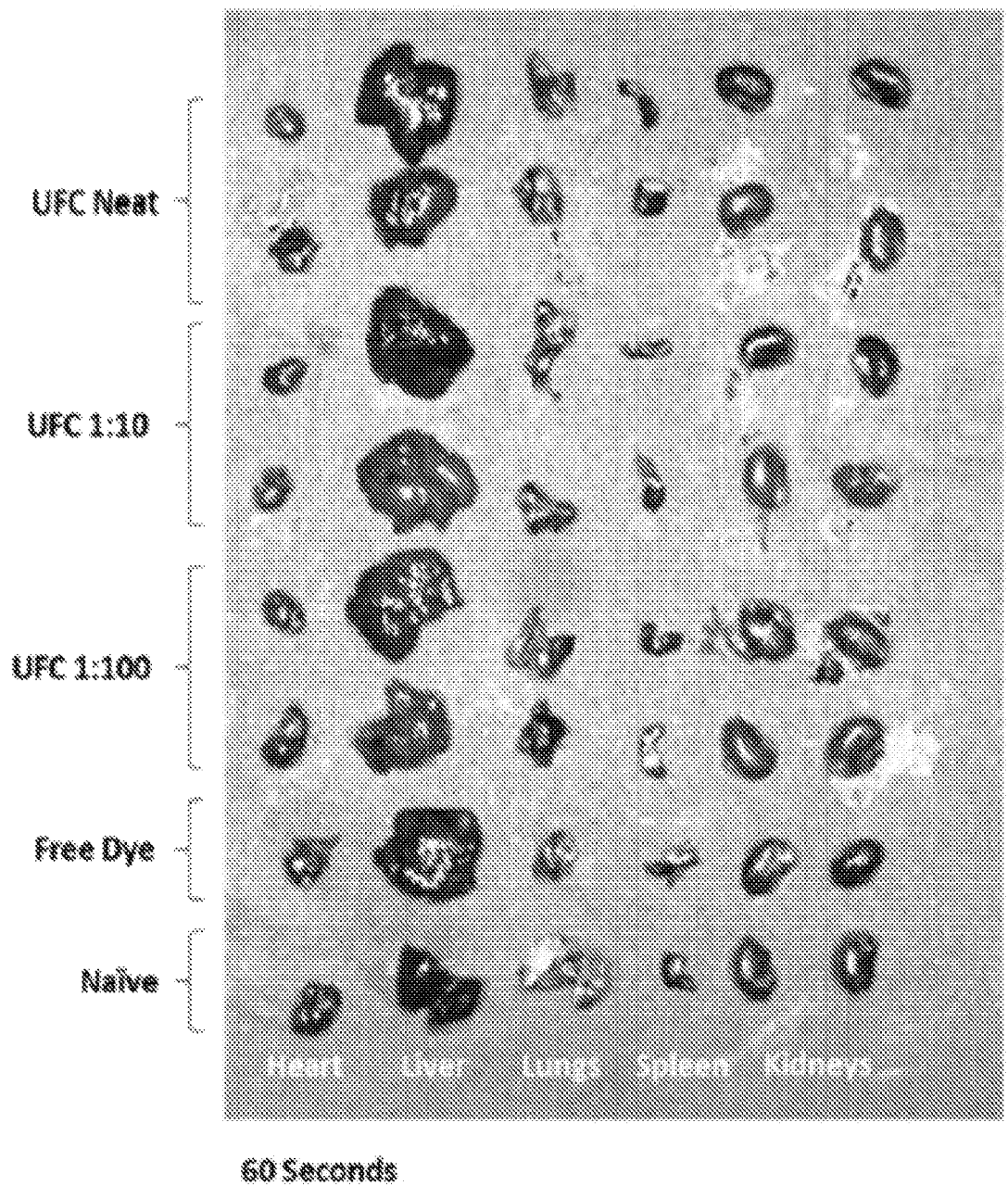
FIG. 45 depicts lack of exosomes in various organs at 24 hours after subconjunctival delivery of exosomes. Mice subconjunctivally injected with 5×108 DiR labeled particles were sacrifices 24 h after administration and DiR signal tested in the heart, liver, lungs, spleen and kidneys. DiR signal was observed in the exosome treated eye for at least 7 days after delivery but not in the other organs tested.
Figure 46:
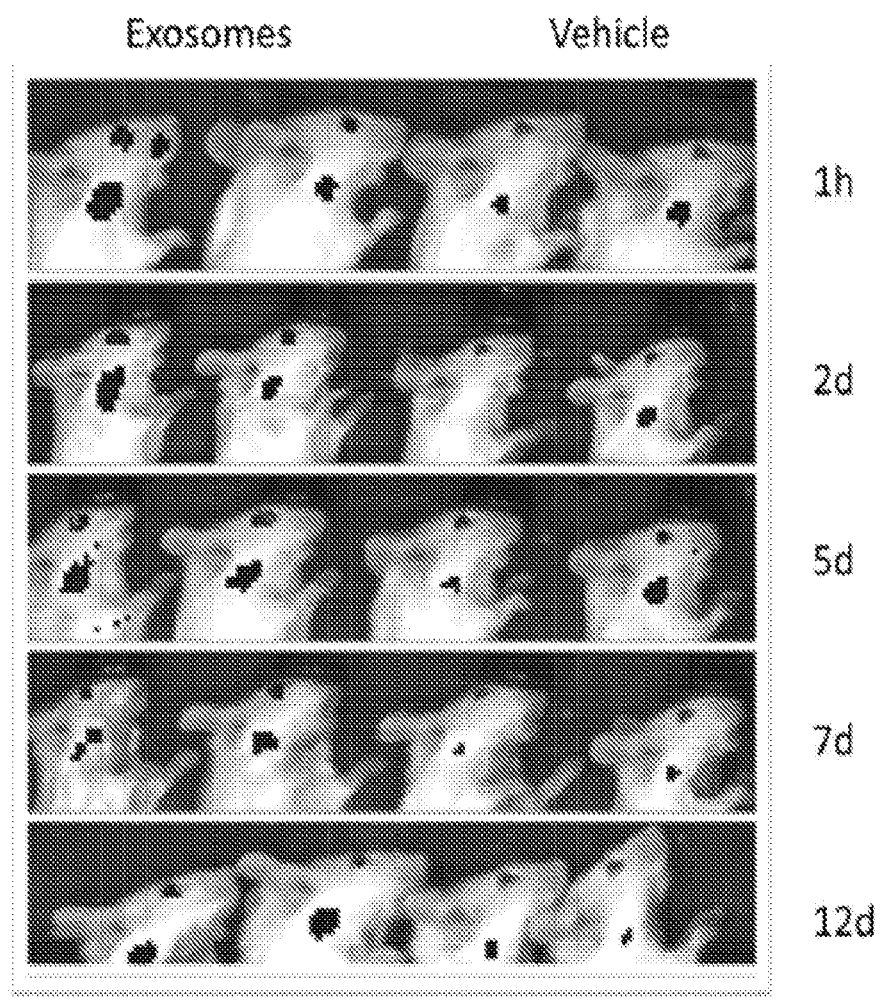
FIG. 46 depicts biodistribution at various times after subconjunctival delivery to mice of free dye ("vehicle") or dye-loaded exosomes (0.5×109 exosomes). Healthy mice were subconjunctival injected with 5×108 particles labeled with DiR in a volume of 15 microliters or with 15 microliters of vehicle containing similar amount of DiR. DiR signal in the eye was followed up for 12 days after product injection using Xenogen IVIS Imaging System DiR signal was observed in the exosome treated eye for at least 7 days after delivery.

Example 13: Biodistribution and Clearance of CDC-EVs after Ocular Administration in Mouse Model Mouse eyes treated with exosomes ($0.5 \times 10^7$, $0.5 \times 10^8$, or $0.5 \times 10^9$) loaded with a fluorescent dye (DiR; 1,1'-dioctadecyl-3,3,3',3'-tetramethylindotricarbocyanine iodide) via a single subconjunctival injection showed persistence of the exosomes in the eye at up to 12 days post-administration (FIGS. 42-44 and 46). Little migration of the exosomes to other tissues in the eye was seen (FIG. 45).

Figure 47:
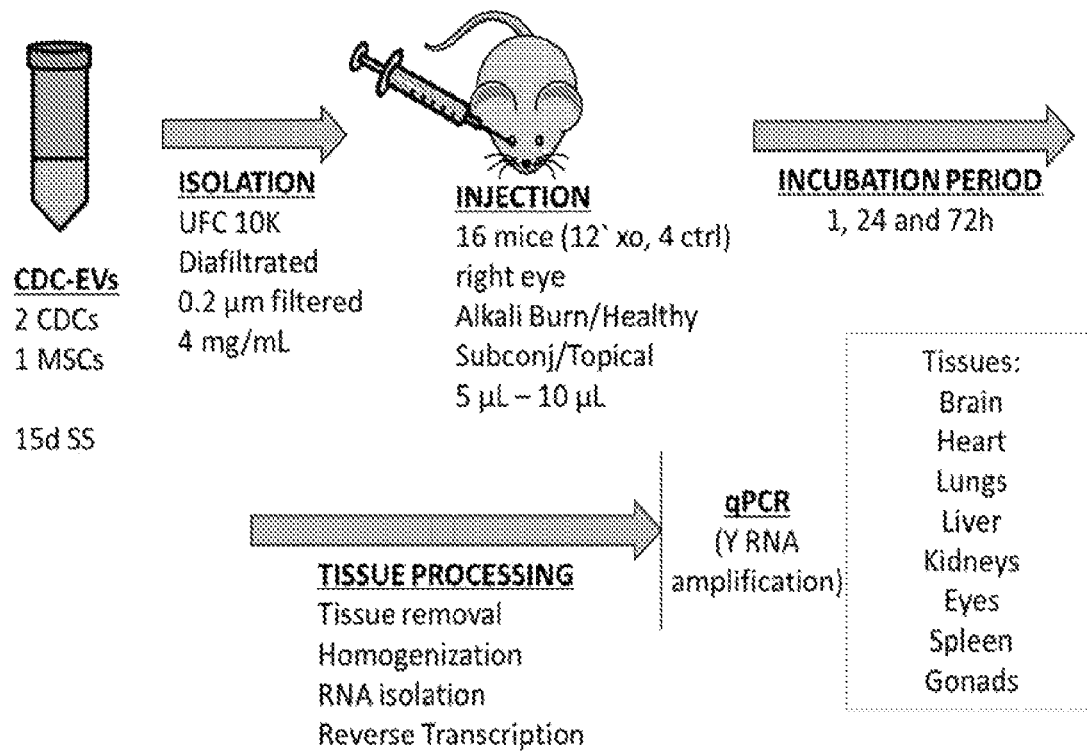
FIG. 47 schematically depicts the study design for evaluation ocular biodistribution and clearance of EVs in a mouse model.
Figure 48A:
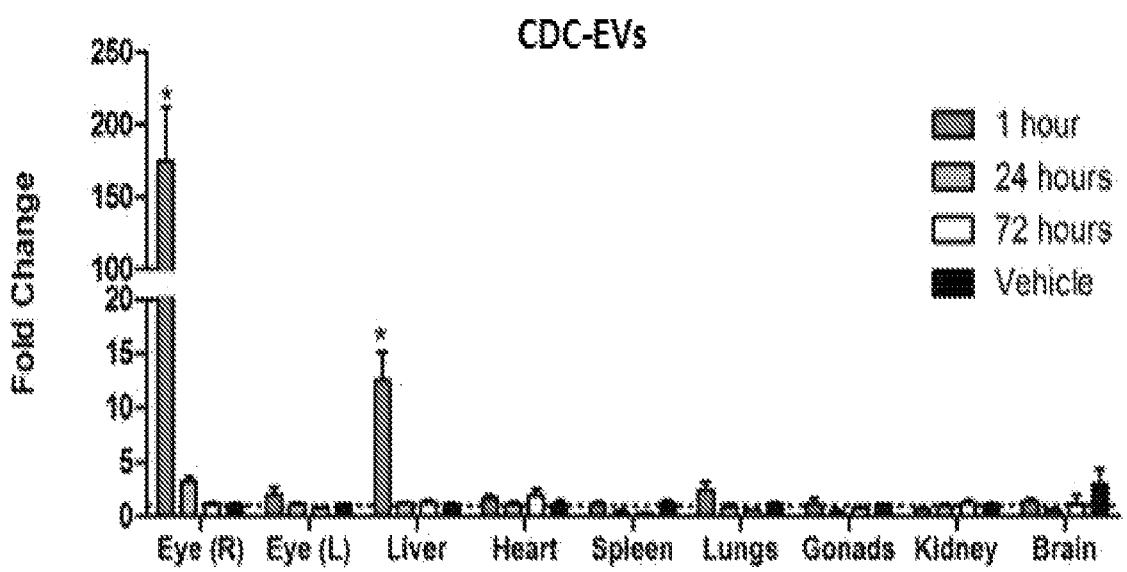
FIG. 48A graphically shows biodistribution of CDC-EVs after subconjunctival administration in a healthy mouse model.
Figure 48B:
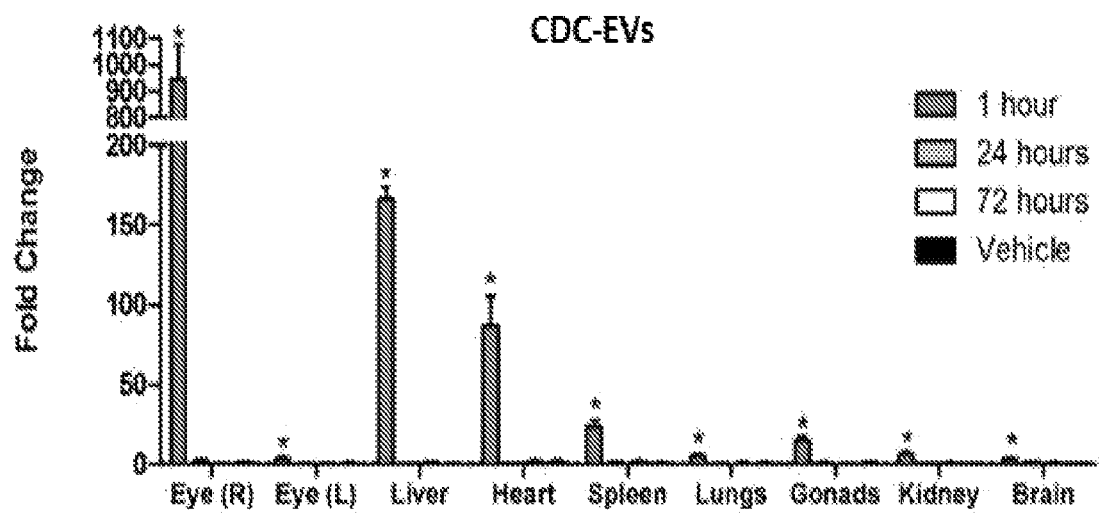
FIG. 48B graphically shows biodistribution of CDC-EVs after alkali burn injury to the right eye with subconjunctival administration.
Figure 48C:
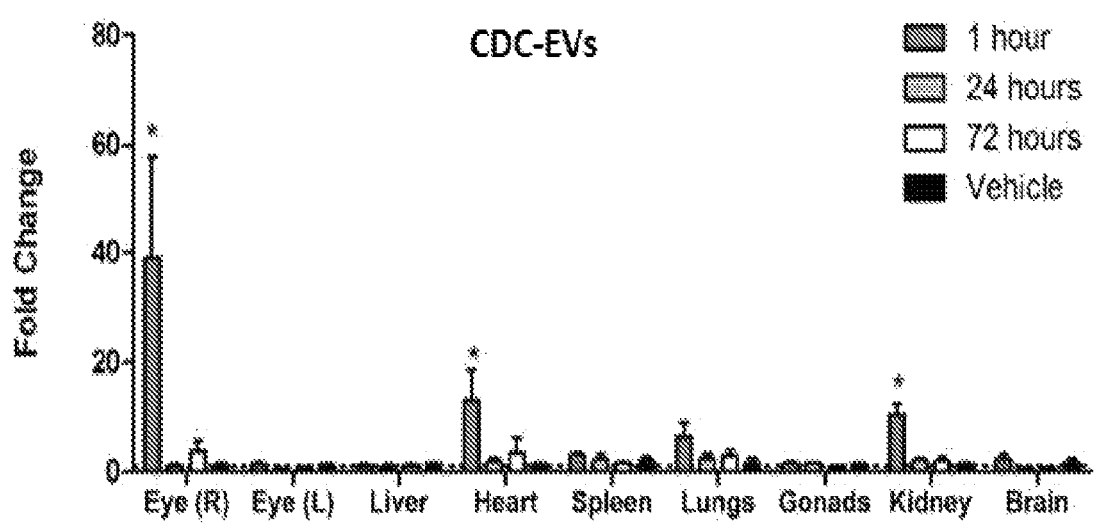
FIG. 48C graphically shows biodistribution of CDC-EVs after topical administration in a healthy mouse.
Figure 48D:
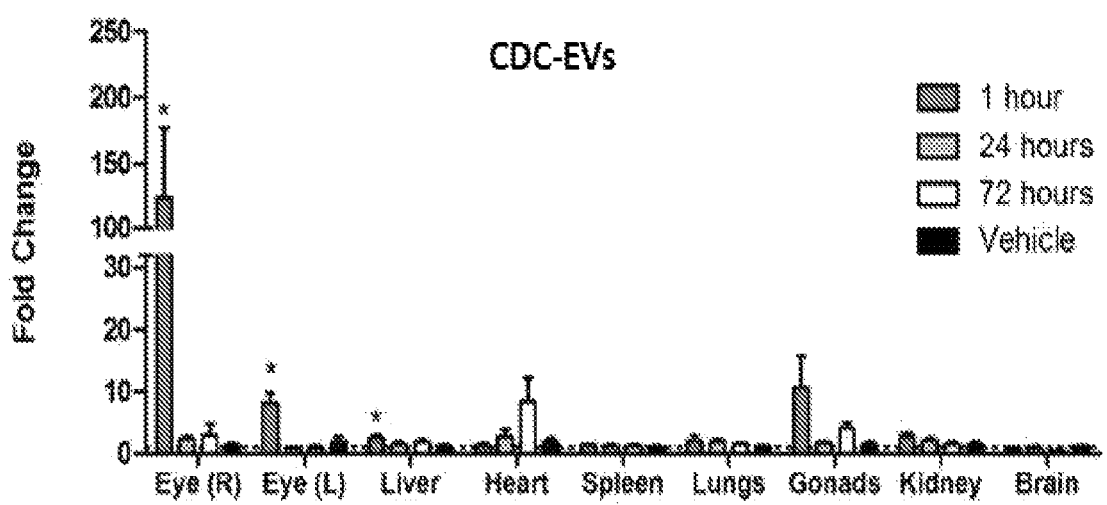
FIG. 48D graphically shows CDC-EV biodistribution with topical administration after alkali burn injury.
Figure 48E:
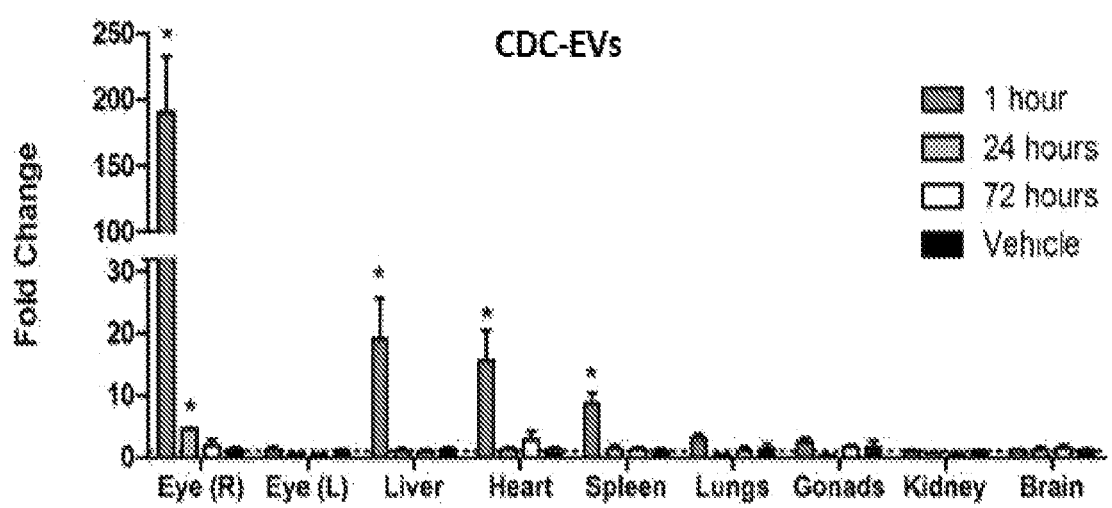
FIG. 48E graphically shows biodistribution of CDC-EVs after subconjunctival administration in healthy mice.
Figure 48F:
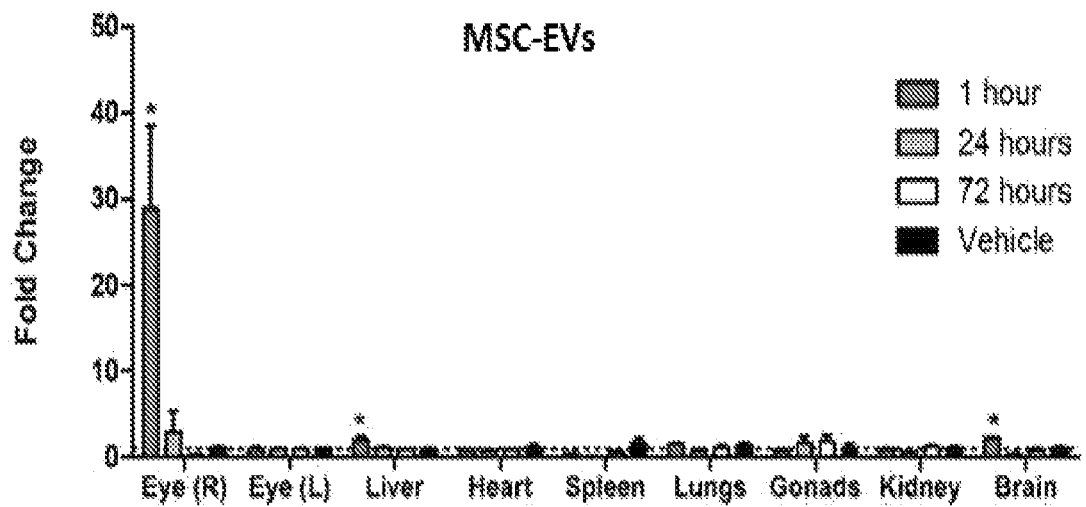
FIG. 48F graphically shows MSC-EV biodistribution after subconjunctival administration in mice with alkali burn injury to the right eye. For FIGS. 48A-F, n=3 or 4, and *=p≤0.05 compared to vehicle.

In addition, a qPCR method detecting an abundant human-specific RNA fragment, 5'-GGU CCG AUG GUA GUG GGU UAU CAG-3' (SEQ ID NO:1) (hY4f), was developed, wherein NCBI nucleotide BLAST 2.6.1 (https://blast.ncbi.nlm.nih.gov/Blast.cgi (7)) was used with hY4f as the query sequence and mouse genomic+transcript was chosen as the database, and the following mouse injection and tissue harvest protocols were used, and as illustrated in FIG. 47.

A) Subconjunctival Administration of CDC-EVs into Healthy Mice

CDC-EVs (5 µL, 4 mg/mL) were injected in the subconjunctival space of the right eye of female FVB mice anesthetized by isofluorane. After 1, 24, or 72 hours, 4 mice were sacrificed and tissues were removed. 4 PlasmaLyte A (VWR)-injected mice were sacrificed 24 hours after injection. Mouse tissue was preserved in RNAlater (ThermoFisher) at −20° C. until further processing was performed.

B) Subconjunctival Administration of CDC-EVs into Alkali Burn Mice

Alkali burn injury was induced on the right eye of 16 female FVB mice by placing a 1/16 inch filter paper soaked in 1 N NaOH on the anesthetized mouse right eye for 30 seconds. The eye was then flushed with saline to remove remaining NaOH. The following day, CDC-EVs (5 µL, 4 mg/mL) were injected in the subconjunctival space of the right eye of 12 of the mice. After 1, 24, or 72 hours, 4 mice were sacrificed and tissues were removed. 4 PlasmaLyte A-injected mice were sacrificed 24 hours after injection. Mouse tissue was preserved in RNAlater at −20° C. until further processing was performed.

C) Topical Administration of CDC-EVs into Healthy Mice

A 20 µL pipet was used to administer a 10 µL drop of CDC-EVs (4 mg/mL) onto the right eye of 10 anesthetized female FVB mice. The procedure was repeated 2 more times, 1 hour apart, for a total of three administrations. 1, 24, or 72 hours after the last dose, 4 mice were sacrificed and tissues were removed. 4 PlasmaLyte A-treated mice were sacrificed 24 hours after delivery. Mouse tissue was preserved in RNAlater at −20° C. until further processing was performed.

D) Topical Administration of CDC-EVs into Alkali Burn Mice

Alkali burn injury was induced and CDC-EVs were delivered as indicated above. 4 PlasmaLyte A-treated mice were sacrificed at 24 hours as in 3.4.3. Mouse tissue was preserved in RNAlater at −20° C. until further processing was performed.

E) Subconjunctival Administration of MSC-EVs into Alkali Burn Mice

Alkali burn injury was induced as indicated above, and MSC-EVs (5 µL) were injected in the subconjunctival space of the right eye of 12 of the mice on the next day. After 1, 24, or 72 hours, 4 mice were sacrificed and tissues were removed. 4 PlasmaLyte A-injected mice were sacrificed at 24 hours. Mouse tissue was preserved in RNA later at −20° C. until further processing was performed.

Tissues were homogenized in Qiazol (Qiagen) using Bead Ruptor 12 (OMNI International) with RNase free steel beads. RNA was isolated using miRNeasy Mini kit (Qiagen), and QuantiMir Kit (Systems Biosciences) was used for reverse transcription. qPCR was done with QuantiTect SYBR green (Qiagen) on QuantStudio 12K Flex or QuantStudio 6 Flex system (Applied Biosystems) with the QuantiMir universal reverse primer, hY4f forward primer (5'-GGTCCGATGGTAGTGGGTTATCAG-3') (SEQ ID NO:2), and mouse U6 forward primer (5'-TGGCCCCTGCGCAAGGATG-3') (SEQ ID NO:3) for the housekeeping gene. Fold change was calculated using 2C-MCt) by comparing the Ct of each tissue to the Ct of that tissue from the PlasmaLyte-injected mice. Significance was determined using student's T-test versus vehicle with $p \leq 0.05$. The results are shown in FIGS. 48A-F. In all experiments, CDC-EVs and MSC-EVs were nearly undetectable after 24 hours, with the exception of the right eye in alkali injured mice subconjunctival injected FIG. 48E, in which signal was 4.6 fold over background.

Figure 49A:
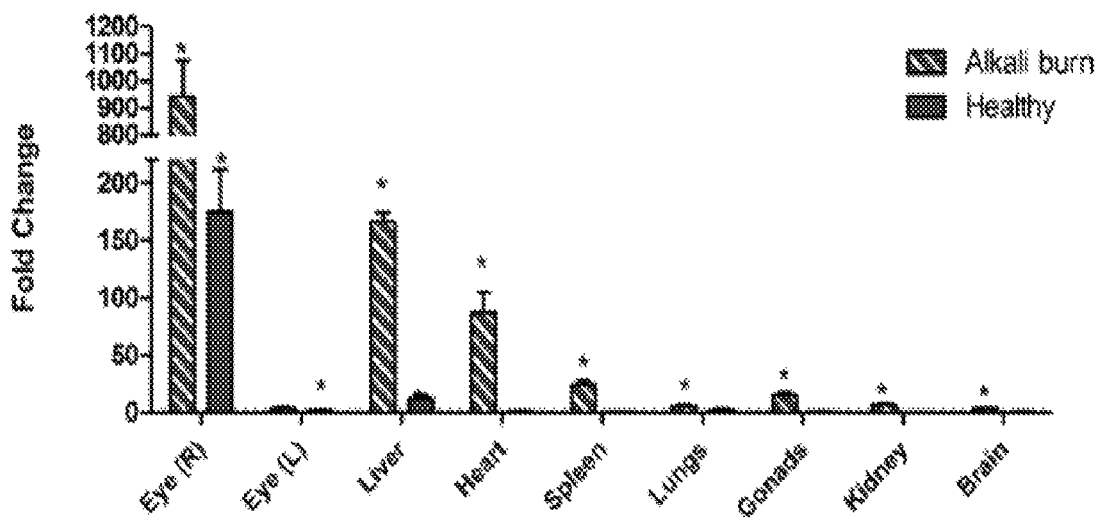
FIGS. 49A-D graphically show CDC-EV 1 hour data, grouped by conjunctival or topical administration and healthy or injured mouse for comparison.
Figure 49B:
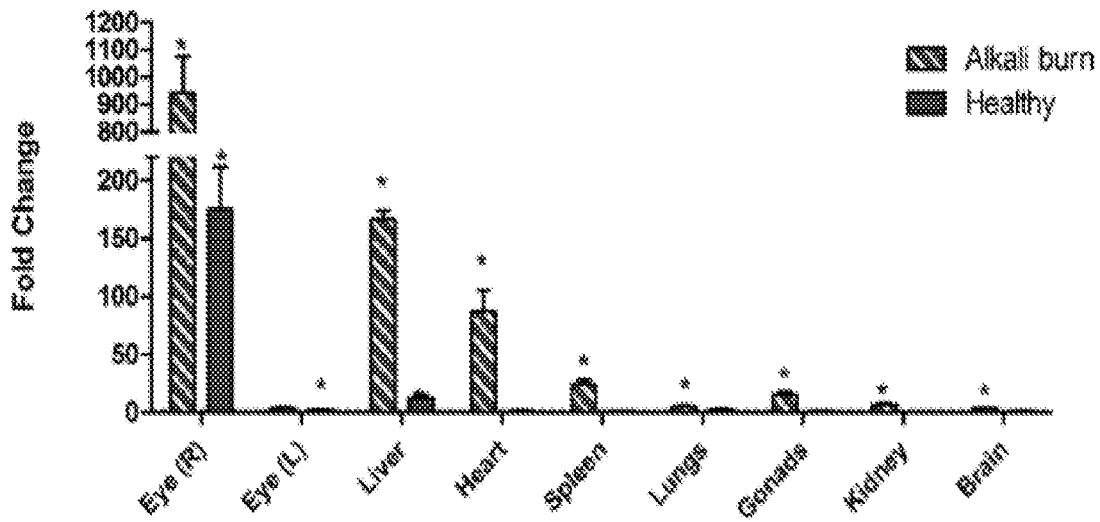
Figure 49C:
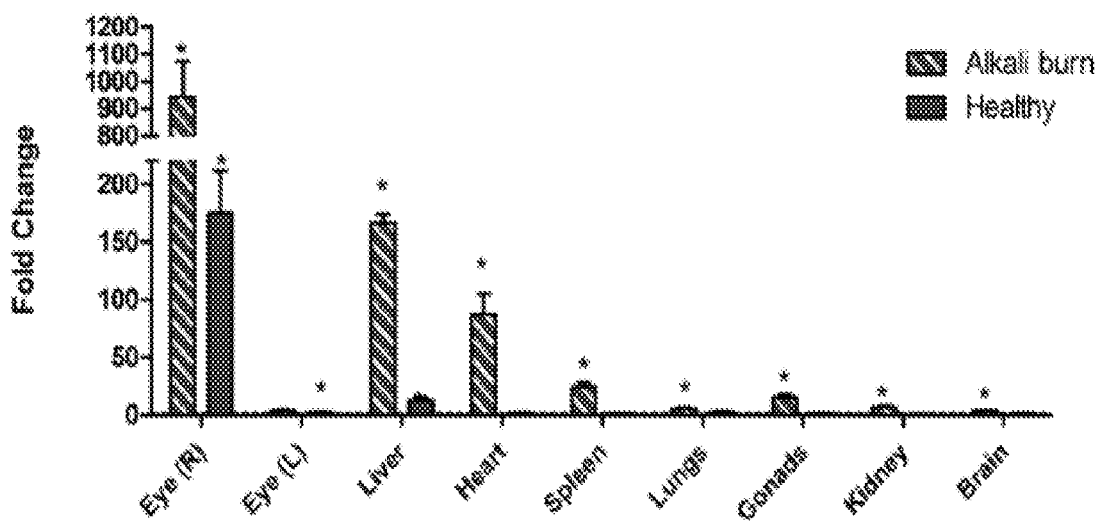
Figure 49D:
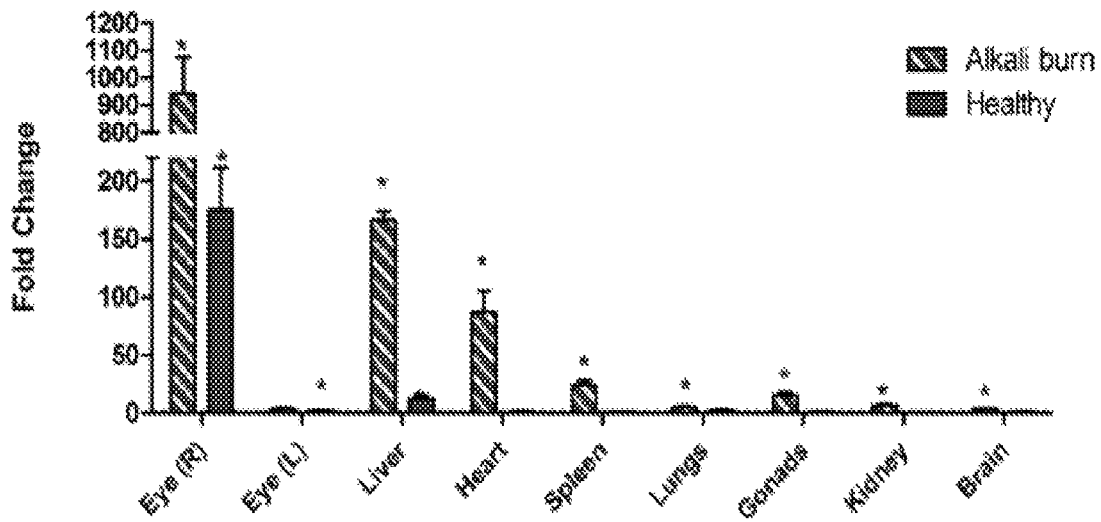

In contrast to subconjunctival administration, CDC-EVs were not found in the liver with topical administration (FIGS. 49A-B). In healthy mice (FIG. 49C), CDC-EVs were detected in the heart and the kidney with topical administration but not with Subconjunctival administration. It is unclear whether this is due to administration route and not due to other factors because the same trend is not seen in the mice with alkali burn injury (FIG. 49D).

Figure 50:
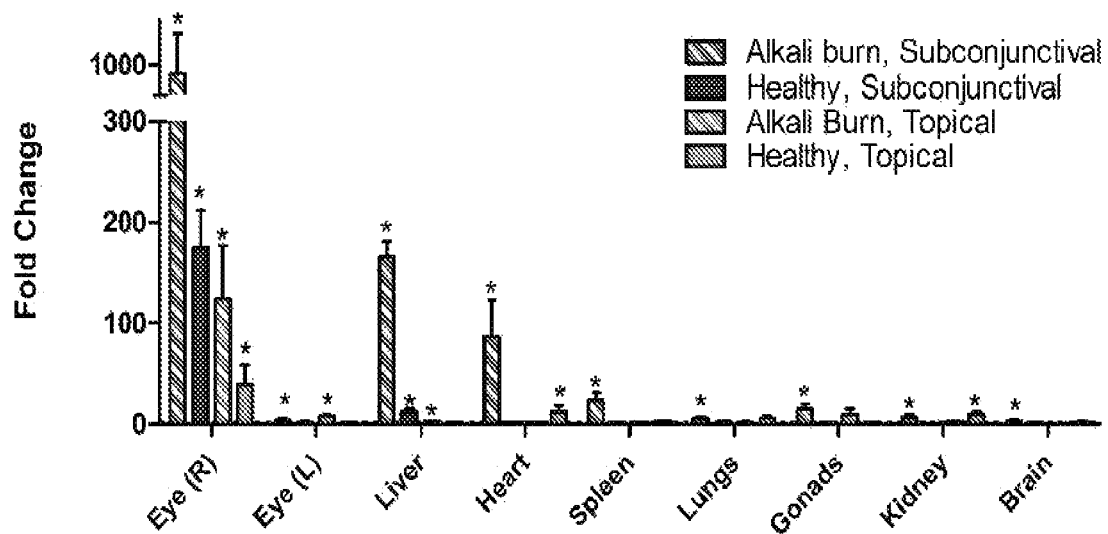
FIG. 50 graphically shows biodistribution comparison of four CDC-EV experiments 1 hour after administration, wherein n=3 or 4, and *=p<0.05 compared to vehicle.

To compare biodistribution after 1 hour, the signals obtained in tissues of mice injected with CDC-EVs 1 hour after delivery were graphed together, as shown in FIG. 50.

CDC-EV Versus MSC-EV Biodistribution

Figure 51:
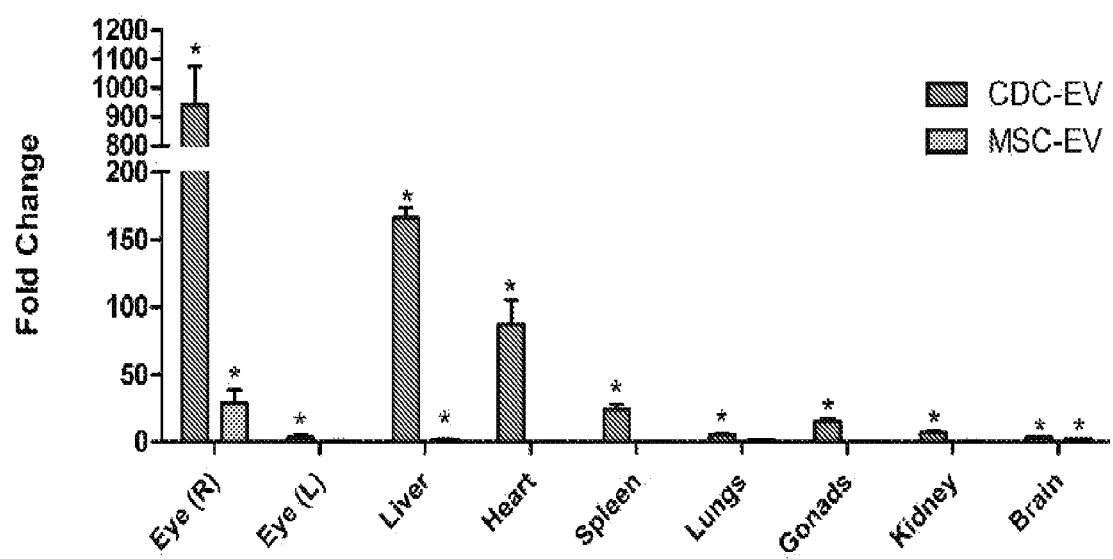
FIG. 51 graphically shows CDC-EV versus MSC-EV biodistribution, wherein n=3 or 4, and *=p<0.05 compared to vehicle.

MSC-EVs were injected into the subconjunctival space of mice with alkali burn injury in the corneal epithelium. EVs were collected from conditioned media obtained after culturing MSC in serum free media for 24. MSC-EV dosing was not measured by protein concentration but by using the same volume of starting CM as used with CDC-EVs. 1 hour after administration, MSC-EVs were found in the right eye, liver, and brain, as shown in FIG. 51.

Proof-of-concept for utility of CDC-EVs in a model approximating the intended clinical indication (ocular GVHD) and bioactivity of CDC-EVs is demonstrated using an animal model of corneal alkali chemical burn in both rats and rabbits. This model recapitulates many of the salient features of the intended indication. In human ocular GVHD, the predominant cell types responsible for inflammation and fibrosis on the ocular surface and lacrimal glands are macrophages, T cells, and neutrophils. See, e.g., Barabino, et al., Ocular surface immunity: homeostatic mechanisms and their disruption in dry eye disease, Prog Retin Eye Res, 31(3): 271-285 (2012). In the alkali chemical burn model, a central corneal application of IN NaOH is made for 30 (rats) or 60 (rabbits) seconds, leading to corneal and conjunctival inflammation, corneal edema, corneal scarring, corneal neovascularization, and corneal epithelial defect. See, e.g., Yao, et al., Role of mesenchymal stem cells on cornea wound healing induced by acute alkali burn, PLoS One 7(2): e30842 (2012). Similar to ocular GVHD, the ocular surface in the alkali chemical burn model becomes infiltrated with macrophages, T cells, and neutrophils, leading to fulminant acute and chronic inflammation, corneal scarring and fibrosis, as well as chronic neovascularization of the cornea. See, e.g., Yao, et al. (2012). In other words, the cellular repertoire present in the alkali chemical burn model resembles that of human ocular GVHD, making this a suitable model to assess the durability of CDC-EVs' efficacy in a chronic ocular inflammatory disease setting.

The clinical phenotypes of ocular GVHD and corneal alkali chemical burns share strong similarities as well. Ocular GVHD, both clinically and in one published mouse model, is characterized by persistent corneal epithelial defects and erosions, chronic corneal neovascularization, corneal fibrosis, limbal stem cell deficiency, conjunctival injection, and decreased ocular surface lubrication, leading to symptoms of severe dry eye. See, e.g., Herretes, et al., Recruitment of Donor T Cells to the Eyes During Ocular GVHD in Recipients of MHC-Matched Allogeneic Hematopoietic Stem Cell Transplants, Invest Ophthalmol Vis Sci 56(4): 2348-2357 (2015). Similarly, in both human and animal eyes, alkali chemical burns to the ocular surface result in profound corneal epithelial defects, corneal neovascularization, corneal fibrosis, limbal stem cell deficiency, conjunctival injury, and severe dry eye symptoms. See, e.g., Hamill, et al., Corneal alkali burns: a review of the literature and proposed protocol for evaluation and treatment, Int Ophthalmol Clin 53(4): 185-194 (2013).

As a function of their common cellular mechanisms and clinical presentations, treatments for ocular GVHD and alkali chemical burns of the eye tend to overlap as well. Both conditions are typically treated with a combination of topical lubricants, autologous serum, corticosteroids, scleral contact lenses, amniotic membrane transplantation and, in the cases of severe disease, limbal stem cell transplantation, penetrating keratoplasty, or keratoprosthesis. See, e.g., Shikari, et al., Ocular graft-versus-host disease: a review, Surv Ophthalmol 58(3): 233-251 (2013).

The invention claimed is:

1. A method of treating Sjogren's syndrome in a human in need thereof comprising administering a therapeutically effective amount of extracellular vesicles produced from cardiosphere-derived cells to said human in need thereof to effectively treat the Sjogren's syndrome in said human in need thereof.

2. The method according to claim 1, wherein said administration is via topical administration or subconjunctival injection.

3. The method according to claim 1, wherein the extracellular vesicles are exosomes.

4. The method according to claim 1, wherein said therapeutically effective amount of extracellular vesicles is $1.0 \times 10^5$ to $1.0 \times 10^9$ extracellular vesicles.

5. The method according to claim 1, wherein said therapeutically effective amount of extracellular vesicles is $1.0 \times 10^5$ to $1.0 \times 10^9$ extracellular vesicles per kilogram body weight of said human.

6. The method according to claim 1, wherein said therapeutically effective amount of extracellular vesicles is $1.0 \times 10^5$ to $1.0 \times 10^9$ extracellular vesicles per gram weight of the eye.

7. The method according to claim 1, wherein said therapeutically effective amount of extracellular vesicles is $1.0 \times 10^5$ to $1.0 \times 10^9$ exosomes.

8. The method according to claim 1, wherein said therapeutically effective amount of extracellular vesicles is $1.0 \times 10^5$ to $1.0 \times 10^9$ exosomes per kilogram body weight of said human.

9. The method according to claim 1, wherein said therapeutically effective amount of extracellular vesicles is $1.0 \times 10^5$ to $1.0 \times 10^9$ exosomes per gram weight of the eye.

* * * * *

SEQUENCE LISTING

```
<160> NUMBER OF SEQ ID NOS: 3

<210> SEQ ID NO 1
<211> LENGTH: 24
<212> TYPE: RNA
<213> ORGANISM: Homo sapiens

<400> SEQUENCE: 1
gguccgaugg uaguggguua ucag                                          24

<210> SEQ ID NO 2
<211> LENGTH: 24
<212> TYPE: DNA
<213> ORGANISM: Homo sapiens

<400> SEQUENCE: 2
ggtccgatgg tagtgggtta tcag                                          24

<210> SEQ ID NO 3
<211> LENGTH: 19
<212> TYPE: DNA
<213> ORGANISM: Homo sapiens

<400> SEQUENCE: 3
tggcccctgc gcaaggatg                                                19
```